US010016505B2

(12) United States Patent
Mariner et al.

(10) Patent No.: US 10,016,505 B2
(45) Date of Patent: Jul. 10, 2018

(54) BIOMATERIALS FOR DELIVERY OF BLOOD EXTRACTS AND METHODS OF USING SAME

(71) Applicant: Mosaic Biosciences, Inc., Boulder, CO (US)

(72) Inventors: Peter D. Mariner, Superior, CO (US); Martin Stanton, Boulder, CO (US); Alexei Kazantsev, Boulder, CO (US); Jeanne Callan, Boulder, CO (US)

(73) Assignee: MOSAIC BIOSCIENCES, INC., Boulder, CO (US)

( * ) Notice: Subject to any disclaimer, the term of this patent is extended or adjusted under 35 U.S.C. 154(b) by 1089 days.

(21) Appl. No.: 13/758,942

(22) Filed: Feb. 4, 2013

(65) Prior Publication Data

US 2013/0243878 A1    Sep. 19, 2013

Related U.S. Application Data

(63) Continuation-in-part of application No. PCT/US2013/024520, filed on Feb. 1, 2013.

(60) Provisional application No. 61/594,116, filed on Feb. 2, 2012.

(51) Int. Cl.
| | |
|---|---|
| A61K 35/14 | (2015.01) |
| A61K 47/32 | (2006.01) |
| A61L 27/54 | (2006.01) |
| C08L 71/02 | (2006.01) |
| A61L 27/36 | (2006.01) |
| A61L 27/52 | (2006.01) |
| A61L 27/58 | (2006.01) |

(52) U.S. Cl.
CPC .............. *A61K 47/32* (2013.01); *A61K 35/14* (2013.01); *A61L 27/3616* (2013.01); *A61L 27/52* (2013.01); *A61L 27/54* (2013.01); *A61L 27/58* (2013.01); *C08L 71/02* (2013.01)

(58) Field of Classification Search
CPC ........ A61K 35/12; A61K 35/35; A61K 35/16; A61K 35/28
USPC .................................. 424/93.1, 29, 530, 531
See application file for complete search history.

(56) References Cited

U.S. PATENT DOCUMENTS

| | | | |
|---|---|---|---|
| 3,920,877 A | 11/1975 | Barber et al. | |
| 4,081,598 A | 3/1978 | Morgan et al. | |
| 4,808,638 A | 2/1989 | Steinkraus et al. | |
| 4,969,998 A | 11/1990 | Henn | |
| 5,177,056 A | 1/1993 | Hilti et al. | |
| 5,399,624 A | 3/1995 | Glaser et al. | |
| 5,410,016 A | 4/1995 | Hubbell et al. | |
| 5,496,872 A | 3/1996 | Constancis et al. | |
| 5,730,601 A | 3/1998 | Bowman et al. | |
| 5,837,751 A | 11/1998 | Jacobine et al. | |
| 5,858,746 A | 1/1999 | Hubbell et al. | |
| 6,060,582 A | 5/2000 | Hubbell et al. | |
| 6,169,126 B1 | 1/2001 | Szum et al. | |
| 7,018,655 B2 | 3/2006 | Lele et al. | |
| 7,288,608 B2 | 10/2007 | Bowman et al. | |
| 7,744,912 B1 | 6/2010 | Hubell et al. | |
| 7,842,667 B2 | 11/2010 | Seliktar et al. | |
| 8,519,086 B2 | 8/2013 | Bowman et al. | |
| 8,859,716 B2 | 10/2014 | Bowman et al. | |
| 9,631,092 B2 | 4/2017 | Bowman et al. | |
| 2002/0004537 A1 | 1/2002 | Krongauz et al. | |
| 2002/0076443 A1 | 6/2002 | Stein et al. | |
| 2004/0086479 A1 | 5/2004 | Grinstaff et al. | |
| 2004/0091462 A1 | 5/2004 | Lin et al. | |
| 2005/0244393 A1 | 11/2005 | Philippart et al. | |
| 2006/0029578 A1 | 2/2006 | Hoemann et al. | |
| 2006/0204582 A1 | 9/2006 | Stein et al. | |
| 2007/0248567 A1 | 10/2007 | Pathak et al. | |
| 2009/0311338 A1* | 12/2009 | Pathak ............. | A61K 47/48215 424/529 |
| 2009/0324720 A1* | 12/2009 | He ....................... | A61K 9/0024 424/484 |
| 2010/0137510 A1 | 6/2010 | Seliktar et al. | |
| 2010/0233246 A1 | 9/2010 | Sehl et al. | |
| 2010/0291357 A1 | 11/2010 | Polizzotti et al. | |
| 2010/0304338 A1 | 12/2010 | Cramer et al. | |

(Continued)

FOREIGN PATENT DOCUMENTS

| | | |
|---|---|---|
| GB | 588018 A | 5/1947 |
| JP | 363-280711 A | 11/1988 |

(Continued)

OTHER PUBLICATIONS

Anderson et al. "The performance of human mesenchymal stem cells encapsulated in cell-degradable polymer-peptide hydrogels", Biomaterials. May 2011; 32(14); 3564.*
Lin et al. (Proceedings of the 28th IEEE, EMBS Annual International Conference, New York City, USA, Aug. 30-Sep. 3, 2006).*
Fairbanks et al. "Thiol-Yne Photopolymerizations: Novel Mechanism, Kinetics, and Step-Growth Formation of Highly Cross-Linked Networks"., Macromolecules, 2009, 42, pp. 211-217.*
[Author Unknown], "Maleimide," (web pages, year, date, and month unknown), retrieved from www.wikipedia.org on Mar. 3, 2012.
Anderson et al. (2011). "The Performance of Human Mesenchymal Stem Cells Encapsulated in Cell-Degradable Polymer-peptide Hydrogels," Biomaterials 32:3564-3574. pp. 1-19.

(Continued)

*Primary Examiner* — Christopher R Tate
*Assistant Examiner* — Deborah A Davis
(74) *Attorney, Agent, or Firm* — Morrison & Foerster LLP

(57) ABSTRACT

The disclosure provides biomaterials including scaffolds that include blood products including blood fractions and products including platelets for administration to subjects in need thereof. More specifically, the scaffolds based on step growth polymers are enriched with blood extracts that contain platelet rich plasma (PRP) and/or extracts of platelets. Compositions comprising a biomaterial or precursor thereof and a blood extract are provided, as are methods of making and using the biopolymers or precursors thereof. Kits and articles of manufacture comprising the biopolymers or precursors thereof are also described.

21 Claims, 16 Drawing Sheets

(56) References Cited

U.S. PATENT DOCUMENTS

| | | | |
|---|---|---|---|
| 2012/0225101 A1 | 6/2012 | Kao et al. | |
| 2012/0202263 A1* | 8/2012 | Blakely | C07K 14/78 435/188 |
| 2013/0197189 A1 | 8/2013 | Aimetti et al. | |
| 2014/0038826 A1 | 2/2014 | Anseth et al. | |
| 2014/0039085 A1 | 2/2014 | Bowman et al. | |
| 2014/0112960 A1 | 4/2014 | Lin | |
| 2014/0273153 A1 | 9/2014 | Kazantsev et al. | |
| 2015/0133302 A1 | 5/2015 | Bowman et al. | |
| 2016/0068639 A1 | 3/2016 | Bowman et al. | |

FOREIGN PATENT DOCUMENTS

| | | |
|---|---|---|
| WO | WO-2012/103445 | 8/2012 |
| WO | WO-2013/116791 A1 | 8/2013 |
| WO | WO-2016/130573 A2 | 8/2016 |

OTHER PUBLICATIONS

Athanasiou, K.A. et al. (1996). "Sterilization, Toxicity, Biocompatibility and Clinical Applications of Polylactic Acid/Polyglycolic Acid Copolymers," Biomaterials 17(2):93-102.

Bowman, et al., "Unpublished U.S. Appl. No. 14/485,490, filed Sep. 12, 2014, titled" Degradable Thiol-Ene Polymers.

Cadée, J.A. et al. (Jun. 5, 2000). "In Vivo Biocompatibility of Dextran-Based Hydrogels," J Biomed Mater Res. 50(3):397-404.

Chalker, et al., "Enabling Olefin Metathesis on Proteins: Chemical Methods for Installation of S-Allyl Cysteine", Chem. Commun., 2009, pp. 3714-3716.

Conte, et al., "Multi-Molecule Reaction of Serum Albumin Can Occur Through Thiol-Yne Coupling", Chemical Communications, vol. 47, 2011, pp. 11086-11088.

Cramer, et al., "Thiol-Ene Photopolymerization Mechanism and Rate Limiting Step Changes for Various Vinyl Functional Group Chemistries", Macromolecules, vol. 36, 2003, pp. 7964-7969.

Dondoni, et al., "A New Ligation Strategy for Peptide and Protein Glycosylation: Photoinduced Thiol-Ene Coupling", Chemistry—A European Journal, vol. 15, 2009, pp. 11444-11449.

Draye, J-P. et al. (Sep. 1998). "In Vitro and in Vivo Biocompatibility of Dextran Dialdehyde Cross-linked Gelatin Hydrogel Films," Biomaterials 19(18):1677-1687.

Floyd, et al., "Thiyl Glycosylation of Olefinic Proteins: S-Linked Glycoconjugate Synthesis", Angewandte Chemie International Edition, vol. 48, 2009, pp. 7798-7802.

Fu et al., In situ forming poly( ethylene glycol)-based hydrogels via thiol-maleimide Michael-type addition, J. Biomed. Mater. Res., Aug. 2011, vol. 98A, No. 2, pp. 201-2011. pp. 1-30.

Gallez, B. et al. (Jul. 1998). "Small Particles of Fusinite and Carbohydrate Chars Coated with Aqueous Soluble Polymers: Preparation and Applications for In Vivo EPR Oximetry," Magn Reson Med. 40(1):152-159.

Geyer, U. et al. (1994). "Formation, Derivatization and Applications of Bacterial Cellulose," Int. J. Biol. Macromol. 16(6):343-347.

Hernandez et al., "Control of Protein Immobilization: Coupling Immobilization and Site-directed Mutagenesis to Improve biocatalyst or Biosensor Performance" Enzyme & Microbial Technology., vol. 48, 2011, pp. 107-122.

International Search Report dated Apr. 11, 2013 for PCT Patent Application No. PCT/US/2013/24520 filed on Feb. 1, 2013, three pages.

Jain, R.A. (2000). "The Manufacturing Techniques of Various Drug Loaded Biodegradable Poly(lactide-co-glycolide) (PLGA) Devices," Biomaterials 21:2475-2490.

Jin et al., "Synthesis and characterization of hyaluronic acid-poly(enthylene glycol) hydrogels via Michael addition: An injectable biomaterial for cartilage repair," Acta Biomaterialia, 2010 (month unknown), vol. 6, pp. 1968-1977.

Li, et al., "Genetically Encoded Alkenyl-Pyrrolysine Analogues for Thiol-Ene Reaction Mediated Site-Specific Protein Labeling", Chemical Science, vol. 3, 2012, pp. 2766-2770.

McCall, et al., "Thiol-Ene Photopolymerizations Provide a Facile Method to Encapsulate Proteins and Maintain Their Bioactivity", Biomacromolecules, vol. 13, 2012, pp. 2410-2417.

Moreira, H. et al. (Feb. 2000). "Use of Bioresorbable Membrane (Sodium Hyaluronate + Carboxymethylcellulose) After Controlled Bowel Injuries in a Rabbit Model," Diseases of the Colon Rectum 43(2):182-187.

Non-Final Office Action dated May 8, 2015, for U.S. Appl. No. 14/485,490, filed dated Sep. 12, 2014, 10 pages.

Non-Final Office Action dated Jul. 16, 2015, for U.S. Appl. No. 14/210,106, filed Mar. 13, 2014, (10 pages).

Qiu, B. et al. (2003). "A hydrogel prepared by in situ cross-linking of a thiol-containing poly (ethylene glycol)-based copolymer: a new biomaterial for protein drug delivery," Biomaterials 24:11-18.

Raza et al. (2013). "The Influence of Matrix Degradation and Functional on Cell Survival and Morphogenesis in PEG-Based Hydrogels," Macromolecular Bioscience 13:1048-1058. pp. 1-20.

Restriction Requirement dated Feb. 12, 2015, for U.S. Appl. No. 14/210,106, filed Mar. 13, 2014, (6 pages).

Roberts et al. (2013). "Comparison of Photopolymerizable Thiol-ene PEG and Acrylate-based PEG Hydrogels for Cartilage Development," Biomaterials 34(38):9969-9979.

Roskos, K.V. et al. (1995). "Biocompatibility and in Vivo Morphine Diffusion into a Placebo Morphine-triggered Naltrexone Delivery Device in Rabbits," Biomaterials 16(16):1235-1239.

Veronese, "Peptide and Protein PEGylation: a Review of Problems and Solutions", Biomaterials, vol. 22, 2001, pp. 405-417.

Wiese, K.G. (1993). "Osmotically Induced Tissue Expansion with Hydrogels: A New Dimension in Tissue Expansion? A Preliminary Report," Journal of Cranio-Maxillo-Facial Surgery 21:309-313.

Written Opinion dated Apr. 11, 2013 for PCT Patent Application No. PCT/US2013/24520 filed on Feb. 1, 2013, six pages.

Wu et al., "Reactive Polymer Coatings: A General Route t Thiol-ene and Thiol-yne Click Reactions" Macromol. Rapid Commun., 2012, vol. 33, pp. 922-927.

U.S. Appl. No. 60/328,669, filed Oct. 10, 2001, by Bowman et al.

U.S. Appl. No. 14/848,141, filed Sep. 8, 2015, by Bowman et al.

Fairbanks, B. D. et al., (2009). "Thiol-Yne Photopolymerizations; Novel Mechanism, Kinetics, and Step-Growth Formation of Highly Cross-Linked Networks," Macromolecules 42:211-217.

Fairbanks, B.D. et al., (2010) "Reaction Rates and Mechanisms for Radical, Photoinitated Addition of Thiols to Alkynes, and Implications for Thiol-Yne Photopolymerizations and Click Reactions," Macromolecules 43:4113-4119.

Final Office Action dated Jun. 5, 2006, for U.S. Appl. No. 10/269,916, filed Oct. 10, 2002, 7 pages.

Final Office Action dated Mar. 10, 2009, for U.S. Appl. No. 11/858,062, filed Sep. 19, 2007, 6 pages.

Final Office Action dated May 31, 2011, for U.S. Appl. No. 12/556,640, filed Sep. 10, 2009, 5 pages.

Final Office Action dated Sep. 14, 2012, for U.S. Appl. No. 12/556,640, filed Sep. 10, 2009, 10 pages.

Final Office Action dated Nov. 30, 2015, for U.S. Appl. No. 13/981,885, filed Oct. 9, 2013,17 pages.

Final Office Action dated Jan. 29, 2016, for U.S. Appl. No. 14/210,106, filed Mar. 13, 2014,11 pages.

Hoyle, C.E. et al., (2004) "Thiol-Enes: Chemistry of the Past with Promise for the Future" Journal of Polymer Science: Part A: Polymer Chemistry 42:5301-5338.

International Preliminary Report on Patentability dated Jul. 30, 2013, for PCT Patent Application No. PCT/US2012/022920, filed Jan. 27, 2012, 7pages.

International Search Report dated Jan. 3, 2003, for PCT Patent Application No. PCT/US02/32669, filed Oct. 10, 2002, 1 page.

International Search Report and Written Opinion dated Aug. 30, 2012, for PCT Patent Application No. PCT/US2012/022920, Internationally filed on Jan. 27, 2012, 9 pages.

Lin, C.C. et al., (2011) "PEG Hydrogels Formed by Thiol-Ene Photo-Click Chemistry and Their Effect on the Formation and Recovery of Insulin-Secreting Cell Spheroids," Biomaterials 32(36):9685-9695.

Non Final Office Action dated Dec. 30, 2005, for U.S. Appl. No. 10/269,916, filed Oct. 10, 2002, 6 pages.

(56) References Cited

OTHER PUBLICATIONS

Non Final Office Action dated Aug. 6, 2008, for U.S. Appl. No. 11/858,062, filed Sep. 19, 2007, 6 pages.
Non Final Office Action dated Oct. 25, 2010, for U.S. Appl. No. 12/556,640, filed Sep. 10, 2009, 9 pages.
Non Final Office Action dated Nov. 20, 2013, for U.S. Appl. No. 13/951,268, filed Jul. 25, 2013, 9 pages.
Non-Final Office Action dated Jul. 16, 2015, for U.S. Appl. No. 14/210,106, filed Mar. 13, 2014, 10 pages.
Non-Final Office Action dated Apr. 3, 2015, for U.S. Appl. No. 13/981,885, filed Oct. 9, 2013, 16 pages.
Notice of Allowance dated Dec. 14, 2006, for U.S. Appl. No. 10/269,916, filed Oct. 10, 2002, 6 pages.
Notice of Allowance dated Jun. 19, 2007, for U.S. Appl. No. 10/269,916, filed Oct. 10, 2002, 6 pages.
Notice of Allowance dated Apr. 26, 2013, for U.S. Appl. No. 12/556,640, filed Sep. 10, 2009, 6 pages.
Notice of Allowance dated Jun. 11, 2014, for U.S. Appl. No. 13/951,268, filed Jul. 25, 2013, 13 pages.
Restriction Requirement dated Sep. 13, 2005, for U.S. Appl. No. 10/269,916, filed Oct. 10, 2002, 5 pages.
Supplementary European Search Report dated Dec. 14, 2015, for European Patent Application No. 13743245.6, filed on Feb. 1, 2013, 11 pages.
Written Opinion dated Aug. 30, 2012, for PCT Application No. PCT/US2012/022920, filed on Jan. 27, 2012, 6 pages.
European Office Action for European Application No. 13743245.6, dated Jan. 18, 2017, filed on Feb. 1, 2013, 5 pages.
Fu, Y. et al. (Jan. 2012), "3D Cell Entrapment in Crosslinked Thiolated Gelatin-poly(ethylene glycol) Diacrylate Hydrogels," *Biomaterials* 33(1):48-58.
International Preliminary Report on Patentability dated Aug. 8, 2013 for PCT Patent Application No. PCT/US2012/022920, filed on Jan. 27, 2012, 8 pages.

International Search Report dated Aug. 18, 2016, for PCT Patent Application No. PCT/US2016/17189, Internationally filed on Feb. 9, 2016, 4 pages.
Jones, M.W. et al., (2009). "Phosphine-Mediated One-Pot Thiol-Ene "Click" Approach to Polymer-Protein Conjugates," *Chem. Commun.*, 5272-5274.
Lowe, A.B. et al. (2010). "Thiol-yne Click Chemistry: A Powerful and Versatile Methodology for Materials Synthesis," *Journal of Materials Chemistry*, 20:4745-4750.
Non-Final Office Action dated Jul. 18, 2016, for U.S. Appl. No. 13/981,885, filed Oct. 9, 2013, 18 pages.
Non-Final Office Action dated Sep. 16, 2016, for U.S. Appl. No. 14/210,106, filed Mar. 13, 2014, 12 pages.
Non-Final Office Action dated May 19, 2016, for U.S. Appl. No. 14/848,141, filed Sep. 8, 2015, 12 pages.
Notice of Allowance dated Dec. 16, 2016 for U.S. Appl. No. 14/848,141, filed Sep. 8, 2015, 7 pages.
Restriction Requirement dated Jul. 13, 2005, for U.S. Appl. No. 10/269,916, filed Oct. 10, 2002. 9 pages.
Restriction Requirement dated Nov. 20, 2014 for U.S. Appl. No. 13/981,885, filed Oct. 9, 2013, 11 pages.
Russo, L. et al. (Mar. 2016; e-published on Dec. 9, 2015). "Gelatin Hydrogels via Thiol-ene Chemistry," *Monatshefte Für Chemie* 147(3):587-592.
Sell, S.A. et al. (Dec. 2012) "The Incorporation and Controlled Release of Platelet-Rich Plasma-Derived Biomolecules From Polymeric Tissue Engineering Scaffolds," *Polym. Int.* 61(12):1703-1709.
Written Opinion dated Aug. 18, 2016, for PCT Patent Application No. PCT/US2016/17189, Internationally filed on Feb. 9, 2016, 6 pages.
Yan, J. et al. (Oct. 8, 2013). "Growing Hyperbranched Polymers Using Natural Sunlight", *Scientific Reports* 3(2841):1-7.
European Office Action dated Apr. 3, 2018 for EP Application No. 13743245.6 filed Jul. 30, 2014, 7 pages.

\* cited by examiner

Outgrowth of human dermal fibroblasts from collagen plugs embedded in biomaterials carrying blood extracts

BIOMATERIALS FOR DELIVERY OF BLOOD EXTRACTS AND METHODS OF USING SAME

CROSS-REFERENCE TO RELATED APPLICATIONS

This application is a continuation-in-part of, and claims priority benefit to, PCT Application No. PCT/US13/24520, entitled Biomaterials for Delivery of Blood Extracts and Methods of Using Same, filed Feb. 1, 2013, which claims the priority benefit of U.S. Provisional Patent Application Ser. No. 61/594,116, entitled Biomaterials for Delivery of Blood Extracts and Methods of Using Same, filed Feb. 2, 2012, the disclosure of each of which is incorporated herein by reference in its entirety.

SEQUENCE LISTING

The Sequence Listing submitted in an ASCII text file, in accordance with 37 C.F.R. § 1.821(c) and (e), is incorporated by herein by reference. The text file name is "700032000500_Sequence_Listing.txt", the date of creation of the text file is Feb. 4, 2013, and the size of the ASCII text file in bytes is 9,084.

BACKGROUND

Blood can be fractionated into several component parts. One of these component parts, platelet rich plasma (PRP) is blood plasma that has been enriched for platelets. As a concentrated source of autologous platelets, PRP contains (and releases through degranulation) several different growth factors and other cytokines that stimulate healing of bone and soft tissue. The efficacy of certain growth factors in healing various injuries and the concentrations of these growth factors found within PRP are the theoretical basis for the use of PRP in tissue and bone repair. The platelets collected in PRP can be activated by the addition of thrombin and calcium chloride, which induces the release of these factors from alpha granules. PRP and other blood extracts also contain other proteins, such as collagen, fibrinogens and fibronectin, amongst others, that have both signaling and scaffolding properties. Upon delivery of PRP to a tissue or bone defect, these proteins can form a gel that serves as a provisional matrix (e.g., a scaffold) that can support tissue or bone regeneration. Thus, PRP and other blood extracts can support two sometimes overlapping functions: delivery of growth factors and establishment of a scaffold to support tissue or bone regeneration.

There are, at present, two methods of PRP preparation approved by the U.S. Food and Drug Administration. Both processes involve the collection of whole blood that is anticoagulated with citrate dextrose before undergoing two stages of centrifugation designed to separate the PRP aliquot from platelet-poor plasma and red blood cells. In humans, the typical baseline blood platelet count is approximately 200,000 per μL. Therapeutic PRP concentrates the platelets by roughly five-fold. There is however broad variability in the production of PRP by various concentrating equipment and techniques.

In humans, PRP has been investigated and used as a clinical tool for several types of medical treatments, including pain, sports injury, nerve injury, tendinitis, osteoarthritis, cardiac muscle injury, bone repair and regeneration, plastic surgery, and oral surgery.

In clinical settings, PRP is delivered to the body in one of two ways, depending on the specific application. For open wounds (surgical procedures, diabetic ulcers, etc.), PRP is activated by the addition of thrombin and calcium chloride, which results in the release of clotting factors that cause the PRP to coagulate into a gelatinous form. The activation of PRP in these settings both stimulates the release of growth factors and allows for the material to be held in place during clinical procedures. For applications that involve PRP injections into tissues (joints injuries, tendonitis, arthritis, etc.), pre-activation of the PRP with thrombin and calcium chloride is neither required nor advantageous. Platelets are naturally activated when they come in contact with extracellular matrix proteins like collagen, so activation of the PRP occurs spontaneously when injected directly into tissues. Maintaining the PRP in an inactivated (uncoagulated) state makes syringe-based injections possible. Moreover, spontaneous activation of the PRP upon contact with the tissue results in localized growth factor release.

Although PRP has shown great promise to improve medical outcomes for a wide range of clinical applications, alternative delivery mechanisms of the PRP could greatly improve its handling properties as well as enhance its medicinal qualities. Medical field of PRP delivery relies entirely on the two techniques described above: direct injection into tissues or induced PRP activation/coagulation.

Current PRP technology has several limitations, including: the handling properties of PRP gels cannot be controlled; the physical properties of a gel formed by activation of PRP cannot be controlled; degradation rates of PRP gels cannot be controlled; release rates of biologically active components of the PRP cannot be controlled; the water content of PRP gels cannot be controlled; and immediate activation of platelets is required.

In addition to the activation of platelets by thrombin and calcium chloride, other methods are available that can also cause the release of growth factors from platelets, including the activation of granulation using PAR peptides or ADP, and lysis or disruption of platelets through chemical or mechanical means. Further, blood derived growth factors may be obtained from whole blood or other blood fractions such as serum or plasma and may also be further purified by standard biochemical methods. However, in many cases, these methods do not lead to clot formation, and thus do not provide the gelatinous material that would otherwise provide a matrix for the growth factors or a scaffold to support tissue or bone regeneration.

Furthermore, the provisional matrix (or scaffold) provided by a blood extract that would support tissue or bone regeneration may have inconsistent mechanical and/or biological properties, such as in the case of PRP, or may be incapable of formation in the case of other extracts.

For these reasons, synthetic matrices have been developed to administer blood extracts. For example, attempts have been made to deliver PRP, platelets, and platelet extracts in gelatin and alginate hydrogels, PLA/PRP gel composite scaffolds, porous PLGA/PRP gel composite scaffolds, and electrospun PRP/polymeric fiber composites. In other examples, whole blood is mixed with chitosan/glycerin phosphate or a blood extract is mixed with a peg-diacrylate scaffold. Sell, S. et al. "The Incorporation and Controlled Release of Platlet-Rich Plasma-Derived Biomolecules from Polymeric Tissue Engineering Scaffolds," *Polym. Int.* 61:1703-1709. Unfortunately, each of these methods suffers from one or more of the following limitations:

1. Inconsistent Mechanical Properties Resulting from a Reliance of the Fibrin Clot to Contribute to the Structure of the Scaffold.

As mentioned above, activation of PRP using, for example, thrombin will lead to the formation of a gelatinous gel (a clot). In traditional methods of PRP delivery, this clot serves as the scaffold for tissue or bone regeneration. However, this scaffold will have variable properties due to factors such a patient-to-patient variations and inconsistent processing techniques. To address these limitations, prior methods have augmented the clot with synthetic polymers such as PLA or PLGA. However these methods still rely on the clot to serve as a substantial component of the scaffold, which results in an improved, but still inconsistent and variable, scaffold. A fully synthetic polymer that would provide a consistent scaffold that is not reliant on the properties of the clot would be advantageous.

2. Technically Difficult Processing Techniques that May Prevent Near-Patient Processing and Application.

Some existing methods require techniques such as electrospinning of a platelet extract prior to use in an individual. These methods are time consuming, require specialized equipment, and are generally inconsistent with near-patient processing applications. A method that is rapidly performed at the site of the intended use would be beneficial.

3. Requirement For Specialized Equipment and Trained Personnel.

Even relatively simple techniques, such as the use of PRP, require specialized equipment, e.g., to separate the PRP from other components in the blood. Further, a trained transfusionist is often required to draw the blood and perform the separation. It would be desirable to have a method that uses only standard and readily available equipment and personnel that are already in place in most doctor's offices and clinics.

4. Growth Factor Release Properties that are not Responsive to the Temporal and Spatial Demands of the Tissue or Bone Regeneration Processes.

A problem with most existing methods is that upon application to an individual, the growth factors that promote tissue or bone regeneration will diffuse away from the application site (e.g., the wound) in a manner that is independent of the rate of healing. Thus, although growth factors with certain existing methods are present at the intended site at the time of initial application, they are not maintained within the desired site of action throughout the healing process, which limits the overall effectiveness of prior methods. It would be desirable to have a scaffold that retains growth factors at the desired site of action (e.g., at the wound) and releases the growth factors in response to new tissue formation.

5. Scaffold Degradation Rate not Responsive to the Tissue Regeneration Processes.

Similarly, the scaffold of certain existing methods will degrade in a manner that is independent of the rate of tissue formation. Premature degradation does not permit the injury to benefit from the scaffold throughout the healing process. It would be desirable to utilize a scaffold that degrades as new tissue is formed.

6. Inconsistent Degradation Products that May be Inefficiently Cleared.

Because certain prior methods do not have a regular, clearly defined structure, the degradation products that result from these methods are often are poorly defined and have a large size distribution. The large size distribution can present a particular problem as large degradation products may be inefficiently cleared and place an additional burden on an individual's system. A scaffold that leads to small, well defined degradation products that can be efficiently cleared would be beneficial.

7. Product does not Conform to Tissue (or Bone) Defect Resulting in Poor Integration with Native Tissue at Wound Margins.

Many of the existing products are formed outside of the tissue defect and are then cut or otherwise manipulated in an attempt to conform to the shape of the tissue defect. However, it is impossible to perform such shaping precisely enough that it fully conforms to the contours of the defect (e.g., to the shape of a wound). The resulting gaps then become an impediment to the movement into the scaffold of cells, proteins and other factors needed to facilitate tissue or bone regeneration. Moreover, gaps present an increased opportunity for bacteria or other undesirable materials to enter the defect site and lead to complications or otherwise slow or impede healing. A material that is formed in situ and more fully conforms to the shape of the tissue or bone defect (e.g., by forming a contiguous boundary with the edges of the defect) would be desirable.

8. Poor Control of Polymerization (Gelation) Process During Administration.

Certain existing methods are allowed to form a scaffold within the defect. However, these methods rely on the formation of a gelatinous clot. As previously noted, the time for clotting can be highly variable and can also lead to inconsistent results. For example, in many cases, the clotting process will have started before the material is fully administered. In other cases, the material may polymerize too slowly. A material that can be placed in the defect and then rapidly polymerized in situ using a process that provides precise temporal and spatial control would be highly beneficial.

9. Altered Activity of the Growth Factors and Other Proteins that May be Important to Tissue or Bone Regeneration.

Finally, many of the existing methods require steps that may alter the activity of growth factors in a blood extract. For example, processes that disrupt platelets through a freeze-thaw cycle or denaturation steps can substantially alter growth factor activity and lead to decreased efficacy when used in a method of tissue or bone regeneration. Similarly, methods such as electrospray fabrication can substantially alter the activity of the growth factors. A method that does not require the use of conditions that can alter the activity of growth factors or other proteins in a blood extract would be beneficial. There is thus a continued need in the art for compositions that address the limitations of current PRP and blood extract administration techniques.

SUMMARY

This disclosure provides compositions and methods for use including blood, or fractions or extracts of blood, mixed with a biomaterial. Kits comprising the compositions detailed herein and instructions for use are also provided, as are articles of manufacture comprising a composition as detailed herein. Methods of making a composition and methods of making a biomaterial as detailed herein are also provided. Importantly, the compositions and methods address one or more the disadvantages of existing technologies.

In one aspect, a composition comprising (i) a biomaterial or a precursor of a biomaterial (e.g., one or more monomer) and (ii) blood extract is provided. In one aspect, the composition comprises a polymeric biomaterial. In one aspect, the biomaterial or precursor of a biomaterial may be in a salt form. In another aspect, the biomaterial or precursor of a biomaterial may be in non-salt form. In another aspect, the composition comprises a monomer that is suitable for forming a polymeric biomaterial upon polymerization. The composition of (i) a biomaterial or a precursor of a biomaterial (e.g., one or more monomer) and (ii) blood extract may contain an additional agent, which additional agent can be an additional therapeutic agent or can be an additional agent such as a photoinitiator (such as when the composition comprises monomers suitable to form a polymeric biomaterial) or both. In one aspect, the composition comprises a polymeric biomaterial that is fully synthetic, degrades as new tissue is formed and produces defined degradation products. In another aspect, the composition comprises a polymeric biomaterial precursor (e.g., a monomer) that may be rapidly polymerized in situ (e.g., under any of about 20, 15, 10, 5, 3, 2 or 1 minutes) at the site of the defect (e.g., a wound) and, upon polymerization, produces a polymeric biomaterial that fully conforms to the shape of the defect by forming a contiguous boundary with the edges of the defect.

In certain embodiments, this blood infused biomaterial can be administered to a subject. In one embodiment, a composition comprising (i) a biomaterial and (ii) a blood extract is administered to a subject in need thereof. In another embodiment, a composition comprising (i) a biomaterial precursor (e.g., one or more monomers) and (ii) a blood extract is administered to a subject in need thereof. Suitable biomaterials and blood extracts are detailed herein. The blood can be whole blood, a fraction of blood including red blood cells, white blood cells, buffy coat, plasma or platelet rich plasma, or an extract of blood including growth factors or extracellular matrix proteins purified or released from blood or blood fractions. The biomaterial can be polymeric or non-polymeric. The biomaterial in one aspect is a step-growth polymer that is compatible with the blood extract and that can be produced (e.g., by polymerization of one or more monomers) at the site of a defect. The biomaterial may also include additives such as glycerol, poly (lactic acid) (PLA), polyglycolide (PGA), copolymers of PLA and PGA (PLGA), poly(vinyl alcohol) (PVA), poly (ethylene glycol) (PEG), poly(ethylene oxide), poly(ethylene oxide)-co-poly(propylene oxide) block copolymers (poloxamers, meroxapols), poloxamines, polyanhydrides, polyorthoesters, poly(hydroxy acids), polydioxanones, polycarbonates, polyaminocarbonates, poly(vinyl pyrrolidone), poly(ethyl oxazoline), carboxymethyl cellulose, hydroxyalkylated celluloses such as hydroxyethyl cellulose and methylhydroxypropyl cellulose, and natural polymers such as nucleic acids, polypeptides, polysaccharides or carbohydrates such as polysucrose, hyaluronic acid, dextran and similar derivatives thereof, heparan sulfate, chondroitin sulfate, heparin, or alginate, and proteins including without limitation gelatin, collagen, albumin, or ovalbumin, or copolymers, or blends thereof. Polymers include material made from one or more types of monomers.

This disclosure provides a composition comprising a blood extract (e.g., PRP) and a biomaterial (e.g., a polymeric biomaterial), wherein the blood extract is mixed with the biomaterial. In one embodiment, the biomaterial is a polymer that includes (e.g., may be produced by the polymerization of) one type of monomer. In another embodiment, the biomaterial is a polymer that comprises (e.g., may be produced by the polymerization of) at least a first and a second monomer. The first monomer can include at least one moiety capable of undergoing a free radical or nucleophilic addition reaction. This moiety can be a thiol moiety. The second monomer can include at least one reactive conjugated unsaturated group, or alkene or alkyne moiety. In a preferred embodiment, the second monomer comprises a norbornene (e.g., the monomer is derivatized with norbornene). The first and/or second monomers may be derivatized to include a thiol, alkene or alkyne moiety. In one aspect, the first monomer comprises a thiol moiety and the second monomer comprises an alkene or alkyne moiety, such as a monomer comprising a norbornene moiety.

In certain embodiments, the first and second monomer are joined (polymerized) through a chemistry that supports the formation of step growth networks, such as free radical thiol-ene or thiol-yne chemistry, nucleophilic addition, or other click chemistries. In a preferred embodiment, the chemistry is free-radical thiol-ene chemistry. A product produced by a process, such as a chemistry, detailed herein is also provided.

A monomer for use herein may comprise a polymeric unit, provided that the monomer is suitable for further polymerization, such as by the presence of functional groups that may react with mutually reactive functional groups on the same or another monomer. It is thus understood that the monomers detailed herein and below may be derivatized to include a functional group (e.g., a functional group that is mutually reactive with a functional group on another monomer, which may be the same or different). For example, a thiol functional group is mutually reactive with an ene functional group and it is understood that a first monomer detailed herein may be derivatized to include a thiol functional group and a second monomer detailed herein may be derivatized to include an ene functional group such that a polymer may be formed by reacting the first monomer comprising a thiol functional group with a second monomer comprising an ene functional group. In one aspect, a monomer is derivatized with a functional group at a termini of the monomer (e.g., at a terminus of a PEG monomer). Further, it is understood that a linking group may be used to link the monomer to the functional group. In one aspect, a linking group is selected that provides an ester or an amide linkage. Monomers may be derivatized according to known chemical reactions and under standard reaction conditions, including those provided herein. For example, in certain embodiments, the first and/or second monomer is selected from the group consisting of poly(lactic acid) (PLA), polyglycolide (PGA), copolymers of PLA and PGA (PLGA), poly(vinyl alcohol) (PVA), poly(ethylene glycol) (PEG), poly(ethylene oxide), poly(ethylene oxide)-co-poly(propylene oxide) block copolymers (poloxamers, meroxapols), poloxamines, polyanhydrides, polyorthoesters, poly(hydroxy acids), polydioxanones, polycarbonates, polyaminocarbonates, poly(vinyl pyrrolidone), poly(ethyl oxazoline), carboxymethyl cellulose, hydroxyalkylated celluloses such as hydroxyethyl cellulose and methylhydroxypropyl cellulose, and natural polymers such as nucleic acids, polypeptides, polysaccharides or carbohydrates such as polysucrose, hyaluronic acid, dextran and similar derivatives thereof, heparan sulfate, chondroitin sulfate, heparin, or alginate, and proteins including without limitation gelatin, collagen, albumin, or ovalbumin, or copolymers, or blends thereof. In particularly preferred embodiments, the monomers can be selected from poly(lactic acid) (PLA), poly(vinyl alcohol) (PVA), and poly(ethylene glycol) (PEG). The monomers above may be derivatized to include a functional group. Thus, the monomers above may be modified by introducing via a linking moiety, such as an amide or an ester bond, a functional group that is mutually reactive with another functionality, for example, with a thiol group.

In certain embodiments, the polymer forms a hydrogel. Thus, hydrogel biomaterials may be used in the methods detailed herein and polymeric biomaterial precursors (e.g., monomers) upon polymerization may provide a polymeric biomaterial hydrogel. The hydrogel can include more than 50% solvent by weight. Optionally, the hydrogel can include between about 50% and about 95% water by weight. In a preferred embodiment, the hydrogel includes greater than 95% water by weight, such as a hydrogel comprising about 96% or 98% water by weight.

In one variation, a polymeric biomaterial detailed herein exhibits one or more of the following attributes: (a) the polymeric biomaterial is a fully synthetic, consistent and reproducible scaffold for tissue or bone repair that is not reliant on the properties of a clot; (b) the polymeric biomaterial is capable of releasing growth factors at the desired site of action (e.g., at the wound or damaged bone) throughout the healing process; (c) the polymeric biomaterial degrades as new tissue or bone is formed; (d) the polymeric material produces well defined degradation products in vivo; (e) the polymeric biomaterial is capable of being rapidly formed in situ and (f) when produced in situ (such as at the site of the defect) the polymeric biomaterial forms a contiguous boundary with the edges of the defect.

In another embodiment, the first or second monomers are degradable. The degradable monomer can be hydrolytically, chemically, or enzymatically degradable. In certain embodiments, the first monomer includes a peptide. The peptide can be enzymatically degradable. In a preferred embodiment, the enzyme can be a protease, where the protease may be released by cells that participate in the repair (e.g., tissue or bone regeneration) of the defect.

In another embodiment, a composition as detailed herein may also include an additional agent that has a biological function or activity. The additional agent may be either covalently linked into the polymeric biomaterial or may be non-covalently held within the polymeric biomaterial. A composition is provided wherein the composition comprises (i) a biomaterial or a precursor to a biomaterial (e.g., one or more monomers); (ii) a blood extract and (iii) an additional agent (which may be an additional therapeutic agent or may be an additional agent such as a photoinitiator (such as when the composition comprises monomers suitable to form a polymeric biomaterial). In one aspect, more than one additional agents are present in a composition, such as a composition comprising (i) a biomaterial or a precursor to a biomaterial; (ii) a first additional agent (e.g., an additional therapeutic agent) and (iii) a second additional agent (e.g., a photoinitiator), wherein the composition may optionally comprise a blood extract. Also provided herein is a composition comprising (i) a biomaterial or a precursor to a biomaterial (e.g., one or more monomer) and (ii) an additional agent which may be an additional therapeutic agent or may be an additional agent such as a photoinitiator (such as when the composition comprises monomers suitable to form a polymeric biomaterial). In one aspect, such a composition comprises a polymeric biomaterial. In another aspect, such a composition comprises a precursor to a polymeric biomaterial, such as one or more monomers that, upon polymerization, form a polymeric biomaterial. In a further variation, such a composition comprises a first and a second monomer, wherein the first monomer comprises a thiol moiety and the second monomer comprises an alkene or an alkyne moiety and where the first and the second monomer are precursors to a polymeric biomaterial comprising an organosulfur moiety (e.g., a moiety that comprises —C—S—C). The agent (the additional agent) can be a peptide selected from adhesion peptides (such as RGD adhesion sequence), growth factors, hormones, anti-hormones, signaling compounds, enzymes, serum proteins, albumins, macroglobulins, globulins, agglutinins, lectins, extracellular matrix proteins, antibodies, and antigens. In one aspect of the compositions detailed herein, the compositions contain the RGD adhesion sequence. In one implementation, the RGD sequence is covalently attached to the polymer through an added cysteine residue. In another aspect of the compositions detailed herein, the compositions do not contain the RGD adhesion sequence. Types of non-peptide agents that can be incorporated into the polymeric material include analgesics, antipyretics, nonsteriodal anti-inflammatory drugs, anti-allergics, antibacterial drugs, antifungal, antimicrobial, anti-anemia drugs, cytotoxic drugs, anti-hypertensive drugs, dermatological drugs, psychotherapeutic drugs, vitamins, minerals, anorexiants, dietetics, anti-adiposity drugs, carbohydrate metabolism drugs, protein metabolism drugs, thyroid drugs, anti-thyroid drugs, and coenzymes.

In another embodiment, the blood extract (e.g., PRP) comprises at least 1000 or at least $1 \times 10^9$ platelets. Optionally, the platelets are not substantially activated. Thus, less than 50% or 10% of the platelets in the blood extract (e.g., PRP) can be activated. In preferred embodiments, the blood extract is either serum or plasma in which platelets have been activated.

This disclosure also provides a method of delivering a blood extract to a subject in need thereof comprising providing a blood extract; providing a one or more monomers; mixing the blood extract with the one or more monomers; polymerizing the one or more monomers to form a polymer, wherein the blood extract is integrated within the polymer, and administering the polymer to the subject in need thereof. In certain embodiments, the biomaterial is polymerized after the monomers have been placed at the site of the defect. The one or more monomers can include a first and a second monomer. The first monomer can include at least one moiety capable of undergoing a free radical or nucleophilic addition reaction. The first monomer can include at least two moieties capable of undergoing a free radical or nucleophilic addition reaction. The first monomer can include at least one or preferably at least two moieties that can be a thiol moiety. The second monomer can include at least one reactive conjugated unsaturated group, or alkene or alkyne moiety. The first and/or second monomer is in one aspect derivatized to include a thiol, alkene or alkyne moiety. In one aspect, a first monomer comprises a thiol moiety and a second monomer comprises an alkene or alkyne moiety.

A method of administering a blood extract to a damaged site (or defect) in an individual is provided, wherein the method comprises delivering to the damaged site a composition comprising (i) a biomaterial or a precursor to a biomaterial and (ii) a blood extract. In one aspect, the damaged area is a wound. In another aspect, the damaged area is damaged bone. In one aspect, the individual is a human. In one variation of the method, a polymeric biomaterial is delivered to the damaged area. In a further aspect of the method, the polymeric biomaterial delivered to the damaged area comprises an organosulfur moiety (e.g., —C—S—C—). In another variation of the method, a precursor to a polymeric biomaterial, such as one or more monomers (which may be the same or different) is delivered to the damaged area and the polymeric biomaterial is produced in situ from the precursor. Thus, in one aspect of a method that utilizes delivery of a precursor to a polymeric biomaterial (e.g., delivery of one or more monomers), the method further comprises polymerizing the precursor in situ at the damaged site. In another variation of the method, a precursor to a polymeric biomaterial, such as one or more monomers (which may be the same or different) is delivered to the damaged area in combination with a blood extract, and the polymeric biomaterial is produced in situ from the precursor. When delivered in combination with a blood extract, the method may comprise delivering the precursor to a polymeric biomaterial concurrently with the blood extract, e.g., by mixing the precursor with the blood extract and delivering the mixture to the individual (e.g., to the damaged site, such as a wound). When delivered in combination with a blood extract, the method may also comprise delivering to an individual (e.g., to the damaged site of an individual, such as a wound) the precursor to a polymeric biomaterial prior to or after delivery of a blood extract to the individual (e.g., to the damaged site of an individual, such as a wound), wherein the precursor and the blood extract are administered to the individual no more than about any of 60, 45, 30, 25, 20, 15, 10, 5, 3 or 2 minutes apart. In yet another aspect of the method, the precursor to a polymeric biomaterial that is delivered to the damaged area comprises a first monomer having a thiol moiety and a second monomer having an alkene or alkyne moiety. In one aspect of such a method, the first monomer comprising a thiol moiety is a monomer comprising a cysteine residue, such as a moiety comprising a peptide in which a cysteine residue is included (e.g., a di-cysteine MMP-degradable peptide), and the second monomer is a monomer comprising a norbornene moiety, such as a PEG monomer derivatized with norbornene. In any of these methods, in one aspect, the method has one or more of the following attributes: (a) the method is rapidly performed at the site of the intended use; (b) the method uses only standard and readily available equipment and personnel; and (c) the method does not require the use of conditions that can substantially alter the activity of growth factors or other proteins in a blood extract.

In certain embodiments, the first and second monomer are joined through a chemistry that supports the formation of a step growth networks, such as free radical thiol-ene or thiol-yne chemistry, nucleophilic addition, or other click chemistries. In a preferred embodiment, the chemistry is free-radical thiol-ene chemistry. Biomaterials produced by such chemistries are also provided.

In one embodiment, the first and/or second monomer is selected from the group consisting of poly(lactic acid) (PLA), polyglycolide (PGA), copolymers of PLA and PGA (PLGA), poly(vinyl alcohol) (PVA), poly(ethylene glycol) (PEG), poly(ethylene oxide), poly(ethylene oxide)-co-poly (propylene oxide) block copolymers (poloxamers, meroxapols), poloxamines, polyanhydrides, polyorthoesters, poly (hydroxy acids), polydioxanones, polycarbonates, polyaminocarbonates, poly(vinyl pyrrolidone), poly(ethyl oxazoline), carboxymethyl cellulose, hydroxyalkylated celluloses such as hydroxyethyl cellulose and methylhydroxypropyl cellulose, and natural polymers such as nucleic acids, polypeptides, polysaccharides or carbohydrates such as polysucrose, hyaluronic acid, dextran and similar derivatives thereof, heparan sulfate, chondroitin sulfate, heparin, or alginate, and proteins including without limitation gelatin, collagen, albumin, or ovalbumin, or copolymers, or blends thereof. In particularly preferred embodiments, the monomers can be selected from poly(lactic acid) (PLA), poly(vinyl alcohol) (PVA), and poly(ethylene glycol) (PEG). In one aspect, a monomer detailed above is derivatized to include a functional group that is mutually reactive with a thiol functional group. In one aspect, a monomer detailed above is derivatized to include an ene or yne functional group.

In certain embodiments, the polymer forms a hydrogel. The hydrogel can include more than 50% solvent by weight. Optionally, the hydrogel includes between 50 and 95% water by weight. In another embodiment, the hydrogel includes between 95% and 99% water by weight. In a preferred embodiment, the hydrogel includes greater than 95% water by weight. In a preferred embodiment, the hydrogel includes greater than 95% water by weight, such as a hydrogel comprising about 96% or 98% water by weight.

In another embodiment, the first or second monomers are degradable. The degradable monomer can be hydrolytically, chemically or enzymatically degradable. In one aspect, the first monomer comprises a peptide. The peptide can be enzymatically degradable. In a preferred embodiment, the enzyme is a protease, where this protease is released by cells that participate in the repair of the defect.

In another embodiment, the polymerization step further includes the addition of a photoinitiator, a chemical initiator, or both a photoinitiator and a chemical initiator. The photoinitiator can be selected from Irgacure 2959, Irgacure 184, Irgacure 651, LiAP (LAP) and NaAP. The chemical initiator can be selected from glucose with glucose oxidase, TEMED with APS, or Horseradish (HRP) or Soybean (SBP) with peroxide substrates (ROOH).

In another embodiment, the polymerization step further includes exposing the first and second monomers to light. The light can be selected from infrared, ultraviolet and visible light. In certain embodiments, the light is ultraviolet light. The ultraviolet light can have a wavelength between 300 and 400 nm. In one aspect the light source is a dental light. In a preferred embodiment, the wavelength is selected such that it is within the absorption spectrum of an added photoinitiator. In another aspect, the exposure lasts for less than one, two, five or 20 minutes. The polymerization may occur either before or after the monomers are administered to the patient.

This disclosure also provides a method of treating a skin wound, orthopedic condition, pain, nerve injury, tendinitis, osteoarthritis, cardiac muscle injury, bone injury, traumatic injury or dental injury comprising administering to a subject in need thereof any of the compositions described above. The compositions and methods may also be used in the context of treating a sports injury, bone repair and regeneration (e.g., healing an injured bone) and in aiding recovery from plastic surgery (e.g., healing post-surgical wounds).

The disclosure also provides a method of treating skin wounds, orthopedic conditions, pain, nerve injury, tendinitis, osteoarthritis, cardiac muscle injury, bone injury, traumatic injury or dental injury including the steps of administering to a subject in need thereof one or more monomers mixed with a blood extract; and polymerizing the monomers to form a polymer; thereby treating the subject in need thereof.

In one embodiment, the polymerization step further includes the addition of a photoinitiator. The photoinitiator can be selected from Irgacure 2959, Irgacure 184, Irgacure 651, LiAP and NaAP.

In another embodiment, the polymerization step further includes exposing the one or more monomers to light. The light is selected from infrared, ultraviolet and visible light. In a specific embodiment, the light is ultraviolet light. The ultraviolet light can have a wavelength between 300 and 400 nm. In one aspect the light source is a dental light. In a preferred embodiment, the wavelength is selected such that it is within the absorption spectrum of an added photoinitiator. In another aspect, the exposure can last for less than one, two, five or 20 minutes. The polymerization may occur either before or after the monomers are administered to the patient.

The disclosure also provides a method of slowing the activation of a blood extract administered to a subject in need thereof including administering to a subject in need thereof any of the compositions described above.

The disclosure also provides a kit including any of the compositions described above and instructions for use in a method detailed herein. In one aspect of the kits, a container comprising a polymeric biomaterial or a precursor to a polymeric biomaterial is packaged with a second container suitable for obtaining or storing a blood extract from an individual. A method of delivering a blood extract obtained from an individual by collection of the blood extract into the vacutainer is also provided wherein the blood extract contained within the vacutainer is delivered back to the individual from which the blood extract was obtained. In one embodiment, the kit also includes a photoinitiator. Articles of manufacture comprising a polymeric biomaterial or a precursor to a polymeric biomaterial (e.g., monomers) are also provided.

BRIEF DESCRIPTION OF THE FIGURES

FIG. 4(A) shows that by varying the concentration of PEG monomers in the network, scaffolds can be produced that range in stiffness from very soft to very stiff. FIG. 4(B) illustrates that networks with varying mechano-elastic properties can be produced by varying the ratio of branched to linear PEG monomers resulting in networks with different pore size.

FIG. 11(A) shows that reducing the overall weight percent of PEG in the solution reduces aggregation. FIG. 11(B) shows that depletion of growth factors, exemplified by PDGF-BB, by treatment with PEGs of various molecular weights from extracts prepared form concentrated platelets.

FIG. 14(A) shows a 4-arm PEG-norbornene with the ester linkage. Fully functionalized 4-arm PEGs will have four terminal Norbornenes (NB). FIG. 14(B) illustrates that functionalization of PEGs with norbornene can be accomplished with different chemistries that result in distinct linkages. Ester and amide linkages are shown as examples.

DETAILED DESCRIPTION

Figure 1:
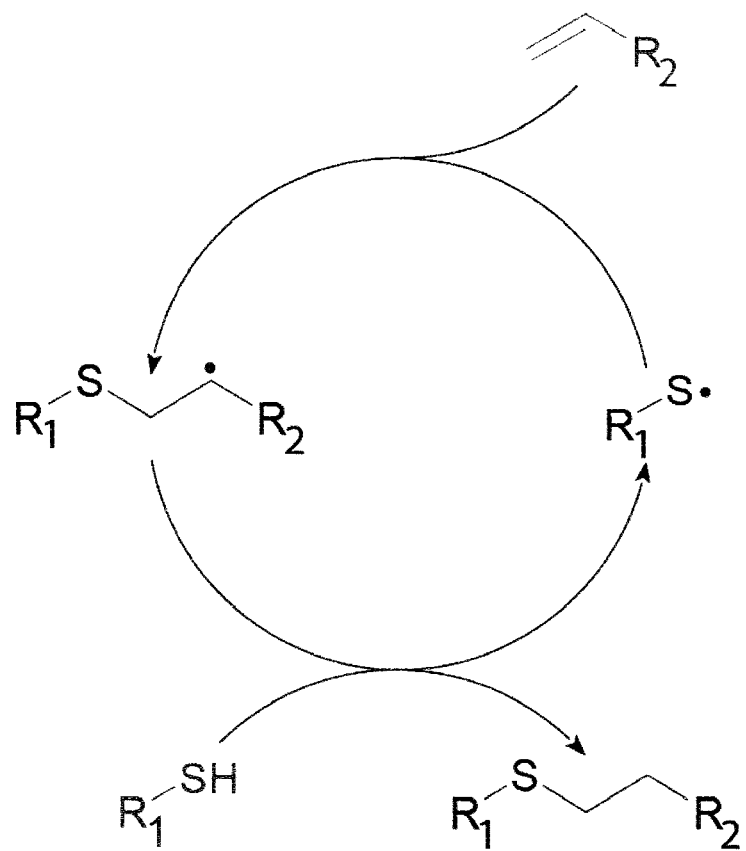
FIG. 1 is a schematic diagram illustrating the general mechanism of a thiol-ene reaction involving the addition of an S—H bond across a double bond by a free radical.
Figure 2:
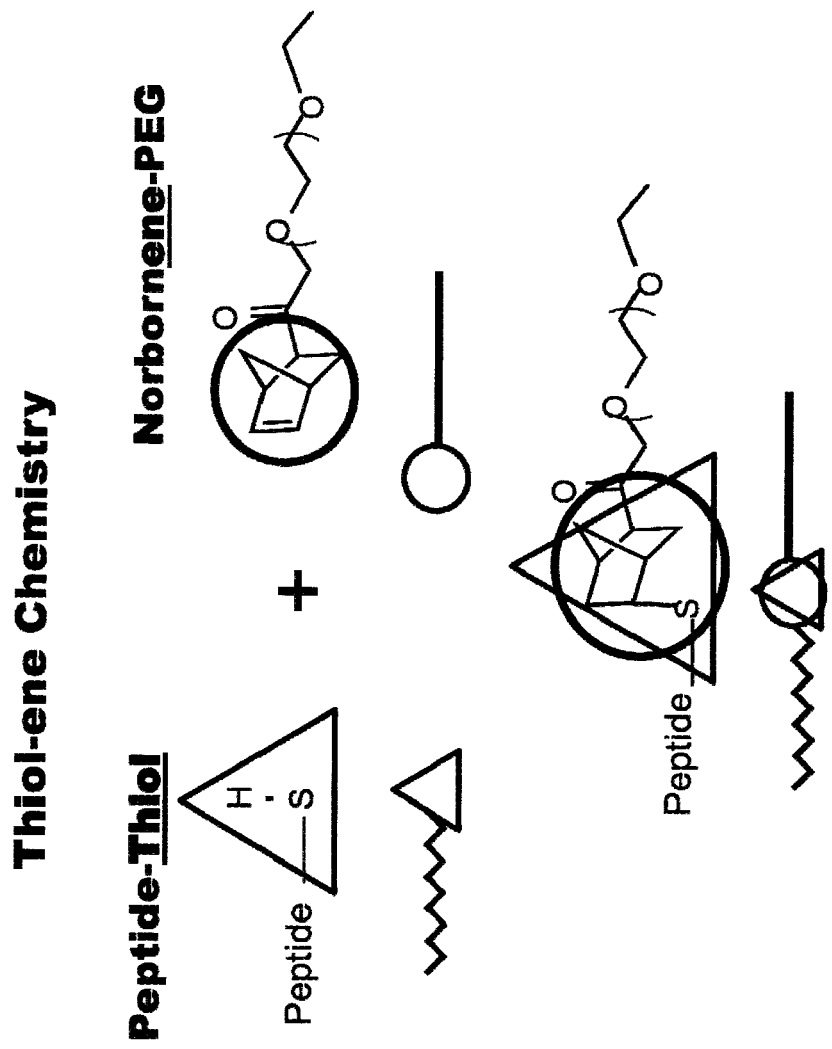
FIG. 2 illustrates thiol-ene chemistry between mutually reactive monomers. A cysteine-containing peptide (thiol source indicated by a triangle) and PEG-norbornene monomers (norbornene source indicated by a circle) undergo a thiol-ene reaction resulting in crosslinking of PEG monomers to the peptide.
Figure 3:
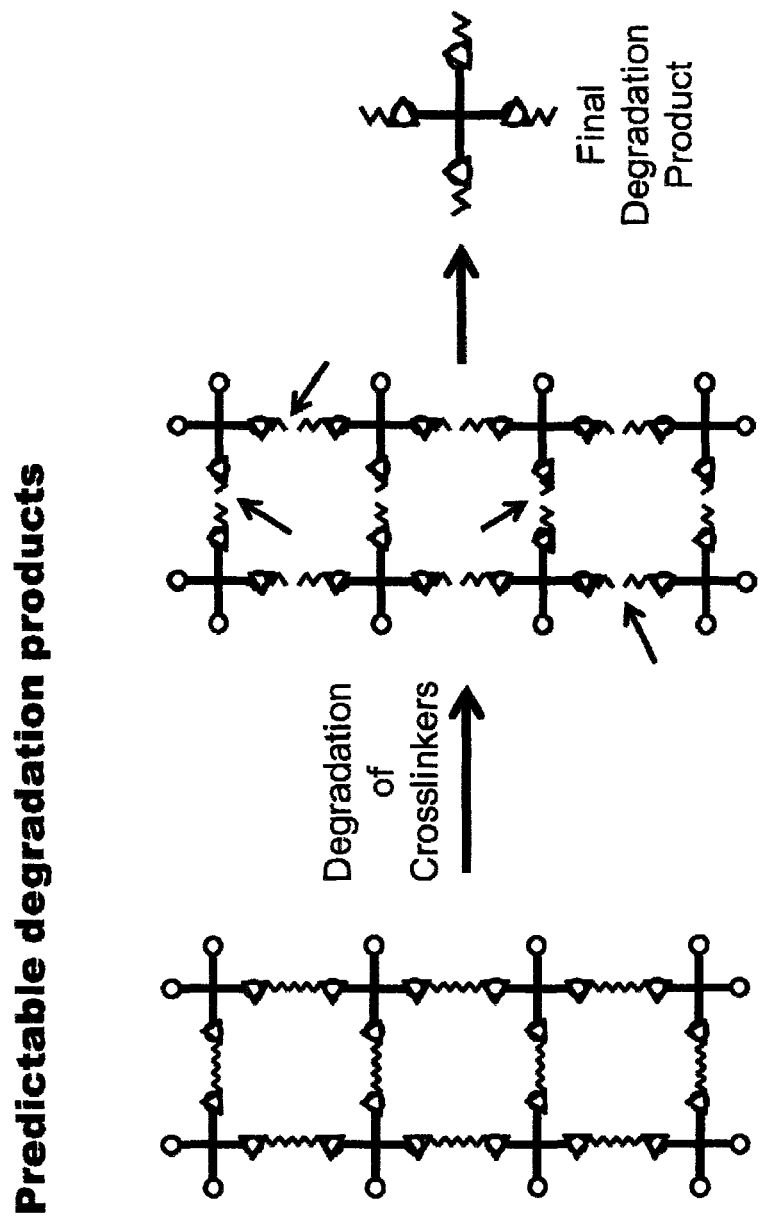
FIG. 3 illustrates that step-growth networks produce predictable degradation products. A network formed by step-growth thiol-ene chemistry undergoes degradation by enzymatic cleavage at specific di-thiol enzymatically degradable peptide crosslinks producing predictable degradation products.
Figure 4:
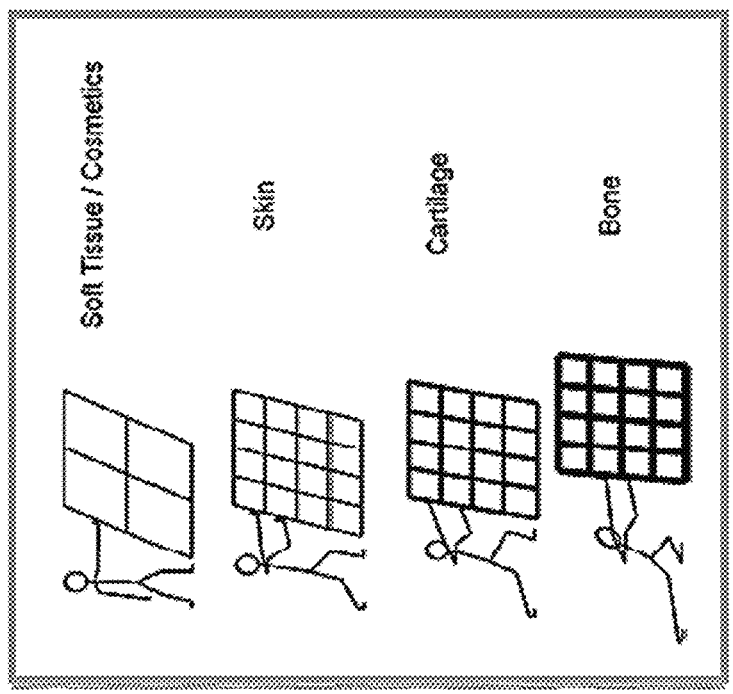
FIG. 4 illustrates that thiol-ene hydrogels can be manufactured with specific mechano-elastic properties.
Figure 4:
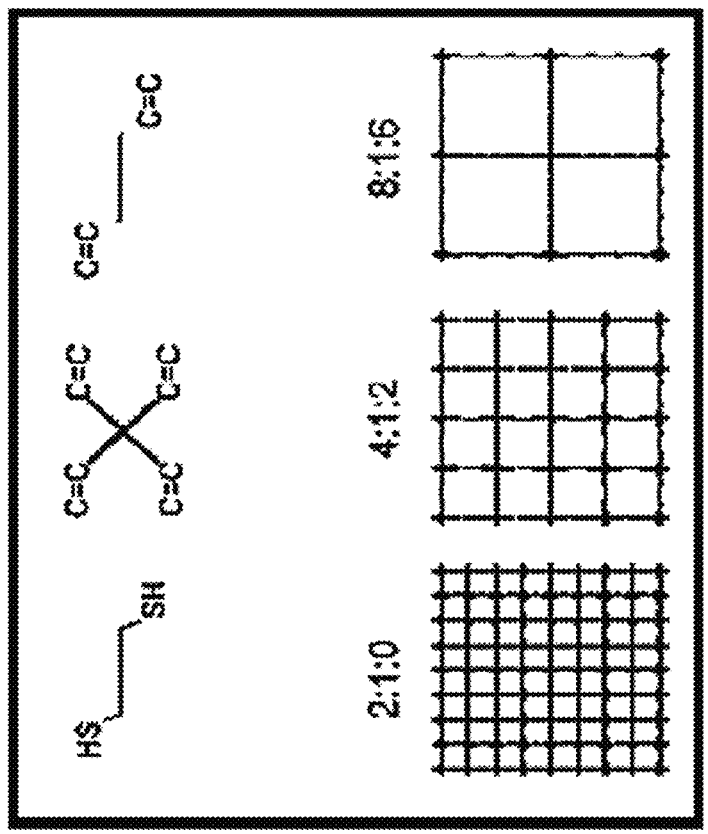
Figure 5:
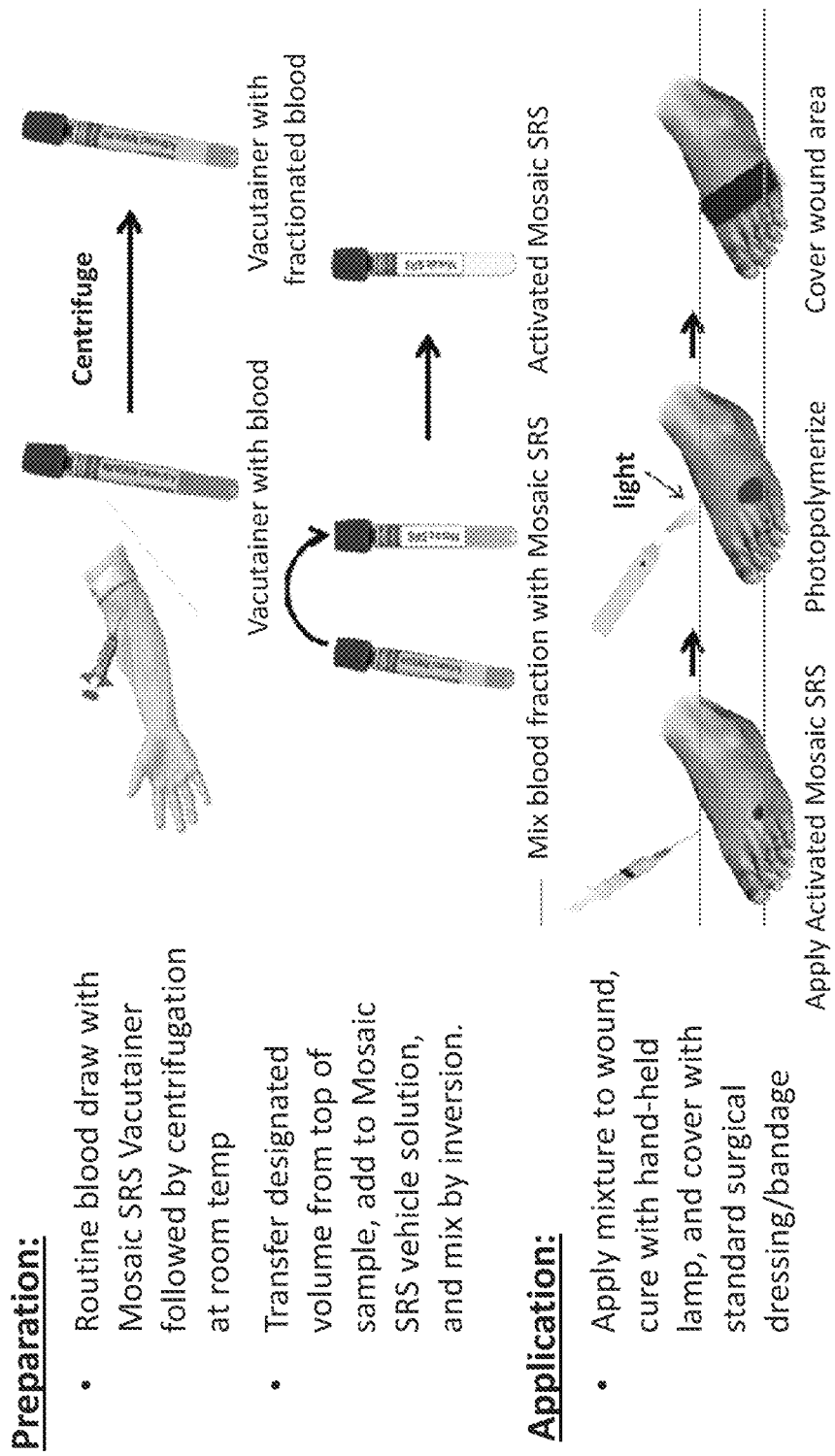
FIG. 5 is a depiction of an application of a composition comprising a biomaterial and a blood extract to the treatment of a wound. A vacutainer for the activation of whole blood, the biomaterials, and disposables are depicted. A routine blood draw is performed and the activated blood is fractioned by centrifugation. The activated blood extract is mixed with a biomaterial precursor (e.g., one or more monomers). The mixture is then applied to a wound, polymerized with a handheld lamp, and the wound area is bandaged with standard wound dressings.

The disclosure provides biomaterials including scaffolds and hydrogels that are mixed with whole blood, or fractions or extracts of blood. The blood extract infused biomaterials can then be administered to subjects in need thereof. The fractions of blood include red blood cells, white blood cells, buffy coat, plasma or platelet rich plasma, or an extract of blood including growth factors, extracellular matrix proteins, or other proteins purified or released from blood or blood fractions. In certain embodiments, the fraction of blood that is used includes platelets. The combination of platelets with the biomaterial allows for control over the timing of activation of the platelets. In certain embodiments, the timing of platelet activation can be delayed until sometime after administration to a subject. In another specific embodiment, the platelets are provided from platelet rich plasma (PRP).

The compositions and methods detailed herein are an advance over existing compositions and methods for use e.g., in treating a tissue or bone defect in an individual. Specifically, (i) biomaterials provided herein (e.g., PEG based polymers) have reproducible and precisely defined mechanical properties; (ii) blood extracts for use herein are quickly and easily processed and can be performed in near-patient settings; (iii) preparation of the compositions and blood extracts can be performed without special equipment or training; (iv) enzymatically degradable biomaterials are provided (e.g., step growth network) that release growth factors in response to naturally occurring cellular processes involved in tissue regeneration and repair; (v) biomaterials provided herein (e.g., enzymatically degradable, step growth networks) degrade in response to the generation of new tissue; (vi) biomaterials provided herein (e.g., enzymatically degradable, step growth networks) yield in vivo degradation products of uniform size that can be efficiently cleared; (vii) polymerization at the site of the defect results in a perfect fit of the resultant polymer to the shape of the defect; (viii) polymeric biomaterials provided herein (e.g., thiol-ene and thiol-yne based photopolymerization) provide rapid and precise control of the polymerization process; (ix) no processing steps are used that will substantially alter the activity of growth factors.

Certain compositions for use herein contain a biopolymer or biopolymer precursors and a blood extract. A biopolymer for use herein may in one aspect be a step growth biopolymer which may be used in conjunction with a blood extract containing the necessary growth factors and scaffolding components to support tissue regeneration. Step growth polymers provided herein have particular advantages, including controlled polymerization and degradation properties with reproducible mechanical properties. In one aspect, a step growth polymer for use herein is based on a PEG first monomer (e.g., PEG-norbornene such as a 4-arm 2k PEG norbornene) and an enzymatically degradable second monomer (which may be a cross-linker such as a protease degradable linker). Polymer biomaterials are thus provided in which the monomeric components of the polymer may be cross-linked by enzymatically degradable moieties, such as a peptide that is cleaved by a protease released by the appropriate cell type for tissue regeneration, which provides appropriate release of growth factors when used in vivo. Biopolymers herein (e.g., step growth polymers) may also have mechanical properties tuned to a specific application. Moreover, biopolymer precursors may be selected and used at concentrations that do not precipitate or otherwise alter the activity of a blood extract, which is an important consideration where a composition comprising a biopolymer precursor (e.g., monomers) are mixed with a blood extract and polymerized in situ at the site of the defect (e.g., at the wound). It is also understood that the polymeric biopolymers provided herein (e.g., step growth polymers) may be rapidly polymerized at the site of administration, which polymerization may be accomplished where applicable through a photo-initiated free radical reaction, a chemically initiated free radical reaction, or both a photo-initiated free radical reaction and a chemically initiated free radical reaction.

The aforementioned benefits are applicable to compositions and methods involving a step growth polymer. That is, by the combination of a) an inert polymer backbone; b) an enzymatically degradable peptide sequence; c) a resultant polymer that is a step growth polymer; d) a blood extract that contains either platelets and/or a platelet extract; and e) rapid and precisely controlled polymerization at the site of the defect, particular benefits have been achieved that have not been exemplified by existing compositions and methods.

The use of engineered biomaterials to improve the delivery of blood extracts can significantly enhance their efficacy in medical applications. Advances in biomaterial technologies can be used to create specific carriers/adjuncts for blood extracts that provide additional benefits and capacities. These benefits include, but are not be limited to, improved handling properties, degradation rates, growth factor release profiles and tissue scaffolding properties.

This disclosure provides biomaterial carriers/adjuncts that provide improved handling properties for medical procedures in which blood extracts are used. In one embodiment, the biomaterial carrier/adjunct is used with PRP to increase the stiffness of activated PRP gels that are formed before implantation to facilitate transfers to a surgical site. In another embodiment, a photo-initiated biopolymer is used to provide additional control of blood extract localization at the desired site of application. In this embodiment, a blood extract is premixed with a monomer solution, applied to the desired site, and then polymerized in place with light. This allows for continued handling of the materials until satisfied with its placement, at which time polymerization would effectively prevent movement.

This disclosure also provides biomaterial carriers/adjuncts that overcome limitations of current techniques to control the placement and localization of blood extracts to enhance medical outcomes. In one embodiment, a mixture of a blood extract with an engineered carrier that provides a malleable, putty-like consistency is used to improve pre- and post-implantation shaping for better localization at a wound or surgical site. In another embodiment, a photo-initiated biopolymer is used, as described above, to provide additional control of blood extract localization at the desired site of application.

The physical properties of activated PRP or other blood extracts are limited. This disclosure provides biomaterial carriers/adjuncts that better support appropriate physical properties for individual applications would improve medical outcomes. In one embodiment, biomaterials that provide physical properties similar to those found in the skin are used for skin wound healing applications. That carrier/adjunct increases elasticity, water retention, etc. In another embodiment, a blood extract carrier/adjunct that significantly increases the stiffness of the delivered material is used to supply important physical strength for applications involving bone and/or cartilage.

Using previous methods for the administration of PRP, fibrin clots degrade quickly, reducing the duration of PRP activity since the biologically active components of the PRP are subsequently released to the surrounding tissues. Although this is the intended mechanism of action of the PRP, current clinical techniques do not provide a means to reliably control the rate of delivery of these factors. This disclosure also provides a biomaterial carrier/adjunct with a mechanism to either slow or increase the rate of release. In one embodiment, a polymer system in which the monomers can be pre-mixed with the PRP and then polymerized effectively encapsulates the PRP within the polymer matrix. Optionally, the polymer can be designed in such a way that it contains degradable moieties (enzymatic, hydrolytic, etc.), such that the polymer will degrade at a rate that is dictated by these moieties. As such, the release of the biologically active components of the PRP is dictated/affected by the rate of degradation of the polymer matrix. In this embodiment, the rate of material degradation is tuned to have release rates that are optimal for biological activity of the PRP. In another embodiment, a carrier/adjunct that acts to bind critical growth factors a blood extract and slow their release into the surrounding is used to improve the therapeutic properties of the blood extract.

Current delivery mechanisms of PRP rely on platelet activation in order to form a clot. This disclosure also provides a material carrier/adjunct that is able to deliver concentrated platelets without activating them to provide a mechanism for delayed release of biologically active components. By delaying platelet activation, a prolonged factor release could be achieved. An added benefit of an approach that delays platelet activation is that it avoids the use of bovine thrombin, which can elicit immune responses and reduce PRP efficacy. In one embodiment, a carrier/adjunct material that is mixed with PRP before injection provides a mechanism to prevent initial platelet contact with tissues that effectively delays platelet activation and release of biologically active factors. In such a system, slow degradation and/or infiltration of cells from surrounding tissues would cause a delay in the presentation of signals that activate platelets. The result is a slowed and sustained release of biologically active factors.

In one embodiment, the monomers of a polymer-based system could be pre-mixed with non-activated platelets, PRP, or other blood extract. Polymerization of the material either before implantation or in situ provides a mechanism to deliver the platelets without prior activation and coagulation. As such, the blood extract stably retain the biological factors until the polymer is degraded and/or cells infiltrate into the matrices. The result is a slowed and sustained release of biologically active factors.

Improved release kinetics (described above) can result in a reduction in the volumes of blood needed to achieve the same therapeutic outcome. In addition to serving as a filler when large volumes of material are needed to fill defects, carriers/adjuncts increase blood extract efficacy, effectively lowering the therapeutic doses required for each application. For large wounds and patients with limited platelet counts or a limited ability to draw blood, a material carrier/adjunct that improves the efficiency of the blood extract available provides a significant advantage. In one embodiment, in order to fill a large diabetic foot ulcer, volume limitations prevent medical professionals from being able to completely fill the defect with PRP or other blood extracts. A carrier is used that increases the volume of the material without decreasing the therapeutic efficacy. In another embodiment, for burn wounds that cover large areas of the skin, a carrier/adjunct is provided that increased the total volume and allowed for increase wound coverage without significantly decreasing efficacy.

Compositions

In one aspect, a composition comprising (i) a biomaterial or a precursor of a biomaterial (e.g., one or more monomers) and (ii) a blood extract is provided. In one aspect, the composition comprises a polymeric biomaterial. In another aspect, the composition comprises a monomer that is suitable for forming a polymeric biomaterial upon polymerization. The composition of (i) a biomaterial or a precursor of a biomaterial (e.g., one or more monomer) and (ii) blood extract may contain an additional agent, which additional agent can be an additional therapeutic agent or can be an additional agent such as a photoinitiator (such as when the composition comprises monomers suitable to form a polymeric biomaterial) or both. In one aspect, the composition comprises a polymeric biomaterial that is fully synthetic, degrades as new tissue is formed and produces defined degradation products. In another aspect, the composition comprises a polymeric biomaterial precursor (e.g., a monomer) that may be rapidly polymerized in situ (e.g., under any of about 20, 15, 10, 5, 2, or 1 minutes) at the site of the defect (e.g., a wound) and, upon polymerization, produces a polymeric biomaterial that fully conforms to the shape of the defect by forming a contiguous boundary with the edges of the defect.

In one aspect, a composition comprising (i) a biomaterial precursor (e.g., one or more monomers) and (ii) a blood extract is provided. The biomaterial precursors may be monomers that, upon polymerization, provide a polymeric biomaterial. In a particular variation, the biomaterial precursors are monomers that, upon polymerization, provide a step-growth polymeric biopolymer. In a particular variation, the biomaterial precursors comprise a PEG first monomer (e.g., PEG-norbornene such as a 4-arm PEG norbornene) and an enzymatically degradable second monomer (which may be a cross-linker such as a protease degradable linker comprising a peptide). In a particular variation, the biomaterial precursors comprise a derivatized PEG first monomer (e.g., PEG-norbornene such as a 4-arm 2k PEG norbornene) and an enzymatically degradable second monomer (which may be a cross-linker such as a protease degradable linker comprising a peptide). Preferably, the biomaterial precursor does not adversely affect the blood extract. The biomaterial precursor in one variation comprises any biomaterial precursor detailed herein, including the Polymer Systems and Properties section and elsewhere. In one aspect, the biomaterial precursor is used at concentrations that do not precipitate or otherwise substantially alter the activity of a blood extract.

A composition comprising (i) a biomaterial precursor (e.g., one or more monomers) and (ii) a blood extract may further comprise one or more additional agents, which may be an additional therapeutic agent. A composition comprising (i) a biomaterial precursor (e.g., one or more monomers) and (ii) a blood extract may further comprise a carrier, such as an aqueous carrier. Compositions comprising (i) a biomaterial precursor (e.g., one or more monomers) and (ii) a blood extract and (iii) an aqueous carrier may, upon polymerization, provide a polymeric biomaterial hydrogel containing a blood extracted mixed therein. In one aspect, the carrier is a sterile aqueous carrier. In another aspect, the carrier may contain an additional agent that changes the handling properties of the pre-polymerized material.

In one aspect, a composition comprising (i) a polymeric biomaterial (e.g., a polymeric step-growth biomaterial) and (ii) a blood extract is provided. In a particular variation, the polymeric biomaterial comprises a PEG moiety (e.g., derived from a PEG-norbornene monomer such as a 4-arm 2k PEG norbornene) and an enzymatically degradable moiety (e.g., a protease degradable linker moiety such as a peptide). The polymeric biomaterial in one variation comprises any polymeric biomaterial detailed herein, including the Polymer Systems and Properties section and elsewhere.

A composition comprising (i) a polymeric biomaterial and (ii) a blood extract may further comprise one or more additional agents, which may be an additional therapeutic agent. A composition comprising (i) a polymeric biomaterial and (ii) a blood extract may further comprise a carrier, such as an aqueous carrier. In one aspect, the carrier is a sterile aqueous carrier. In any of the compositions comprising a biomaterial or precursor thereof, in one aspect the composition further comprises a carrier, which may be a pharmaceutically acceptable carrier. In one aspect, the carrier is an aqueous carrier, such as a sterile aqueous carrier. In another aspect, the carrier may contain an additional agent that changes the handling properties of the pre-polymerized material.

Particular compositions comprising a biomaterial include those in which the biomaterial is a polymeric biomaterial. In one aspect, the polymeric biomaterial comprises an enzymatically degradable moiety, such as a peptide moiety. In another aspect, the polymeric biomaterial comprises an enzymatically degradable moiety, such as a peptide, and a moiety derived from norbornene (e.g., a moiety derived from the reaction of a thiol on a peptide with the ene functionality of norbornene). A composition may comprise any biomaterial provided herein, including polymeric biomaterials detailed throughout and in the accompanying examples.

Particular compositions comprising a precursor to a biomaterial include a composition comprising a PEG monomer and an enzymatically degradable peptide monomer. These monomers in one variation are each derivatized such that the monomers can form a polymer via a step-growth mechanism, thereby forming a step growth polymer. These monomers may be are contained within an aqueous solution at appropriate concentrations to allow the resultant polymer to form a hydrogel. Prior to polymerization, a blood extract may be added to the mixture, where that blood extract contains either platelets or an extract of platelets. The composition comprising the precursor to a biomaterial (e.g., the monomer solution) with the added blood extract may be administered to and polymerized at the site of a defect.

In another embodiment, a composition comprising a precursor to a biomaterial is provided wherein the composition comprises a first monomer that is a PEG that has been derivatized with an ene moiety selected from any suitable ethylenically unsaturated group such as vinyl, acetyl, vinyl ether, allyl, acrylate, methacrylate, maleimide, and norbornene and a second monomer that is an enzymatically degradable peptide that contains a cysteine residue (thereby providing a thiol functional group). In one aspect, a monomer that is enzymatically degradable is a di-cysteine MMP-degradable peptide. In another aspect, a monomer that is enzymatically degradable is a di-cysteine plasmin-degradable peptide. In another aspect, a monomer that is enzymatically degradable is a di-cysteine plasmin- and MMP degradable peptide. The composition comprising the monomers may be combined with a blood extract that is either serum or platelet activated plasma and a photoinitiator in an aqueous solution. The mixture may then be polymerized in place using a light at a wavelength selected to fall within the absorbance spectrum of the photoinitiator. In one aspect the light source is a dental light.

In a further embodiment, a composition comprising a precursor to a biomaterial is provided wherein the composition comprises a first monomer that is a 4-arm PEG that has been derivatized with norbornene at the end of each arm and a second monomer that is a peptide containing at least 2 cysteines, optionally where the cysteines flank an enzymatically degradable moiety, such as an MMP- or Plasmin-cleavable sequence. In a further embodiment, a composition comprising a precursor to a biomaterial is provided wherein the composition comprises a first monomer that is a 4-arm 20 kD PEG that has been derivatized with norbornene at the end of each arm and a second monomer that is a peptide containing the sequence ALKVLKG (SEQ ID 39) and further containing at least flanking 2 cysteines. The monomers may be present at a molar concentration of 1:2 respectively, such that the molar concentration of thiol groups is equal to the molar concentration of ene groups. These monomers may be combined with a blood extract that is either serum or plasma that has been activated by ADP in an aqueous solution, where the monomers in aggregate make up less than about 10% wt/vol of the mixture and the blood extract makes up between about 5% and about 50% vol/vol of the mixture. The photoinitiator LiAP or NaAp may be added at a concentration between about 0.001% and about 1.0% wt/vol and the mixture may be delivered to the site of the defect (e.g., a wound). The mixture may then be polymerized in place, e.g., using a 380 nm light that operates at an intensity between 0.1 and 10 mW/cm$^2$. In other cases, polymerization can be initiated using a light with an intensity up to 1000 mW/cm$^2$ as is currently used in dental application.

In another embodiment, a composition comprising a precursor to a biomaterial is provided wherein the composition comprises three different monomers. In one aspect, a first monomer is a 4-arm PEG that has been derivatized with norbornene at the end of each arm, a second monomer is a linear PEG that has also been derivatized with norbornene at each end, and a third monomer is a peptide containing at least 2 cysteines, optionally wherein the at least two cysteines flank an enzymatically degradable sequence, such as an MMP- or Plasmin-cleavable sequence. In one aspect, a first monomer is a 4-arm 20 kD PEG that has been derivatized with norbornene at the end of each arm, a second monomer is a linear 6 kD PEG that has also been derivatized with norbornene at each end, and a third monomer is a peptide containing the sequence ALKVLKG and further containing at least 2 flanking cysteines. The monomers may be added at a molar concentration of 1:3.3:5.3 respectively, such that the molar concentration of thiol groups is equal to the molar concentration of ene groups. These monomers may be combined with a blood extract that is either serum or plasma that has been activated by ADP in an aqueous solution, where the monomers in aggregate make up less than about 10% wt/vol of the mixture and the blood extract makes up between about 5% and about 50% vol/vol of the mixture. The photoinitiator LiAP or NaAp may be added at a concentration of between about 0.001 and about 1.0% and the mixture may be added to the site of the defect where it may then be polymerized in place using a 380 nm light that operates at an intensity between 0.1 and 10 mW/cm$^2$ A composition comprising (i) a biomaterial or a precursor of a biomaterial (e.g., one or more monomers) and (ii) a blood extract is provided may have the (i) biomaterial or precursor of a biomaterial selected from any of the biomaterials or precursors thereof provided herein, including without limitation, in the Polymer Systems and Properties section provided below, and have the (ii) a blood extract selected from any of the blood extracts provided herein, including without limitation, in the Blood Extracts and Properties sections provided below. Thus, it is included and intended that all such combinations of (i) a biomaterial or a precursor of a biomaterial (e.g., one or more monomers) and (ii) a blood extract are provided the same as if each and every combination were specifically and individually listed.

It is also understood that any biomaterial or a precursor of a biomaterial (e.g., one or more monomers) may in one aspect be present in a composition that does not include a blood extract. For example, compositions comprising any biomaterial or a precursor of a biomaterial (e.g., one or more monomers) provided herein are described, wherein the composition does not comprise a blood extract. In this way, a composition, e.g., a pharmaceutical composition, comprising the biomaterial or precursor of a biomaterial may be free of a blood extract until such time as a blood extract is mixed with or introduced to, the composition (e.g., just prior to delivery of the mixture to an individual). Further, as described herein, also provided are compositions comprising a biomaterial or a precursor of a biomaterial, including but not limited to the biomaterial or a precursor of a biomaterial as described in the section entitled Polymer Systems and Properties. Pharmaceutical compositions comprising a biomaterial or a precursor of a biomaterial (e.g., one or more monomers) and a pharmaceutically acceptable carrier are provided. In one aspect, the pharmaceutically acceptable carrier is an aqueous carrier, such as a sterile aqueous carrier (e.g., saline).

Blood Extracts

Blood Extracts and Properties

As referred to herein, a "blood extract" is a material prepared from blood that can be whole blood, a fraction of blood including red blood cells, white blood cells, buffy coat, serum, plasma or platelet rich plasma, or an extract of blood including growth factors or extracellular matrix proteins purified or released from blood or a blood fraction. Blood is most desirably autologous, but may also be allogenic or xenogenic.

Blood is composed of two both cellular and liquid components. The cellular component consists of red and white blood cells, as well as platelets, which are technically not cells because they do not contain nuclei. The liquid component, or plasma, is the fluid in which the cellular component is suspended and contains water, electrolytes), nutrients (such as carbohydrates, lipids and amino acids), and soluble proteins (albumin, albumins, globulins, lipoproteins, enzymes, hormones, etc.). The cellular component takes up approximately 50% of the whole blood volume with plasma accounting for the remaining 50%. Cellular and plasma components can be separated by centrifugation of anticoagulated blood, with the cell fraction settling to the bottom and the plasma staying on top. If no anticoagulant is added when the whole blood is taken (or if clot activators are added), coagulation cascades are activated that result in clot formation within the blood sample. Centrifugation of clotted blood separates the clotted, insoluble fraction, which contains the cellular component of blood, from a liquid fraction. This liquid fraction is called serum and is different from plasma in that it is obtained after coagulation of blood.

1. Platelet Rich Plasma (PRP)

Methods that act to concentrate platelets above circulating levels in whole blood result in PRP. Two basic approaches for making PRP are used. One method, called the PRP method, uses as two-step procedure. In the first step whole blood is centrifuged at slow speed to pellet red blood cells, which are then removed from the sample. In the second step, a higher speed centrifugation in used to pellet platelets, allowing for the removal of a portion of the plasma. The fold concentration of platelets used in this method will then be dictated by amount of plasma removed and the final volume of plasma that is left with the platelets. The second method, called the buffy-coat method, involves only one fast spin to separate whole blood into three distinct layers: plasma, red cells, and a white buffy coat that sits at the interface of the plasma and red cell layer. The Buffy Coat contains most of the platelets but also some leukocytes and red cells.

Bedside methods also exist to isolate and concentrate platelets from individual patients. While the specific technologies vary, several FDA-approved devices are available that separate platelets from anticoagulated blood. The following table is provided to summarize some of the devices available for PRP collection from whole blood used in these processes.

| Device | List Price | Process Time | Disposable Kit | Platelet Concentration |
|---|---|---|---|---|
| Biomet GPS | $16,000 | 27 min | $700 | 3.2x |
| Cell Saver Based Systems | $10,000 | 20 min | $75-175 | 4-6x |
| Cytomedix Angel | $10,950 | 25 min | $495 | 4.3x |
| GenesisCS | $11,500 | 16 min | $1,560 | 10 ± 3 (4 ml)* |
| Harvest SmartPrep2 BMAC | $9,950 | 16 min | $395 | 4.0x |
| Deputy Symphony II | $9,950 | 16 min | $395 | 4.0x |
| Arteriocyte Medical Magellan™ | $9,950 | 17 min | $350-495 | 5.1x |
| Secquire | $6,000 | 20 min | $395 | 1.6x |
| SELPHYL (Cascade Medical) | NA | 20 min | NA | NA |
| CASCADE Autologous Platelet System | NA | 20 min | NA | NA |

Platelets can be seeded in a biopolymer at any density. In certain embodiments, the biopolymers contain $1 \times 10^3 - 4 \times 10^{10}$ platelets per $cm^3$. In another embodiment the platelets are seeded at a density greater than platelet concentration in blood that ranges between $1.5 \times 10^8$ and $4.5 \times 10^8$ platelets per $cm^3$. In another embodiment the platelets are seeded at a density that ranges between $0.4 \times 10^9$ and $1.2 \times 10^9$ platelets per $cm^3$. In certain embodiments, this concentration is 1, 2, 3, 4, 5, 6, 7, 8, 9, or 10 times greater than the concentration of platelets in blood. In other embodiments, the platelet concentration is less than the concentration of platelets in blood. In certain embodiments, this concentration is 1, 2, 3, 4, 5, 6, 7, 8, 9, or 10 times less than the concentration of platelets in blood.

Platelets can be present in a biopolymer for administration to a subject in any therapeutically effective amount. In certain embodiments, a biopolymer for administration to a subject can contain $1 \times 10^3 - 4 \times 10^{11}$ platelets. In another embodiment, a biopolymer for administration to a subject can contain between 1.5 and $4.5 \times 10^8$ platelets. In certain embodiments, the volume of the biopolymer can be between 1 and 100 $cm^3$. In more specific embodiments, the volume of the biopolymer can be between 1 and 10 $cm^3$.

As referred to herein, "platelet rich plasma" is defined as a fraction of platelets isolated from blood that contains a greater concentration of platelets than whole blood. In certain embodiments, PRP contains 2-10 times the concentration of platelets present in whole blood. In other embodiments, PRP contains 4-6 times the concentration of platelets present in whole blood. In other embodiments, PRP contains 2, 3, 4, 5, 6, 7, 8, 9, or 10 times the concentration of platelets in whole blood.

As referred to herein, "not substantially activated" is defined as a state in which less than 50% of platelets in a sample are activated. A platelet is activated when it releases clotting factors, such as when platelets come into contact with collagen.

As referred to herein, "not activated" is defined as a state in which less than 10% of platelets in a sample are activated. A platelet is activated when it releases clotting factors, such as when platelets come into contact with collagen or other mechanisms described herein.

As used herein, "about" a value or parameter includes (and describes) that value or parameter per se. For example, reference to "about" X includes (and describes) X per se.

As used herein, "individual" (interchangeably referred to as a "subject" herein) includes a mammal, such as a human. It is understood, however, that the invention finds use, for example, in the veterinary context, such as for use in agriculture and domestic pets (e.g., in a bovine, canine or feline).

PRP—Platelet Activation

Figure 6:
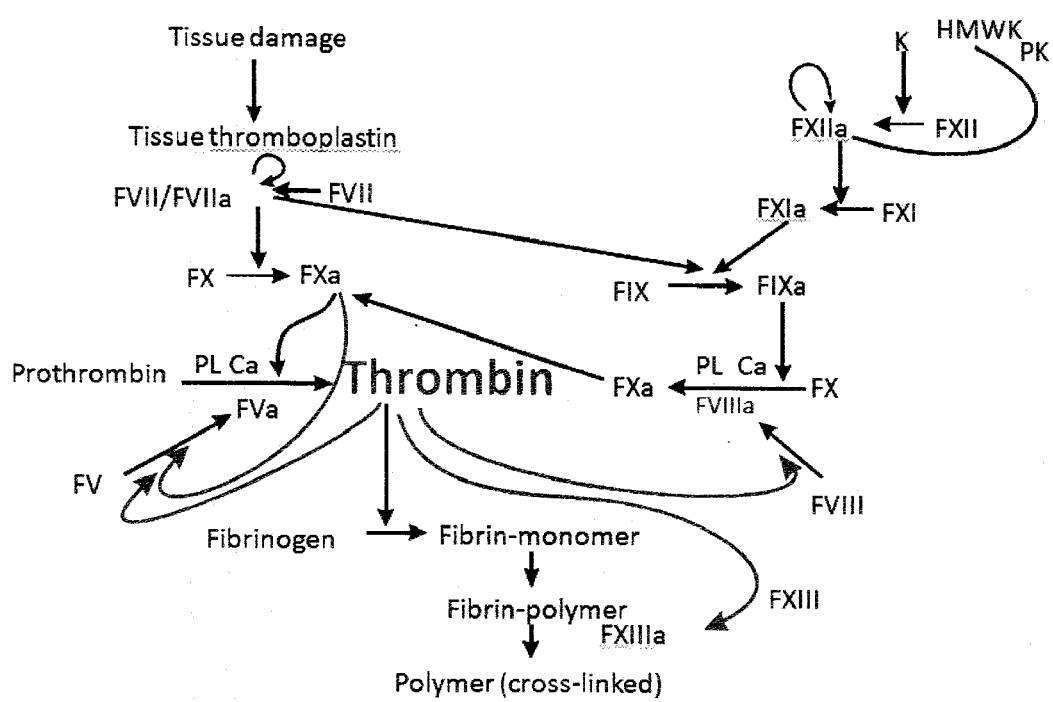
FIG. 6 illustrates the role of thrombin as a central protease in the coagulation cascade. Thrombin mediates signaling upon tissue damage that converts factor XI to XIa, VIII to VIIIa, V to Va, and fibrinogen to fibrin thus contributing to the activation of platelets.

Traditional methods to activate PRP involve mixing the PRP with thrombin and $Ca^{2+}$. Thrombin is the main effector protease of the coagulation system and is among the most effective activators of platelets. As illustrated in FIG. 6, thrombin is a central protease in the coagulation cascade: Thrombin acts to convert factor XI to XIa, VIII to VIIIa, V to Va, and fibrinogen to fibrin. As part of its activity in the coagulation cascade, thrombin also promotes platelet activation and aggregation via activation of protease-activated receptors (PARs) on the cell membrane of the platelet. Thrombin activity is dependent on $Ca^{2+}$, so anti-coagulates often act to chelate $Ca^{2+}$ ions and inhibit coagulation pathways. For this reason, $Ca^{2+}$ is added with thrombin for PRP activation.

Platelet activation of PRP can also be accomplished in other ways. Exposure to extracellular matrix proteins (such as collagen), elevated concentration of $Ca^{2+}$ ions, exposure to negatively charged surfaces such as certain types of glass, activation of PARs (e.g., thrombin or ligand mimics described below), increased ADP concentrations, $TxA_2$, and non-physiological flow conditions such as high values of shear stress are examples.

In addition to the induction of coagulation pathways, activation of platelets found in PRP results in the release of growth factors from platelet granules. The release of growth factors by platelets upon activation is thought to be a mechanism in which the body stimulates wound healing processes. In this way, the activation platelets serve two important roles in wound healing: (1) hemostasis in which clotting pathways act to stop bleeding and (2) the delivery of growth factors to stimulate healing.

Following activation of platelets in PRP and subsequent release of growth factors from the platelets, insoluble materials that result from cell debris and/or clotting can be pelleted by centrifugation, leaving a supernatant that is rich in cell-activating growth factors. These supernatants, or "PRP releasates," can then be combined with biomaterials that provide improved delivery and/or scaffolding properties for medical applications. PRP releasates can be added at any concentration suitable for combination with the biomaterial (for example: any of about 1%, 5%, 10%, 20%, 40% and 50% vol/vol final concentration).

Platelet activation and subsequent release of growth factors from platelet granules is a highly controlled process. In fact, evidence suggests that the activation of distinct pathways can result in the selective release of factors from different subtypes of granules in the platelets. For this reason, selective platelet activation with specific activators (thrombin, PAR1 peptide, PAR4 peptide, ADP, etc.) will result in different release profiles of the platelets. Therefore, PRP releasates collected from PRP samples activated with different activators have slightly different contents. The biological activities of these PRP releasates, therefore, would also be different. When mixed with biomaterials for medical applications, the selective activation of platelets can be used to tune the biological activity of the PRP releasate/biomaterial combination.

2. Serum

Serum is obtained from whole blood following the activation of clotting reactions and removal of insoluble proteins, cells, and cell debris. Typically, serum is prepared by either activating coagulation pathways in whole blood or allowing natural clotting pathways to occur. After clotting, the coagulated blood is centrifuged to pellet cells (red blood cells, leukocytes, etc.) and the fibrin clot that is formed during of coagulation. The clear supernatant that remains on top, or serum, is rich in electrolytes, antibodies, hormones, growth factors. Serum differs from plasma in that plasma represents the acellular soluble fraction of whole blood before clotting occurs.

While clotting will result in the depletion of clotting factors (for example: fibrin), this process is usually accompanied by platelet activation and subsequent release of soluble factors from platelet granules (for example: growth factors). For this reason, serum will contain many of the biologically active components of blood plasma. A Serum Metabolome Database (SMDB) (http://www.serummetabolome.ca) presents a comprehensive, web-accessible resource containing >4229 confirmed and probable serum/plasma compounds, their corresponding concentrations. In addition, blood plasma contains a wide variety of biologically active proteins that will also be present in serum: protein albumin (major contributors to osmotic pressure of plasma which assists in the transport of lipids and steroid hormones), globulins (used in the transport of ions, hormones and lipids assisting in immune function), and regulatory proteins (enzymes, proenzymes, hormones, and growth factors). While 7% of blood plasma protein is fibrinogen, which is essential in the clotting of blood, this protein is converted into insoluble fibrin upon clotting and becomes depleted in serum.

Serum extracted after coagulation can be mixed with biomaterials at final concentrations greater than 0% wt/vol and less than 100% wt/vol. These biomaterials can provide important characteristics to the serum that would improve handling properties and/or efficacy in medical applications.

Serum—Platelet Activation

Traditional methods to activate whole blood involve the activation of thrombin activity in whole blood. Thrombin is the main effector protease of the coagulation system and is among the most effective activators of platelets. Thrombin is a central protease in the coagulation cascade. Thrombin acts to convert factor XI to XIa, VIII to VIIIa, V to Va, and fibrinogen to fibrin. As part of its activity in the coagulation cascade, thrombin also promotes platelet activation and aggregation via activation of protease-activated receptors (PARs) on the cell membrane of the platelet. Thrombin activity is dependent on $Ca^{2+}$, so anti-coagulants used for plasma preparation often act to chelate $Ca^{2+}$ ions and inhibit coagulation pathways.

Platelet activation of whole blood can also be accomplished in other ways. Exposure to extracellular matrix proteins (such as collagen), elevated concentration of $Ca^{2+}$ ions, exposure to negatively charged surfaces such as certain types of glass, activation of PARs (e.g., thrombin or ligand mimics described below), increased ADP concentrations, $TxA_2$, and non-physiological flow conditions such as high values of shear stress are examples. As coagulation of whole blood can be stimulated by so many factors, the activation of platelets and subsequent clotting of whole blood rarely requires more than simple removal of blood from the body. This is why preventing coagulation from occurring in samples of whole blood requires the addition of anti-coagulants at the time of blood draw.

In addition to the induction of coagulation pathways, activation of platelets found in whole blood results in the release of growth factors from platelet granules. The release of growth factors by platelets upon activation is thought to be a mechanism in which the body stimulates wound healing processes. In this way, the activation platelets serve two important roles in wound healing: (1) hemostasis in which clotting pathways act to stop bleeding and (2) the delivery of growth factors to stimulate healing.

Following activation of platelets in whole blood and subsequent release of growth factors from the platelets, insoluble materials that result from cell debris and/or clotting can be pelleted by centrifugation, leaving a supernatant that is rich in cell-activating growth factors. Serum obtained from whole blood samples can then be combined with biomaterials that provide improved delivery and/or scaffolding properties for medical applications. It is foreseen that serum can be added at any number of concentrations with the biomaterial (for example: about 1%, 5%, 10%, 20%, 40% vol/vol final concentration).

Platelet activation and subsequent release of growth factors from platelet granules is a highly controlled process. In fact, evidence suggests that the activation of distinct pathways can result in the selective release of factors from different subtypes of granules in the platelets. For this reason, selective platelet activation with specific activators (thrombin, PAR1 peptide, PAR4 peptide, ADP, etc.) will result in different release profiles of the platelets. Therefore, serum collected from whole blood samples activated with different activators to have slightly different contents. The biological activities of these serum samples, therefore, would also be different. When mixed with biomaterials for medical applications, the selective activation of platelets could be used to tune the biological activity of the serum/biomaterial combination.

3. Plasma

Blood plasma is the liquid component of whole blood. Plasma makes up approximately 55% of the volume of whole blood and contains water, electrolytes, glucose, clotting factors, and soluble proteins (albumins, globulins, fibrinogen, growth factors, etc.). Blood plasma can be prepared by spinning anti-coagulated whole blood to separate cellular components (red blood cells, white blood cells, platelets) from the soluble fraction (plasma).

Many of the steps involved in clotting and platelet activation are dependent on $Ca^{2+}$, therefore clotting processes can be inhibited by sequestration of $Ca^{2+}$ by chelators such as EDTA, EGTA, and trisodium citrate. Additionally, clotting cascades can be inhibited by heparin, which binds to the enzyme inhibitor antithrombin III (AT), causing a conformational change that results in its activation. The activated AT then inactivates thrombin and other proteases involved in blood clotting. The rate of inactivation of these proteases by AT can increase by up to 1000-fold due to the binding of heparin. The activation of platelets in the presence of clotting inhibitors such as $Ca^{2+}$ chelators and heparin can effectively induce the release of growth factors from platelets without the conversion of soluble plasma proteins into insoluble form that are characteristic of clot formation (e.g., soluble fibrinogen into insoluble fibrin). In this way, plasma can be enriched in growth factors.

Anti-coagulated plasma (before or after platelet activation in the presence of anti-coagulating agents that prevent clot formation as described above) can be mixed with biomaterials at final concentrations greater than 0% wt/vol and less than 100% wt/vol. These biomaterials can provide important characteristics to the plasma that would improve handling properties and/or efficacy in medical applications.

Plasma—Platelet Activation

As described in the previous sections, platelet activation of whole blood can be accomplished in many ways. Mixture with thrombin, exposure to extracellular matrix proteins (such as collagen), elevated concentration of $Ca^{2+}$ ions, exposure to negatively charged surfaces such as certain types of glass, activation of PARs (e.g., thrombin or ligand mimics described below), increased ADP concentrations, $TxA_2$, and non-physiological flow conditions such as high values of shear stress are examples.

Plasma—Platelet Activation

While activation of platelets generally acts to induce coagulation pathways, it is possible to stimulate platelets while simultaneously inhibiting coagulation cascades. In this way, the release of growth factors by platelets upon activation would effectively increase the concentration of these factors in the plasma fraction. Plasma obtained from whole blood samples (either with or without platelet activation) can then be combined with biomaterials that provide improved delivery and/or scaffolding properties for medical applications. It is foreseen that plasma can be added at any number of concentrations with the biomaterial (for example: about 1%, 5%, 10%, 20%, 40% vol/vol final concentration).

Platelet activation and subsequent release of growth factors from platelet granules is a highly controlled process. In fact, evidence suggests that the activation of distinct pathways can result in the selective release of factors from different subtypes of granules in the platelets. For this reason, selective platelet activation with specific activators (thrombin, PAR1 peptide, PAR4 peptide, ADP, etc.) will likely result in different release profiles of the platelets. Therefore, plasma collected from whole blood samples activated with different activators would be expected to have slightly different contents. The biological activities of these plasma samples, therefore, would also be different. When mixed with biomaterials for medical applications, the selective activation of platelets could be used to tune the biological activity of the plasma/biomaterial combination.

4. Other Blood Extracts

Additional blood fractions/extracts could be used as a source biological activity. Cell fractions (red blood cells, "buffy coat" layers, white blood cells, circulating stem cells, lymphocytes, leukocytes, etc.) can be isolated by a variety of techniques including centrifugation, flow cytometry, antibody selection, and other known to those skilled in the art Similarly, intact platelets, though not technically cells, could be purified. These isolated cell/platelet fractions, either alone or in combination, could be used in combination with a biomaterial to provide specific medical benefit and may help in healing or regenerative processes. It is foreseen that these cell/platelet fractions can be added at any number of concentrations with the biomaterial (for example: about 1%, 5%, 10%, 20%, 40% vol/vol final concentration).

Other fractionation/extraction processes could be employed to purify specific acellular fractions of blood. Whole blood, PRP, serum, plasma, red blood cells, or any other possible fraction of blood could be further processed to extract components with specific biological activity. For example, platelets lysed by mechanical disruption in water to release soluble growth factors contained within the platelet granules. Following centrifugation to pellet cell debris, the soluble fraction, or platelet lysate, can be removed and used in combination with an appropriate biomaterial. Furthermore, the platelet lysate could be further fractionated with standard biochemical approaches (chromatography, filtration, etc.) to yield an even more purified extract.

Biopolymers and Biopolymer Precursors

Polymer Systems and Properties

This disclosure provides blood extracts associated with biomaterials. In certain embodiments, these biomaterials are polymer scaffolds. In certain embodiments, polymer scaffolds include one or more monomers that under the appropriate conditions will form a polymer scaffold to encapsulate the blood extract. These monomers may undergo homopolymerization or copolymerization. A monomer may itself comprise a polymeric unit, provided that the monomer is suitable for further polymerization, such as by the presence of a functional group that is reactive with a mutually reactive functional group on the same or another monomer, such that polymerization may occur. It is thus understood that the monomers detailed herein and below may be derivatized to include a functional group (e.g., a functional group that is mutually reactive with a functional group on another monomer, which may be the same or different). For example, a thiol functional group is mutually reactive with an ene functional group. Thus, a monomer detailed herein may be derivatized to include a thiol or ene functional group. A monomer comprising a thiol functional group may be combined with a monomer comprising an ene functional group under conditions suitable for reaction between the thiol and the ene functional group (e.g., in one aspect, the conditions include a light source and a photo initiator selected from the group consisting of Irgacure 2959, Irgacure 184, Irgacure 651, LiAP and NaAP). As described above, in other embodiments, a chemical initiator, or both a photoinitiator and a chemical initiator is used.

In one aspect, an ene moiety is present on a first monomer (e.g., a PEG monomer derivatized to include an ene moiety, such as by the addition of a norbornene moiety to PEG termini) and a thiol moiety is present on a second monomer, such as when a peptide second monomer comprises a cysteine. Thus, it is understood that the monomers detailed herein may be derivatized to include mutually reactive functional groups (e.g., a thiol and/or ene or yne groups) such that a polymer may be formed. In one aspect, a monomer is derivatized with a functional group at the terminui of the monomer (e.g., at the termini of a PEG monomer or at the termini of a peptide monomer). Further, it is understood that a linking group may be used to link the monomer and the functional group (e.g., by using a linking chemistry, an ene or thiol functionality is added to a monomer). In one aspect, a linking group is selected that provides an ester or an amide linkage between the monomer and the functional group. Monomers may be derivatized according to known chemical reactions and under standard reaction conditions, including those provided herein. Monomer(s) which may be derivatives with a functional group include, but are not limited to, poly(lactic acid) (PLA), polyglycolide (PGA), copolymers of PLA and PGA (PLGA), poly(vinyl alcohol) (PVA), poly(ethylene glycol) (PEG), poly(ethylene oxide), poly(ethylene oxide)-co-poly(propylene oxide) block copolymers (poloxamers, meroxapols), poloxamines, polyanhydrides, polyorthoesters, poly(hydroxy acids), polydioxanones, polycarbonates, polyaminocarbonates, poly(vinyl pyrrolidone), poly(ethyl oxazoline), carboxymethyl cellulose, hydroxyalkylated celluloses such as hydroxyethyl cellulose and methylhydroxypropyl cellulose, and natural polymers such as nucleic acids, polypeptides, polysaccharides or carbohydrates such as polysucrose, hyaluronic acid, dextran and similar derivatives thereof, heparan sulfate, chondroitin sulfate, heparin, or alginate, and proteins including without limitation gelatin, collagen, albumin, or ovalbumin, or copolymers, or blends thereof. In particularly preferred embodiments, the monomers can be selected from poly(lactic acid) (PLA), poly(vinyl alcohol) (PVA), and poly(ethylene glycol) (PEG). As is discussed in more detail in the section titled "Nucleophilic Addition Reaction", while it is often desirable that both monomers are themselves polymers, it is not necessary. For example, in some implementations the thiol containing monomer can be a small molecule such as 1,2 ethylene dithiol or dithiothreitol (DTT_. In one aspect, the monomers listed are derivatized with an ene or yne functional group. In another aspect, the monomers listed are derivatized with an ene functional group such as by the addition of norbornene, which may be bound to the monomer via a linking group such as an amide or ester moiety.

In certain embodiments, the monomers making up polymer scaffolds include functional groups necessary for the crosslinking of the monomers to form the polymer. In some cases, the monomers may have to be derivatized to include these functional groups. Depending on the crosslinking chemistry employed, functional groups may include thiol, amino, carboxyl, hydroxyl, alkene, alkyne, or other functional groups.

The resulting polymers can be designed to be degradable if one or more of the co-monomers are chosen to be degradable. As used herein, a polymer is degradable when its rate of degradation is increased by greater than 10% when the polymer is exposed to a degrading agent or process. Degrading agents include chemicals, radiation, heat and enzymes.

Figure 7:
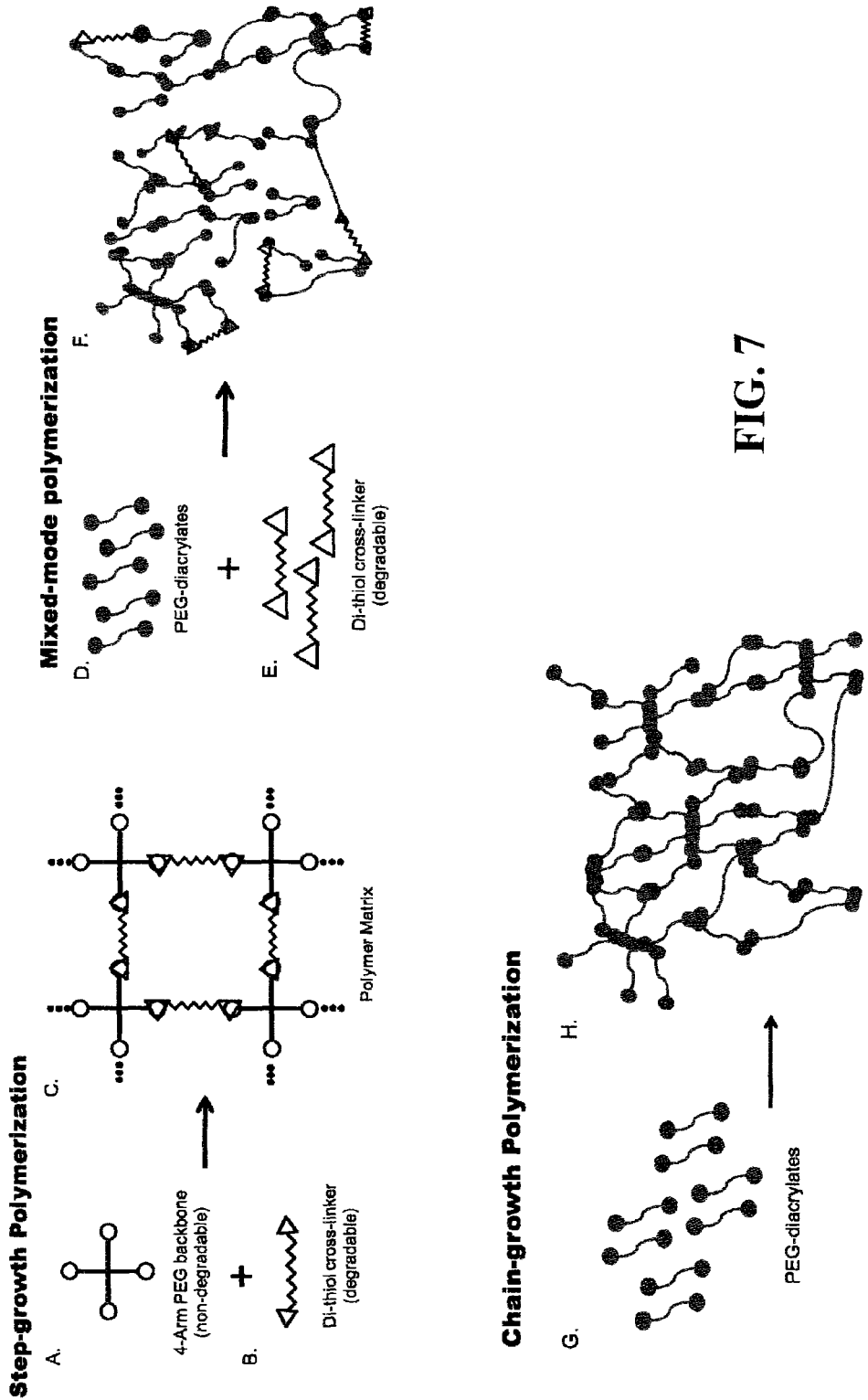
FIG. 7 is a depiction of step-growth, mixed-mode, and chain-growth polymerization.

In preferred embodiments, these monomers are polymerized via a step growth mechanism such that a step growth polymer (also referred to as a step growth network) is formed. FIG. 7 contains schematic representations of a step growth, mixed-mode growth, and a chain growth network.

In one embodiment, a PEG monomer is combined with a second enzymatically degradable peptide monomer. These monomers are each derivatized such that the monomers can form a polymer via a step-growth mechanism, thereby forming a step growth polymer. These monomers are contained within an aqueous solution at appropriate concentrations to allow the resultant polymer to form a hydrogel. Prior to polymerization, a blood extract is added to the mixture, where that blood extract contains either platelets or an extract of platelets. The monomer solution with the added blood extract is polymerized at the site of a defect.

In another embodiment, one monomer is a PEG that has been derivatized with an ene moiety selected from any suitable ethylenically unsaturated group such as vinyl, acetyl, vinyl ether, allyl, acrylate, methacrylate, maleimide, and norbornene and the other monomer is an enzymatically degradable peptide that contains a cysteine residue (thereby providing a thiol functional group). In one aspect, the enzymatically degradable peptide is a peptide that contains a cysteine residue at either end of an enzymatically degradable peptide moiety, such that the peptide comprises at least two cysteine moieties. These monomers are combined with a blood extract that is either serum or platelet activated plasma and a photoinitiator in an aqueous solution. The mixture is then polymerized in place using a light at a wavelength selected to fall within the absorbance spectrum of the photoinitiator, In a preferred embodiment, one monomer is a 4-arm 20 kD PEG that has been derivatized with norbornene at the end of each arm and the second monomer is a peptide with containing the sequence ALKVLKG and further containing at least flanking 2 cysteines. The monomers are added at a molar concentration of 1:2 respectively, such that the molar concentration of thiol groups is equal to the molar concentration of ene groups. These monomers are combined with a blood extract that is either serum or plasma that has been activated by ADP in an aqueous solution, where the monomers in aggregate make up less than 10% wt/vol of the mixture and the blood extract makes up between 5% and 50% vol/vol of the mixture. The photoinitiator LiAP or NaAp is added at a concentration between 0.001% and 1.0% wt/vol and the mixture is added to the site of the defect. The mixture is then polymerized in place using a 380 nm light that operates at an intensity between 0.1 and 10 $mW/cm^2$ In another preferred embodiment, three monomers are used. One monomer is a 4-arm 20 kD PEG that has been derivatized with norbornene at the end of each arm and the second monomer a linear 6 kD PEG that has also been derivatized with norbornene at each end. The third monomer is a peptide with containing the sequence ALKVLKG (SEQ ID NO: 39) and further containing at least 2 flanking cysteines. The monomers are added at a molar concentration of 1:3.3:5.3 respectively, such that the molar concentration of thiol groups is equal to the molar concentration of ene groups. These monomers are combined with a blood extract that is either serum or plasma that has been activated by ADP in an aqueous solution, where the monomers in aggregate make up less than 10% wt/vol of the mixture and the blood extract makes up between 5% and 50% vol/vol of the mixture. The photoinitiator LiAP or NaAp is added at a concentration between 0.001 and 1.0% and the mixture is added to the site of the defect. The mixture is then polymerized in place using a 380 nm light that operates at an intensity between 0.1 and 10 $mW/cm^2$. Photo-initiated polymerizations can typically proceed via a chain-growth, step-growth or mixed-mode polymerization mechanism. These step growth mechanisms include different chemical steps than the chain growth mechanisms described below and as a consequence follow different kinetics, may generate intermediates that are more or less toxic to tissues and biological molecules, and result in the polymeric networks with profoundly different mechanical and biological properties.

Chain-growth polymerization proceeds via addition of unsaturated monomer molecules onto the active site on a growing polymer chain one at a time. Often, chain growth polymerization is a radical-mediated polymerization of olefin functional groups, where olefin groups are provided, for example, by allyl ethers, vinyl ethers, acrylates, methacrylates, hydroxymethylacrylates, acrylamides or other moieties containing unsaturated carbon-carbon bonds. Addition of olefin moieties upon polymerization results in formation of kinetic chains that are linear chains of saturated carbon-carbon bonds. Due to stochastic nature of chain-growth polymerization, kinetic chains are highly heterogeneous in length, and therefore resulting polymer network is highly heterogeneous in structure. This heterogeneity results in poor mechanical properties of chain-growth networks, such as low ductility and toughness. Kinetic chains are also poorly metabolized by the human body and may exceed in size the renal clearance limit of ~60 kilo Dalton. Additional disadvantages of the chain-growth polymerizations include inhibition by oxygen and requirement for high concentration of radical species for the polymerization to proceed. High concentrations of radicals in photo-initiated processes are typically achieved by application of high concentrations of photo-initiator and high dose of initiating light, both harmful for biological molecules, cells and tissues. In addition, high concentration of radical species themselves is harmful for biological molecules, cells and tissues.

Step-growth polymerization proceeds via a different mechanism, in which bifunctional or multifunctional monomers react to form dimers, and further, oligomers and polymers. As disclosed in the following sections, a variety of chemical and biophysical processes may be harnessed to form a step-growth polymeric network. Polymerization of bifunctional monomers results in the formation of a linear polymer, rather than a crosslinked polymer. Crosslinked networks can be readily formed by increasing the functionality, i.e., increasing the degree of branching, of one or more of the monomers to be greater than two.

In the preferred embodiments, step-growth polymerization is the photo-initiated thiol-ene polymerization, as disclosed in the following section 2. Thiol-ene polymerizations are photochemically initiated free-radical processes that take place between thiols and olefins via a sequential propagation/chain-transfer process. Thiol-ene polymerizations have a number of significant and unique advantages that make them particularly beneficial. These benefits include fast polymerization kinetics, very low radical concentration, low concentrations of photoinitiator and low dose of light required for polymerization to occur resulting in lesser damage to biological molecules, cells and tissues from these potentially toxic factors, the lack of oxygen inhibition and the ease with which monomers of significantly varying chemistry can be copolymerized. This is illustrated by the Example 18, where kinetics of the formation and the elastic properties of the step-growth and chain-growth networks of similar monomer composition are compared side by side by shear rheometry in situ. Photo-induced polymerization of telechelic macromolecular monomers (4% PEG-diacrylate or 4% PEG-tetranorbornene in water) into a crosslinked network results in hydrogels with distinct mechano-elastic properties. The shear storage modulus (G') of the resulting networks reflects overall stiffness of the product hydrogels and may be related to the structural properties of these networks by polymer elasticity theories that are well known in the art. As clearly illustrated by the Example 18, the step-growth polymer ("step") is completely formed within one minute of irradiation at 385 nm at 3 $mW/cm^2$ (light intensity that is much lower than typically used in dental applications), while under the same conditions the chain-growth process exhibits a significant lag of about one and a half minute and reaches its maximal stiffness only after about 8 minutes of irradiation, with difference in irradiation time and necessary dose of UV light of almost an order of magnitude. Also note that the plateau value of the storage modulus for step-growth network (~4.2 kPa) is about 40% higher than for the chain growth network of similar composition (~3.0 kPa), indicating that step-growth network requires lower concentration of the material to generate a hydrogel of specific stiffness than the chain-growth network, a consideration important from a pharmacological standpoint.

Under special circumstances, polymerization can proceed via a mixed-mode mechanism, where step-growth and chain-growth polymerization proceed concurrently, such as for example upon radical-based photo-induced polymerization of monomers bearing thiol and acrylate moieties. It should be understood to the one skilled in art that mixed-mode polymerization results in the formation of kinetic chains (via acrylate moieties reacting with each other) and therefore results in the networks of heterogeneous nature, bearing all the disadvantages disclosed for the chain-growth networks in the preceding section. As illustrated by the Example 18, incorporation of dithiol-containing peptide crosslinker into the otherwise chain-growth polymerization reaction results in acceleration of the network formation, although not quite to the rate afforded by the step-growth thiol-ene polymerization. This effect is probably due to the high reactivity of thiyl radicals that are generated in the course of mixed mode and step-growth polymerizations but not in the course of chain growth process. However, even if the overall rate of polymerization increases upon increasing the dithiol crosslinker content in the mixed mode polymerization process, this comes at a cost of deteriorating mechano-elastic properties of the resulting network, as illustrated by the lower values of storage modulus (G') that are attained at the end of polymerization.

Regardless of the chemical mechanism of formation, step-growth polymeric networks avoid formation of the highly heterogeneous kinetic chains and result in highly homogeneous, well-connected networks that are biologically and often mechanically superior to the chain-growth networks of similar composition. For example, homogeneous network structure and lack of kinetic chains in step-growth polymers allow to control the size of degradation products more precisely than in the case of highly irregular chain-growth networks. As illustrated in the Example 19, the size distribution of the products of enzymatic degradation of the step-growth network is dictated by the size distribution of the non-degradable monomer that was utilized in the network formation. At the same time, chain-growth or mixed mode polymerization of even smaller monomers results in formation of biologically non-degradable kinetic chains that are at least an order of magnitude larger in size. In addition, step-growth networks can be easily locally degraded and invaded by cells, a feature critical for polymeric scaffold targeting biomedical applications, while non-degradable kinetic chains formed in the course of chain-growth or mixed mode polymerizations interfere with this process. This is illustrated by the cellular outgrowth assay disclosed in the Example 20. In this experiment, human dermal fibroblasts encapsulated in small collagen plugs are further embedded into hydrogels of similar composition that are prepared by in situ photo-induced polymerization either via step-growth or mixed mode mechanisms and are allowed to invade the hydrogels over time. Despite the fact that all three hydrogel formulations can be easily enzymatically degraded to completion in vitro (Example 19) only step-growth hydrogels permit robust outgrowth of fibroblasts over 24 hours. Therefore, networks formed by step-growth polymerization afford scaffolds that are more suitable for biological, biomedical and regenerative applications than the networks formed by chain-growth or mixed mode mechanisms.

In a preferred embodiment of a step growth polymer, free radical thiol-ene chemistry is employed using norbornene terminated 4-arm PEG crosslinked by peptides containing two or more thiol containing cysteine residues. In some embodiments, these PEGs could have a molecular weight of 1 kDa, 3 kDa, 5 kDa, 10 kDa, 20 kDa, 30 kDa, 40 kDa, 50 kDa or 60 kDa. Polymerization is initiated by mixing these two monomers with a photo-initiator and subsequent exposure to light. In this embodiment, the norbornene terminated 4-arm PEG and the thiol containing peptides are mixed in a ratio such that the concentrations of norbornene supplied ene groups is equal to the concentration of cysteine supplied thiol groups.

In another preferred embodiment of a step growth polymer, three monomer groups are used: one monomer is a norbornene terminated 4-arm PEG, the second monomer is a norbornene terminated linear PEG and the third monomer is a peptides containing two or more thiol containing cysteine residues. In some embodiments, these PEGs could have a molecular weight of 1 kDa, 3 kDa, 5 kDa, 10 kDa, 20 kDa, 30 kDa, 40 kDa, 50 kDa or 60 kDa. Polymerization is initiated by mixing these three monomers with a photo-initiator and subsequent exposure to light. In this embodiment, the norbornene terminated 4-arm PEG, the norbornene terminated linear PEG, and the thiol containing peptides are mixed in a ratio such that the concentrations of norbornene supplied ene groups is equal to the concentration of cysteine supplied thiol groups. This three component system can advantageously be employed when it is desirable to have long arms while maintaining relatively short monomer lengths.

In addition to free radical thiol-ene chemistry, other chemistries can be employed and will be familiar to those skilled in the art. These include the free-radical thiol-yne and the nucleophilic addition chemistries described below. While not a preferred embodiment, chain growth polymers, for example those obtained by homopolymerization through the use of diacrylates, can also be used with other aspects of this current invention.

As mentioned above, free radical polymerization can be initiated through the use of a photoinitiator, chemical initiators, or both photo and chemical initiators. In certain embodiments, a photoinitiator is selected from Irgacure 2959, Irgacure 184, Irgacure 651, lithium phenyl-2,4,6-trimethylbenzoylphosphinate (LiAP) or sodium phenyl-2,4,6-trimethylbenzoylphosphinate NaAP. The initiating light should be of a wavelength chosen to match the photoinitiator. This wavelength could be in the UV, visible or infrared spectrum. In the case of the photoinitiator LiAP, the light is preferably at a wavelength of 380 nm, although other wavelengths may be used. Free radical polymerization can all be chemically initiated, for example through the use organic peroxides. Free radical polymerization can all be enzymatically initiated, for example through the use of glucose oxidase. Combinations of photoinitiators and chemical initiators can also be used.

In addition to the free-radical chemistry described above, other crosslinking chemistries can be employed to create a step growth polymer, including Michael Addition (also known as nucleophilic addition) chemistry, oxidation chemistry, or other chemistries well known to those skilled in the art. In another embodiment, Michael Addition chemistry is employed using a maleimide, vinyl sulfone or acrylated terminated 4-arm PEG crosslinked by peptides containing two or more thiol containing cysteine residues. In some embodiments, these PEGs could have a molecular weight of 1 kDa, 3 kDa, 5 kDa, 10 kDa, 20 kDa, 30 kDa, 40 kDa, 50 kDa or 60 kDa.

In preferred embodiments, one or more of the monomers may contain a degradable moiety. This moiety could be chemically, hydrolytically or enzymatically degradable. In another embodiment, one of the monomers is a peptide that contains an amino acid sequence that can be cleaved by a protease, such as matrix metalloproteases, serine proteases, aspartic acid proteases, threonine proteases, glutamic acid proteases and cysteine proteases. Other biological polymers that may be degraded by other enzymes may also be used.

The choice of degradable linker should be chosen based on the specific application. For example, in applications that require participation by fibroblasts, it may be useful to have MMP-cleavable crosslinkers. Additional sequences that can advantageously utilized include those described below in the section titled "*Nucleophilic Addition Reaction*" under the subheading "Peptides."

In some cases it may be necessary to determine the optimal linker through testing in a cellular or animal model. As detailed in the example section below, the use of an animal model for skin allowed us to identify a novel crosslinker for skin wound healing includes both a MMP- and Plasmin degradable site. This crosslinker contains the sequence XXXXXX (SEQ ID NO: 3) and at least two cysteines. Based on this disclosure, other derivatives of this sequence will be obvious to those skilled in the art.

The above monomers can be preset in a composition, including a pharmaceutically acceptable composition, which may optionally contain other components, such as an additional therapeutic agent and/or a photoinitiator such as photoinitiator is selected from the group consisting of Irgacure 2959, Irgacure 184, Irgacure 651, LiAP and NaAP. The above monomers may be polymerized in the presence of the blood extract and a solvent such as, but not limited to, water. In the case of an aqueous solvent, salts or buffers may be added to match physiological conditions. Thus, compositions comprising a monomer and an aqueous carrier are included herein, including pharmaceutically acceptable compositions comprising a monomer with mutually reactive functional groups and a sterile aqueous carrier, and optionally containing one or more additional therapeutic agents and/or photoinitiators. For example, the aqueous solvent may be phosphate buffered saline (PBS). In the case of hydrogels, the total of the solvent and blood extract may make up >95%, >90%, >80%, >70%, >60% or greater than 50% of the hydrogel by weight. In some cases, advantageous properties may be obtained by choosing monomers such that the modulus of elasticity of the resultant material equals some specific value. For skin wound healing, the modulus of elasticity of elasticity may be chosen to match the modulus of elasticity of skin, or approximately 6 kPA. Similarly, the modulus of elasticity may be chosen to match materials such as cartilage, muscle, neural or bone tissue. As is discussed in more detail below, in some cases it may be desirable to use a material with a lower modulus elasticity to provide faster cellular migration.

In certain embodiments, the composition described herein can further include an agent that has a biological function or activity, including pharmaceutically active agents. Peptide agents can be selected from adhesion peptides (such as RGD adhesion sequence), growth factors, hormones, anti-hormones, signaling compounds, enzymes, serum proteins, albumins, macroglobulins, globulins, agglutinins, lectins, extracellular matrix proteins, antibodies, and antigens. Non-peptide agents that can be incorporated into the polymeric material include analgesics, antipyretics, non-steroidal anti-inflammatory drugs, anti-allergics, antibacterial, antifungal or antimicrobial drugs, anti-anemia drugs, cytotoxic drugs, antihypertensive drugs, dermatological drugs, psychotherapeutic drugs, vitamins, minerals, anorexiants, dietetics, antiadiposity drugs, carbohydrate metabolism drugs, protein metabolism drugs, thyroid drugs, anti-thyroid drugs, and coenzymes. In certain embodiments, the composition described herein can further include an agricultural chemical. The agricultural chemical can be selected from fungicides, herbicides, fertilizers, pesticides, carbohydrates, nucleic acids, organic molecules, and inorganic biologically active molecules.

With respect to the above two paragraphs, it is not necessary that these agents be covalently attached to the polymer. However, in certain embodiments, these agents may be covalently attached to polymer using the same chemistry as is used in the polymerization step. In other embodiments, these agents may be covalently attached using other chemistries.

A number of different crosslinking chemistries can be employed to create the polymer scaffold. A polymer (e.g., a polymeric biomaterial) produced by the processes detailed herein and below are included within the invention. Three embodiments of polymer classes and associated chemistries are detailed below.

1. Thiol-yne Chemistry

The present disclosure includes scaffolds which are thiol-yne hydrogels. These scaffolds are produced by the radical mediated polymerization of monomers containing alkyne and thiol functional groups. In certain embodiments, the scaffold is a three dimensional polymer matrix. Thiol-yne hydrogels are taught in International Application No. PCT/US2012/022920 which is incorporated, herein, by reference in its entirety.

Thiol-yne polymerizations are radical mediated processes that take place between thiols and alkyne-containing moieties via a sequential propagation/chain-transfer process. In certain embodiments, polymerizations occur between two types of monomer. The first type of monomer is derivatized with thiol groups and the second type of monomer is derivatized with alkyne groups. The thiol monomer can be derivatized with 2, 3, 4, 5, 6, 7, 8, 9, 10 or more thiol groups. The alkyne monomer can be derivatized with 1, 2, 3, 4, 5, 6, 7, 8, 9, 10 or more alkyne groups. For example, in this embodiment, the thiol monomer could have three thiol moieties and the alkyne monomer could have two alkyne moieties. In other embodiments, each thiol-containing component has an average of at least two thiol groups. In this embodiment, because each alkyne functional group is capable of undergoing up to two reactions with thiols, each alkyne-containing component has at least one alkyne functional group, (i.e. the monomer contains one or more triple bonds). Crosslinked gels can be readily formed by increasing the monomer functionality of one or both of the monomers to allow for more than two reactions per monomer.

In one embodiment, these scaffolds may be built upon degradable materials, such as peptides, proteins, and poly (lactic acid) blocks. In another embodiment, they can incorporate chemicals and live cells within the polymer matrix.

In one embodiment, an initiating system is used to generate radicals that initiate polymerization. Radicals may be generated by redox, thermal, enzymatic or photochemical mechanisms.

In one embodiment the initiator is a photoinitiator present in the monomer solution at a concentration of less than 5% by weight and is capable of initiating polymerization upon exposure to UV, visible or infra-Red light at an intensity general ranging from 0.1 to 200 mW/cm$^2$ with both higher and lower light intensities possible. Higher intensity lights include those currently used for dental application that have operating ranges of 1000 mW/cm$^2$ and higher.

In a preferred embodiment initiator concentration and light intensity will be sufficient for polymerization to occur, resulting in a crosslinked material, often in less than 20 minutes, preferably polymerization will occur in less than 5 minutes, preferably polymerization will occur in less than 2 minutes, more preferably polymerization will occur in less than 1 minute. Initiators include, but are not limited to LiAp, NaAp, Irgacure 2959, 184 and 651.

In an embodiment the initiator will be capable of initiating polymerization in a dilute monomer solution containing more than 50% solvent. Preferably the initiator is a photoinitiator capable of initiating polymerization in the presence of water, and water is preferably used as the solvent. More preferably the photoinitiator will be present in the monomer solution in an amount less than or equal to 0.5%, 1% or 5% by weight and is a water soluble photoinitiator such as but not limited to Irgacure-2959 or water soluble acyl-phosphinate initiator such as but not limited to salts of phenyl-2,4,6-trimethylbenzoylphosphinate.

As mentioned above, the resulting polymer may be cross-linked wherein at least one of the co-monomers can form more than two bonds on average. In specific embodiments, at least one of the monomers contains more than one alkyne functionality or more than two thiol functionalities. In one embodiment, the thiol containing monomer contains two thiol groups and the alkyne containing monomer contains 2, 3, 4, 5, 6, 7, 8, 9 or 10 alkyne groups. In another embodiment, the alkyne containing monomer contains 1 alkyne group and the thiol containing monomer contains 3, 4, 5, 6, 7, 8, 9 or 10 thiol groups. In another embodiment, the alkyne containing monomer contains 2 alkyne groups and the thiol containing monomer contains 3, 4 or 8 yne groups. Based on this disclosure, other combinations will be understood by one skilled in the art.

In some embodiments, the monomer is derivatized to include a thiol or alkyne moiety. In preferred embodiments, the core of the monomer structure, to which the reactive yne or thiol moieties are attached, can be selected from one or more of the following: poly(lactic acid) (PLA), polyglycolide (PGA), copolymers of PLA and PGA (PLGA), poly(vinyl alcohol) (PVA), poly(ethylene glycol) (PEG), poly(ethylene oxide), poly(ethylene oxide)-co-poly(propylene oxide) block copolymers (poloxamers, meroxapols), poloxamines, polyanhydrides, polyorthoesters, poly(hydroxy acids), polydioxanones, polycarbonates, polyaminocarbonates, poly(vinyl pyrrolidone), poly(ethyl oxazoline), carboxymethyl cellulose, hydroxyalkylated celluloses such as hydroxyethyl cellulose and methylhydroxypropyl cellulose, and natural polymers such as nucleic acids, polypeptides, polysaccharides or carbohydrates such as polysucrose, hyaluronic acid, dextran and similar derivatives thereof, heparan sulfate, chondroitin sulfate, heparin, or alginate, and proteins including without limitation gelatin, collagen, albumin, or ovalbumin, or copolymers, or blends thereof. In particularly preferred embodiments, the monomers can be selected from poly(lactic acid) (PLA), poly(vinyl alcohol) (PVA), and poly(ethylene glycol) (PEG). PLA monomers provide degradability to the system while PVA and PEG enhance the hydrophilic nature of the hydrogel and provide for the possibility of further derivatization and/or extensive crosslinking. Peptides can also be derivatized with thiol or alkyne groups.

According to the compositions and methods described herein, peptides can be monomers making up the scaffold. These monomers are derivatized with alkyne or thiol groups. Preferably, thiols are included within the peptides through the use of cysteine residues. Peptides can also be covalently attached to the scaffold matrix, but not be either the first or second monomer. In certain embodiments, these peptides can have a biological activity or function. Peptides can also be encapsulated within the matrix but not covalently attached to the matrix. In certain embodiments, these peptides can also have a biological activity or function.

Similarly, other non-peptide agents that have a biological activity or function can also be covalently attached to the scaffold matrix, but not be either the first or second monomer. This attachment can employ the same thiol-yne chemistry as is used in the first or second monomer, or could use a different attachment chemistry. Non-peptide agents can also be encapsulated within the matrix but not covalently attached to the matrix.

A biopolymer produced by a thiol-yne chemistry, including without limitation any of the chemistries disclosed herein, are provided herein.

2. Thiol-ene Chemistry

The present disclosure includes scaffolds which are thiol-ene hydrogels. These thiol-ene hydrogels can be built upon degradable materials, such as PVA, PEG and PLA blocks. Thiol-ene hydrogels are taught in U.S. Pat. No. 7,288,608 which is incorporated, herein, by reference in its entirety.

Thiol-ene polymerizations are photochemically initiated, step growth, free-radical processes that take place between thiols and olefins via a sequential propagation/chain-transfer process. For polymerization to occur, each thiol-containing component should have an average of at least two thiol groups and each olefin-containing component should have at least two ene functional groups, (i.e. the monomer should contain two or more double bonds). Polymerization of a dithiol and a diene results in the formation of a linear polymer, rather than a crosslinked polymer. Crosslinked gels can be readily formed by increasing the functionality, i.e., increasing the degree of branching, of one or both of the monomers to be greater than two. Thiol-ene polymerizations have a number of significant and unique advantages that make them particularly beneficial. These benefits include a step growth polymerization that causes the molecular weight to build up more slowly, the ability to photoinitiate the sample without any need for a distinct (and possibly cytotoxic) initiator specie, the ability to polymerize extremely thick (more than 30 cm) samples because of a self-eliminating light intensity gradient, the very low radical concentration present during polymerizations producing less cellular damage from the free radicals, the lack of oxygen inhibition and the ease with which monomers of significantly varying chemistry can be copolymerized.

In certain embodiments, thiol-ene systems form ground state charge transfer complexes, and therefore can photopolymerize even in the absence of initiators in reasonable polymerization times. In this embodiment, since the complex which absorbs the light is consumed by the polymerization, the polymer itself does not absorb light. Thus, polymerization can proceed to extremely great depths, and no potentially toxic initiator is required to initiate the polymerization. The polymer properties can be tailored by appropriate monomer choices since the products are regular, alternating copolymers. Nearly any unsaturated monomer can polymerize via this mechanism in the presence of a suitable polythiol and light.

In certain embodiment, thiol-ene polymers are made of two types of monomers. In specific embodiments, at least one of the two monomers is degradable. In certain embodiments, the monomers can be selected from poly(lactic acid) (PLA), polyglycolide (PGA), copolymers of PLA and PGA (PLGA), poly(vinyl alcohol) (PVA), poly(ethylene glycol) (PEG), poly(ethylene oxide), poly(ethylene oxide)-co-poly(propylene oxide) block copolymers (poloxamers, meroxapols), poloxamines, polyanhydrides, polyorthoesters, poly(hydroxy acids), polydioxanones, polycarbonates, polyaminocarbonates, poly(vinyl pyrrolidone), poly(ethyl oxazoline), carboxymethyl cellulose, hydroxyalkylated celluloses such as hydroxyethyl cellulose and methylhydroxypropyl cellulose, and natural polymers such as polypeptides, polysaccharides or carbohydrates such as polysucrose, hyaluronic acid, dextran and similar derivatives thereof, heparan sulfate, chondroitin sulfate, heparin, or alginate, and proteins such as gelatin, collagen, albumin, or ovalbumin, or copolymers, or blends thereof.

The monomers can vary in size depending upon desired properties for the resulting polymeric material. More particularly, the molecular weight for the monomers can range from about 30 DA to about 50000 Da. In certain embodiments, prior to formation of the polymeric material, the first and second monomers are derivatized to include thiol or olefin moieties such that they can participate in photoinitiated thiol-ene polymerization. For example, thiolated macromers such as poly(ethylene glycol) dithiol are available commercially. The olefin moieties can be selected from any suitable compound having a carbon double bond. For example, the olefin moiety can be selected from any suitable ethylenically unsaturated group such as vinyl, acetyl, vinyl ether, allyl, acrylate, methacrylate, maleimide, and norbornene. If each of the first and second monomers is derivatized with either two thiol or two olefin moieties, the resulting thiol-ene polymer would be a linear copolymer composed of alternating first and second monomer segments. However, in certain embodiments, the thiol-ene polymeric material is formed to contain cross-linking and branching. Thus, the derivatized monomer segments can have more than two thiol or olefin moieties per molecule that can participate in crosslinking and polymerization. The extent of the branching and crosslinking can be controlled by the use of differently derivatized first and second monomer segments and control over the concentration of the starting materials.

In certain embodiments, photoinitiation of the thiol-ene polymerization reaction with these monomeric, oligomeric or polymeric starting materials, high molecular weight, crosslinked networks are obtainable in the presence or absence of a chemical initiator within reasonable reaction times. This can eliminate the adverse effects of chemical initiators and still obtain rapid curing. Because of the step growth nature of the polymerization, these polymers have significantly lower glass transition temperatures and higher degrees of swelling than homopolymer diacrylate analogues. Thus, simple changes in molecular weight, number of functional groups, and the chemistry of the monomer between the functional groups allow facile control of the polymer properties over a wide range.

A biopolymer produced by a thiol-ene chemistry, including without limitation any of the chemistries disclosed herein, are provided herein.

3. Nucleophilic Addition Reaction

This disclosure also provides polymers formed by nucleophilic addition reaction. These types of polymers are described in U.S. Pat. No. 7,744,912, incorporated by reference, herein, in its entirety. The nucleophilic addition reaction system makes use of addition reactions, in which one monomer possesses a strong nucleophile and the other monomer possesses a conjugated unsaturation, or a conjugated unsaturation. In one embodiment, strong nucleophiles are thiols. In another embodiment, the system makes use of conjugate addition reactions between a thiol and a conjugated unsaturation (e.g., an acrylate or a quinone). This reaction system can be made to be self-selective, meaning substantially unreactive with other chemical groups found in most sensitive biological compounds of interest (most drugs, peptides, proteins, DNA, cells, cell aggregates, and tissues). It is particularly useful when one or both of these components is part of a polymer or oligomer, however other possibilities are also indicated herein.

Polyethylene glycol (PEG) provides a very convenient building block. One can readily purchase or synthesize linear (meaning with two ends) or branched (meaning more than two ends) PEGs and then functionalize the PEG end groups to introduce either a strong nucleophile, such as a thiol, or a conjugated structure, such as an acrylate or a quinone. When these components are either mixed with each other or are mixed with a corresponding component, a hydrogel material will form. One may react a PEG component with a non-PEG component, controlling the molecular weight or hydrophilicity of either component to manipulate the mechanical characteristics, the permeability, and the water content of the resulting biomaterial.

In the formation of biomaterials, especially biomaterials that are desired to degrade in vivo, peptides provide a very convenient building block. It is straightforward to synthesize peptides that contain two or more cysteine residues, and this component can then readily serve as the nucleophilic precursor component of a biomaterial, especially a hydrogel biomaterial. For example, a peptide with two free cysteine residues will readily form a hydrogel when mixed with a PEG triacrylate at physiological or slightly higher pH (e.g., 8 to 9; the gelation will also proceed well at even higher pH, but at the potential expense of self-selectivity). When the two liquid precursor components are mixed together, they react over a period of a few minutes to form an elastic gel, consisting of a network of PEG chains, bearing the nodes of the network, with the peptides as connecting links. The peptides can be selected as protease substrates, so as to make the network capable of being infiltrated and degraded by cells, much as they would do in a protein-based network. The gelation is self-selective, meaning the peptide reacts mostly with the PEG component and no other components, and the PEG component reacts mostly with the peptide and no other components; if desired, one can design and incorporate bifunctional agents to provide chemical bonding to other species (e.g., a tissue surface). These gels are operationally simple to form: one mixes two liquid precursors, one containing the peptide and the other containing the functionalized PEG. Because, in this example, physiological saline can serve as the solvent, and because minimal heat is generated by reaction, and because neither the PEG triacrylate nor the peptide can readily diffuse inside cells, the gelation can be carried out in vivo or in vitro, in direct contact with tissue, without untoward toxicity. It is clear that polymers other than PEG may be used, either telechelically modified or modified on their side groups.

As used herein, the symbol P is employed to indicate the part of a molecule that lies between two reactive sites (telechelic sense) or is grafted with reactive sites (grafted sense). With telechelic polymers, P will lie between two strong nucleophiles, such as two thiols, or between two conjugated unsaturations (e.g., in the case of a PEG diacrylate or a PEG dithiol, P is a PEG chain). In the case of a PEG triquinone or trithiol, P is a three-armed, branched PEG. In the case of a block copolymeric acrylate-(lactic acid oligomer)-PEG-(lactic acid oligomer)-acrylate or quinone-(lactic acid oligomer)-PEG-(lactic acid oligomer)-quinone, P is the (lactic acid oligomer)-PEG-(lactic acid oligomer) block copolymer. In the case of a graft copolymer (e.g., polylysine-graft-(PEG acrylate) or polylysine-graft-(PEG quinone) or polylysine-graft-(PEG thiol)), in which the geometry of the polymer is as a bottle-brush with the tips of the bristles containing either the conjugated unsaturations or the strong nucleophile, P is polylysine-graft-(PEG). P can also present the reactive groups in the side chains: every polymer bearing alcohols or amines in the side chains is easily acrylated, for example, in order to present multiple conjugated unsaturated groups for the conjugate addition reaction. Polymers containing carboxylic acids can be derivatized to expose, for example, quinines groups. P need not be polymeric in the usual sense of the word. For example, in the case of ethylene glycol diacrylate or diquinone, P is the ethylene unit. In the case of a peptide, for example, YCXXXXXXCY (SEQ ID NO: 1) or CXXXXXXC (SEQ ID NO: 2), where C is the amino acid cysteine and X and Y are other amino acids, such that XXXXXX (SEQ ID NO: 3) could be a sequence that functions as a substrate for a protease such as collagenase, P is XXXXXX (SEQ ID NO: 3). The length of XXXXXX (SEQ ID NO: 3) or the number of X (e.g., Xn) can be any length or number (n=0). In the case of 1,2 ethylene dithiol, P is the ethylene. Thus, P is the molecular part of the precursor component that is interposed between the two, or more, reactive groups on the precursor component. It is often convenient when this is polymeric or oligomeric, but neither case is necessary; small molecules are also of interest and use. Examples of small molecules which may be used include, but are not limited to reduced sugars or analogous compounds, such as mannitol, erythritol, pentaeritrol, trimethylol propane, and glycerol, which can be totally or partially acrylated, or reacted with beta-mercapto propionic acid to give thiols. Di- or multicarboxylic acids, such as EDTA, citric acid, succinic acid, and sebacic acid, can be converted to quinones.

A biopolymer produced by a nucleophilic addition reaction, including without limitation any of the chemistries disclosed herein, are provided herein.

Michael-Type Reaction

The 1,4 addition reaction of a nucleophile on a conjugate unsaturated system is referred to as a Michael-type reaction. The addition mechanism could be purely polar, or proceed through a radical-like intermediate state(s); Lewis acids or appropriately designed hydrogen bonding species can act as catalysts. The term conjugation can refer both to alternation of carbon-carbon, carbon-heteroatom or heteroatom-heteroatom multiple bonds with single bonds, or to the linking of a functional group to a macromolecule, such as a synthetic polymer or a protein. Double bonds spaced by a CH or $CH_2$ unit are referred to as homoconjugated double bonds.

Michael-type addition to conjugated unsaturated groups can take place in good to quantitative yields at room or body temperature and in mild conditions with a wide variety of nucleophiles. Conjugated unsaturated groups, such as vinyl sulfones, have been used to link PEG or polysaccharides to proteins through Michael-type reactions with amino- or mercapto-groups.

This type of chemistry allows for biocompatible gelling of biomaterial precursors to form a biomaterial is rapidly provided by the use of a wide variety of conjugated unsaturated compounds reacting with thiols in a self-selective manner. The gel formation kinetics and the mechanical and transport properties of the product are tailored to the needs of the application. Groups such as maleimides and vinylsulfones are useful in these cross-linking reactions, but these tend to be less useful than others because of a relatively high rate of reactivity with amines relative to other nucleophiles such as compared to some of the conjugated systems described below. As such, the use of conjugated unsaturations that display lower overall reactivity, including quinones and acrylates.

A biopolymer produced by a Michael-type reaction, including without limitation any of the chemistries disclosed herein, are provided herein.

Conjugated Unsaturated Structures

It is possible to perform Michael-type addition reactions on a wide variety of conjugated unsaturated compounds. In the structures shown below, an oligomeric or polymeric structure is indicated as P. Various possibilities for the specific identity of P are discussed further herein. P can be coupled to reactive conjugated unsaturated groups in structures such as those numbered 1 to 20.

In the drawings below, P is intended as terminated with a $CH_2$, CH or C group.

Reactive double bonds can be conjugated to one or more carbonyl groups in a linear ketone, ester or amide structure (1, 2) or to two in a ring system, as in a maleic or paraquinoid derivative (3, 4, 5, 6, 7, 8, 9, 10). In the latter case the ring can be fused to give a naphthoquinone (6, 7, 10) or a 4,7-benzimidazoledione (8) and the carbonyl groups can be converted to an oxime (9, 10). The double bond can be conjugated to a heteroatom-heteroatom double bond, such as a sulfone (11), a sulfoxide (12), a sulfonate or a sulfonamide (13), a phosphonate or phosphonamide (14). Finally, the double bond can be conjugated to an electron-poor aromatic system, such as a 4-vinylpirydinium ion (15). Triple bonds can be used in conjugation with carbonyl or heteroatom-based multiple bonds (16, 17, 18, 19, 20).

Chemical Structures:

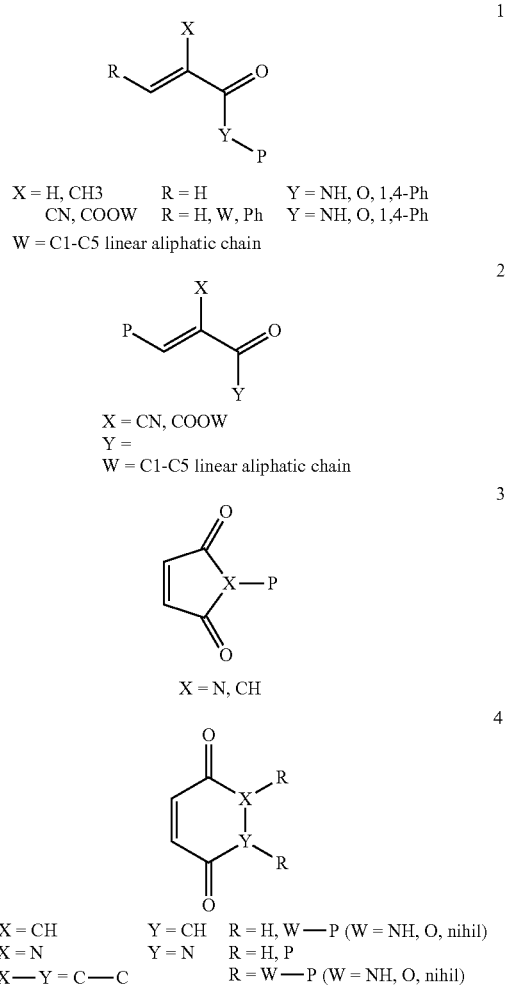

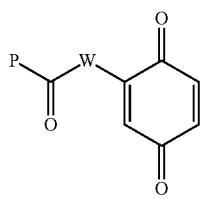

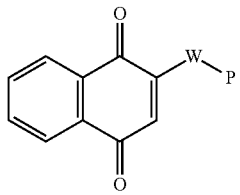

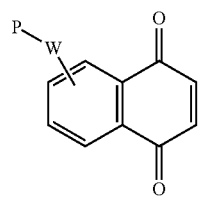

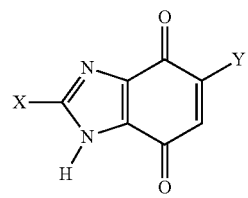

X, Y = H, P
P, P
P, H
P, aliphatic chain

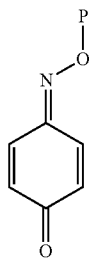

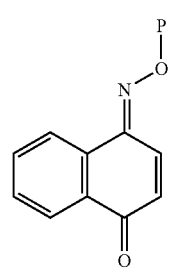

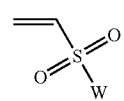

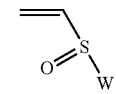

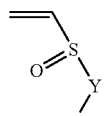

5

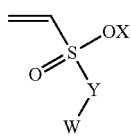

6

X = O, NH
X = alkali or alkali earth metal ion, P
W = P, 1,4-Ph—P

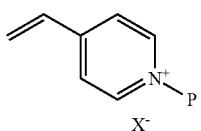

7

X = halogen, sulphonate

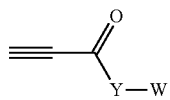

8

9

Y = O, NH
X = alkali or alkali earth metal Ion, P
W = P, 1,4-Ph—

Structures such as 1 and 2 are based on the conjugation of a carbon-carbon double bond with one or two electron-withdrawing groups. One of them is always a carbonyl, increasing the reactivity passing from an amide, to an ester, and then to a phenone structure. The nucleophilic addition is easier upon decreasing the steric hindrance, or increasing the electron-withdrawing power in the alpha-position: $CH_3<H<COOW<CN$.

The higher reactivity obtained by using the last two structures can be modulated by varying the bulkiness of the substituents in the beta-position, where the nucleophilic attack takes place; the reactivity decreases in the order $P<W<Ph<H$. So, the position of P too can be used to tune the reactivity towards nucleophiles. This family includes some compounds for which a great deal is known about their toxicology and use in medicine. For example, water-soluble polymers with acrylates and methacrylates on their termini are polymerized (by free radical mechanisms) in vivo, in hydrogel sealants and bone cements, respectively. Thus, acrylate and methacrylate-containing polymers have been seen in the body before in clinical products, but for use with a dramatically different chemical reaction scheme.

The structures 3-10 exhibit very high reactivity towards nucleophiles, due both to the cis configuration of the double bond and the presence of two electron-withdrawing groups.

Unsaturated ketones react faster than amides or imides, due to the stronger electronegativity of these carbonyl groups. So, cyclopentendione derivatives react faster than maleimidic ones (3), and para-quinones react faster than maleic hydrazides (4) and also faster than cyclohexanones, due to more extended conjugation. The highest reactivity is shown by naphthoquinones (7).

P can be placed in positions where it does not reduce the reactivity of the unsaturated group, that is in the opposite part of the ring (3, 5), on another ring (7, 8) or O-linked through a para-quinone mono-oxime (9, 10). P can be also linked to the reactive double bond (6, 8), if the nucleophilic addition rate is to be decreased.

The activation of double bonds to nucleophilic addition can be obtained also by using heteroatoms-based electron-withdrawing groups. In fact, heteroatom-containing analogous of ketones (11, 12), esters and amides (13, 14) provide a similar electronic behavior. Structures 13 and 14 can also be used as easily hydrolyzable groups that can promote quick gel degradation. The reactivity towards nucleophilic addition increases with electronegativity of the group, that is in the order 11>12>13>14, and is enhanced by the linkage with an aromatic ring. A strong activation of double bonds can also be obtained, using electron-withdrawing groups based on aromatic rings. Any aromatic structure containing a pyridinium-like cation (e.g., derivatives of quinoline, imidazole, pyrazine, pyrimidine, pyridazine, and similar $sp_2$-nitrogen containing compounds) strongly polarizes the double bond and makes possible quick Michael-type additions.

Carbon-carbon triple bonds, conjugated with carbon- or heteroatom-based electron-withdrawing groups, can easily react with sulphur nucleophiles, to give products from simple and double addition. The reactivity is influenced by the substituents, as for the double bond-containing analogous compounds.

The formation of ordered aggregates (liposomes, micelles) or the simple phase separation in water environment increases the local concentration of unsaturated groups and so the reaction rate. In this case, the latter depends also on the partition coefficient of the nucleophiles, which increases for molecules with enhanced lipophilic character.

Nucleophiles

The nucleophiles that are useful are those that are reactive towards conjugated unsaturated groups via addition reactions. The reactivity of the nucleophile depends on the identity of the unsaturated group, as discussed in more detail elsewhere herein, but the identity of the unsaturated group is first limited by its reaction with water at physiologic pH. Thus, the useful nucleophiles will generally be more nucleophilic than $H_2O$ at physiologic pH. Preferred nucleophiles will be ones that are commonly found in biological systems, for reasons of toxicology, but ones that are not commonly found free in biological systems outside of cells. Thus, while there may be examples in which amines can be employed as effective nucleophiles, the most preferred nucleophile is the thiol.

Thiols are present in biological systems outside of cells in paired form, as disulfide linkages. When the highest degree of self-selectivity is desired (e.g., when a therapeutic protein is incorporated, when the gelation reaction is conducted in the presence of tissue and chemical modification of that tissue is not desirable), then a thiol will represent the strong nucleophile of choice.

There are other situations, however, when the highest level of self-selectivity may not be necessary. This would include situations when no therapeutic protein is incorporated and when the gelation reaction is conducted in situ, but when chemical bonding to the tissue is either desirable or is not undesirable. In these cases, an amine may serve as an adequate nucleophile. Here, particular attention is paid to the pH, in that the deprotonated amine is a much stronger nucleophile than the protonated amine. Thus, for example, the alpha amine on a typical amino acid (pK as low as 8.8 for asparagine, average of 9.0 for all 20 common amino acids except proline) has a much lower pK than the side chain epsilon amine of lysine (pK 10.80). As such, if particular attention is paid to the pK of an amine used as the strong nucleophile, substantial self-selectivity can be obtained. Proteins have only one alpha amine (on the N-terminus). By selection of an amine with a low pK, and then formulation of the final precursor solution such that the pH were near that pK, one could favor reaction of the unsaturation provided with the amine provided, rather than other amines present in the system. In cases where no self-selectivity is desired, one need pay less attention to the pK of the amine used as the nucleophile, however in certain embodiments to obtain reaction rates that are acceptably fast one the pH of the final precursor solution should be adjusted such that an adequate number of these amines are deprotonated.

In summary, thiols are the preferred strong nucleophile of this embodiment, for reasons of pH in the precursor solution and maximal self-selectivity, but there are situations in which amines will also serve as useful strong nucleophiles; the usefulness of particular nucleophiles depends upon the situation envisioned and the amount of self-selectivity desired.

The concept of nucleophilic group is extended herein, so that the term is sometimes used to include not only the functional groups themselves (e.g., thiol or amine), but also molecules which contain the functional group (e.g., cysteine or cystyl residue, or lysine or lysyl residue).

The nucleophilic groups may be contained in molecules with great flexibility in overall structure. For example, a bifunctional nucleophile could be presented in the form of Nuc-P-Nuc, where P is used in the sense described herein and Nuc refers to the nucleophile. Likewise, a branched polymer P could be derivatized with a number of nucleophiles to create P-(Nuc)$_i$, where i=2 would be useful. Nuc needs not be displayed at the chain termini of P, for example, a repeating structure could be envisioned: (P-Nuc)$_i$, where i=2 would be useful. Clearly, not all of the P or the Nuc in such a structure need to be identical. It is only necessary that one nucleophilic precursor contain greater than or equal to two such Nuc groups.

Likewise, similar structures of P and the conjugated unsaturated groups described in detail above may be formed. It is only necessary that one conjugated unsaturated precursor contain greater than or equal to two such conjugated unsaturated groups.

It should be noted and understood that it is not necessary that both precursor components, for example, both the nucleophilic precursor component and the conjugated unsaturated precursor component, actually be polymeric in the usual sense of the word. It is only the functionality that matters. In practice, it is convenient if at least one component is polymeric in the usual sense of the word, but this is not absolutely necessary. For example, useful materials result from the reaction of a PEG triacrylate with dicysteine, and likewise, useful materials result from the reaction of a PEG trithiol and a low molecular weight diacrylate. Finally, useful materials for some applications also result from reaction of a dicysteine and a low molecular diacrylate.

In practice, it is convenient and useful when one or more precursor component is polymeric in the usual sense of the word. In these cases, P can be synthetic hydrophilic polymers, synthetic hydrophobic polymeric liquids, synthetic hydrophobic polymers that are soluble in solvents of acceptable toxicity or biological influence for the envisioned application, biosynthetic proteins or peptides, naturally occurring proteins or processed naturally occurring proteins, or polysaccharides.

Hydrophilic Polymers

In preferred embodiments, the synthetic polymer P can be poly(ethylene glycol), poly(ethylene oxide), poly(vinyl alcohol), poly(ethylene-co-vinyl alcohol), poly(acrylic acid), poly(ethylene-co-acrylic acid), poly(ethyloxazoline), poly(vinyl pyrrolidone), poly(ethylene-co-vinyl pyrrolidone), poly(maleic acid), poly(ethylene-co-maleic acid), poly(acrylamide), or poly(ethylene oxide)-co-poly(propylene oxide) block copolymers This is not an exhaustive list as other hydrophilic polymers could also be used.

P can also be copolymers, block copolymers, graft copolymers, or random copolymers. Blocks, which are polymerized on the ends of the hydrophilic polymers, can be composed of, for example, lactic acid, glycolic acid, epsilon-caprolactone, lactic-co-glycolic acid oligomers, trimethylene carbonate, anhydrides, and amino acids, for example, to confer degradability by hydrolytic or enzymatic means. This list is not exhaustive; other oligomers may also be used for block copolymers.

Random copolymers can be based on vinyl alcohol, such as poly(N-vinylpyrrolidone-co-vinyl alcohol) or poly(ethylene-co-vinyl alcohol), with different compositions, can be derivatized with conjugated unsaturated groups, such as acrylates, benzoquinones, naphthoquinones and others. The vinyl alcohol copolymers can be functionalized with $(CH_2)_n$, COOH groups by reaction with .omega.-bromo-carboxylic acids. The resulting polymers or acrylic or methacrylic acid copolymers can be used for the attachment of quinone groups. Comonomer composition and extent of functionalization do not influence dramatically the reaction rates, unless they determine solubility or phase transition. On the other hand, they determine the final mechanical properties.

It should be noted that one component P could even be a solid, such as a colloidal particle with either nucleophiles or sites of conjugated unsaturation upon it.

Proteins and Biosynthetic Proteins

P may be a protein. The protein can be a naturally occurring or recombinant protein. In general terms, the recombinant proteins are any length amino acid material generated through recombinant DNA technology. Examples of components these can have include peptide sequences which encode degradation sites for proteases, peptide sequences for other biological signals and non biointeractive sequences.

Any naturally occurring protein can also be P. More specifically, a naturally occurring protein is composed of several Ps which are separated by nucleophiles. For example, serum albumin, a 584 amino acid protein, contains 5.7% cysteine, 9.9% lysine and 3.1% tyrosine. The amino acid sequences which occur between, for example, cysteine, tyrosine and lysine make up distinct Ps. While albumin in its natural state may be less than useful for the purposes of cross-linking by conjugate addition reactions between conjugated unsaturations and thiols on the protein, albumin can be readily processed by reduction so as to form a poly(amino acid) with some or all of its cysteine residues free or it can be chemically derivatized to introduce multiple thiol groups.

Peptides

In some instances, P may be a peptide or a polypeptide, where the nucleophile is the amino acid cysteine, resulting in peptides of structures similar to H$_2$N—CXXXXX-CXXXXXC-COOH (SEQ ID NO: 4) or H$_2$N—CXXXXXC-COOH (SEQ ID NO: 5), where C is the one-letter representation of cysteine, and X represents any amino acid except cysteine, in one embodiment, or Acetyl-NH—YXXXXXYXXXXXY-COOH (SEQ ID NO: 6) where Y is the one-letter representation of tyrosine, and X represents any amino acid except cysteine or tyrosine, in another embodiment. The length of XXXXX (SEQ ID NO: 7) or the number of X (e.g., Xn) can be any length or number (n=0). It is particularly useful when the sequences in the domains shown as XXXXX (SEQ ID NO: 7) above are substrates for enzymes that are involved in cell migration (e.g., as substrates for enzymes such as collagenase, plasmin or elastase), although the domains need not be limited to these. One such particularly useful sequence, as a substrate for the enzyme plasmin, is described in the examples. A variety of such peptides may be learned from a study of the literature of these enzymes. For example, such a study shows substrate sites for the important protease plasmin (Table 1; SEQ ID NOS: 8-24, where sequences are read horizontally, e.g., SEQ ID NO. 8 is understood to be GPRVVE):

TABLE 1

Plasmin Substrate Sites found in Fibrin (ogen) (Fg)**

| P3 | P2 | P1 | P1' | P2' | P3' | Fg chain and site | Reference |
|----|----|----|-----|-----|-----|-------------------|-----------|
| Arginyl Sites | | | | | | | |
| G | P | R+ | V* | V* | E− | α 19 | 3 |
| N | N | R+ | D− | N | T | α 104 | 2, 4 |
| Y | N | R+ | V* | S | E− | α_110 | 2 |
| Q | M* | R+ | M* | E− | L* | | 1 |
| G | F* | R+ | H+ | R+ | H+ | α 491 | 5 |
| G | Y | R+ | A* | R+ | P | β 42 | 2, 3 |
| Lysyl Sites | | | | | | | |
| Y | Q | K+ | N | N | K+ | α_78 | 3 |
| L* | I* | K+ | M* | K+ | P | α 206 | 1, 2 |
| N | F* | K+ | S | Q | L* | α_219 | 1 |
| E− | W | K+ | A* | L* | T | α_230 | 1 |
| S | Y | K+ | M* | A* | D | α_583 | 5 |
| T | Q | K+ | K+ | V* | E− | β_53 | 3 |
| R+ | Q | K+ | Q | V* | K+ | β_130 | 2 |
| Q | V* | K+ | D− | N | E− | β_133 | 4 |
| L* | I* | K+ | A* | I* | Q | γ_62 | 4 |
| T | L* | K+ | S | R+ | K+ | γ_85 | 2, 3 |
| S | R+ | K+ | M* | L* | E− | γ_88 | 2 |

Ref. 1: Takagi T. and R. F. Doolittle, Biochemistry 14: 5149-5156, 1975; Ref. 2: Hantgan R. R., et al., Hemostasis and Thrombosis: Basic Principles and Clinical Practice, Third Edition. Edited by R. W. Colman et al. J. B. Lippencott Company: Philadelphia, 1994; Ref. 3: Takagi T. and R. F. Doolittle, supra.; Ref. 4: Nomura S. et al., Electrophoresis 14: 1318-1321 1993.; Ref. 5: Ständker L. et al., Biochemical and Biophysical Research Communications 215: 896-902 (1995).
*Indicates a hydrophobic amino acid; +/− Indicates a charged side chain, either cationic (+) or anionic (−).
**Single letter amino acid code: A, alanine; C, cysteine; D, aspartic acid; E, glutamic acid; F, phenylalanine; G, glycine; H, histidine; I, isoleucine; K, lysine; M, methionine; N, asparagine; P, proline; Q, glutamine; R, arginine; S, serine; T, threonine; V, valine; W, tryptophan; Y, tyrosine.

Given that plasmin is an important enzyme in cell migration and tissue/clot remodeling, these substrates or parts of these substrates represent useful sequences within the sites indicated above as XXXXX (SEQ ID NO: 7) in P.

Likewise, collagenase is an important enzyme in cell migration and tissue remodeling. A study of the literature on collagenase indicates also a variety of substrate sites, which represent useful identities for XXXXX (SEQ ID NO: 7) in P (Table 2; SEQ ID NOS: 25-31, where sequences are read horizontally, e.g., SEQ ID NO. 25 is understood to be PQGIAG):

TABLE 2

Collagenase Substrate Sites found in Collagen

| P3 | P2 | P1 | P1' | P2' | P3' | Collagen type and site | Ref. |
|---|---|---|---|---|---|---|---|
| P | Q | G | I* | A* | G | calf & chick α 1 (I); human cartilage α 1 (II) | 6 |
| P | Q | G | L* | L* | G | calf α 2 (I) | 6 |
| P | Q | G | I* | L* | G | chick α 2 (I) | 6 |
| P | Q | G | L* | A* | G | chick α 1 (I); human skin α 1 (III) | 6 |
| P | L* | G | I* | A* | G | human liver α 1 (III) | 6 |
| P | L* | G | L* | W | A* | human | 7 |
| P | L* | G | L* | A* | G | human | 8 |

Ref. 6: Netzel-Arnett S. et al., The Journal of Biological Chemistry 266: 6747-6755, 1991; Ref. 7: Upadhye S. and V. S. Ananthanarayanan, Biochemical Biophysical Research Communications 215: 474-482, 1995; Ref. 8: Liko Z., et al., Biochem Biophys Res Commun 227: 351-35, 1996.

The use of enzyme degradation sites within P, either in the nucleophile precursor component (most easy, since cysteine in the sequence may be used to provide a thiol as a nucleophile) or as the conjugated unsaturated precursor component, is that the rate of biomaterial resorption or remodeling may be linked to the rate and progress of healing, for example, as indicated by cell infiltration.

It is particularly powerful to note that the rate of biomaterial resorption may be modulated by adjustments to the oligopeptide sequence so as to alter the $K_m$ and $k_{cat}$ of the substrate site. For example, a study of the literature on the enzymology of collagenase substrate sites shows that it is possible to adjust the rate of degradation of substrates by the design of the sequence of the substrates (Table 3; SEQ ID NOS: 32-38, where sequences are read horizontally, e.g., SEQ ID NO. 32 is understood to be GPQGIAGQ):

TABLE 3

Design of Collagenase (Matrix metalloproteinase I)-Sensitive Peptide Sequences

| No. | Sequence | $k_{cat}/K_m$ relative to that of PQGIAG |
|---|---|---|
| 1 | GPQGIAGQ | 100% (normal) |
| 2 | GPVGIAGQ | 30% (slow) |
| 3 | GPQGVAGQ | 9% (slower) |
| 4 | GPQGRAGQ | <5% (very slow) |
| 5 | GPQTIASQ | 130% (fast) |
| 6 | GPQGIFGQ | >300% (faster) |
| 7 | GPQGIWGQ | >700% (very fast) |

Netzel-Arnett S. et al., The Journal of Biological Chemistry 266: 6747-6755, 1991

Polymer Network Formation
a. Functionality

Utilizing terminology from polymer science, polymers can be made by reaction of monomers with a functionality of 2. Cross-linked networks of polymers can be made if some or all of the monomers have a functionality greater than 2. Molecules are described herein having a functionality greater than or equal to 2 (monomers or macromers), which can be reacted together to form a cross-linked network, where functionality is defined in terms of addition reactions. As used herein, polymerization refers to the reaction of monomers or macromers with functionality of 2, and cross-linking refers to the reaction of monomers or macromers some or all of which have a functionality greater than 2.

The monomers described are of two classes, which when reacted together form a linear or cross-linked biomaterial. Both classes of monomers are required to be mixed together for cross-linking to occur (different approaches for mixing are described immediately below). One class of monomer contains 2 or more conjugated unsaturated groups (thus, a functionality of 2 or more), preferably conjugated. The other class of monomer contains 2 or more nucleophiles (thus, a functionality of 2 or more), preferably nucleophiles that are stronger nucleophiles than others present as other components of the system, for example, thiols when compared with amines that may be present as desirably non-reactive components of the system.

When water-soluble precursor monomers are mixed together (referred to as the final precursor solution), linear or cross-linked gels or networks are formed, and such reactions can proceed in water at physiologic or nearly physiologic salt concentrations and pH. It is not necessary that the monomers be entirely soluble in water, and indeed it is sometimes beneficial that they not be soluble in water. In such cases, gels may not be obtained as the final material, but rather more hydrophobic, less water-swelling materials. These can be particularly useful in the delivery of hydrophobic drugs and in the formation of materials with substantial structural strength. It is only necessary that the two components be either soluble in each other or at least finely dispersible in each other, perhaps in the presence of an emulsifying agent. In this manner, the two components can come close enough to each other to react to form the linear or cross-linked material.

It is also possible to work with solutions of monomers formed in a solution other than water. For example, the use of N-methylpyrrolidone (NMP) as a solvent in injectable biomaterial systems is known, and as such it is possible, when one wishes to work with the precursor components in solution, but with precursor components that are not freely soluble in water, to employ certain organic solvents that are acceptable for use with the sensitive biological material under consideration.

When a drug is being incorporated in the laboratory or in a manufacturing line, then there is great flexibility in the selection of this organic solvent, since at least most of it will be removed before the implant is provided to the subject. When a material is being formed on the skin, then a great deal of flexibility also exists, due to the low skin toxicity of many organic solvents, including NMP, acetone, ethanol, isopropanol and ethyl acetate. When a material is being formed in the body, then the list of acceptable solvents is considerably smaller and is dominated by toxicity concerns. In such cases, NMP is a particularly favorable organic solvent. The toxicity of the solvent system can also be modulated by employing a mixed solvent system, comprising the organic solvent and water, to lower the overall concentration of organic solvent but to still provide good solubility or dispersability in the mixed solvent system.

Mixing to form the final precursor solution can occur by several means. Most straightforwardly, one solution contains the nucleophilic precursor component and one solution contains the conjugated unsaturated precursor component. These two components are formulated in solvent and buffer systems such that the pH and concentrations obtained after mixing are appropriate for the chemical reaction to proceed. Such mixing could occur in a static mixer at the function of two syringes, for example.

Other mixing approaches can be imagined. For example, mixing can occur between fine particles of each of the two precursor solutions in an air spray. One solution could be prepared from both precursor components, but at a pH, for example, such that the reaction did not proceed or proceeded only slowly. After placement of the pre-mixed precursor solution, pH could be adjusted (e.g., by change of temperature, or mixing with acid or base, or by a chemical reaction to create an acid or base, or diffusion of an acid or base), to result in a final condition in the final precursor solution that was appropriate for the chemical reaction to proceed. Another approach can be to prepare the final precursor solution at a temperature such that the reaction did not proceed or proceeded only very slowly, either related to the activation energy of the reaction or to a buffer with temperature-sensitive characteristics or both. Upon warming or cooling (most usefully warming) to the final application temperature (e.g., to body temperature after injection), the conditions in the final precursor solution would be appropriate for the chemical reaction to proceed.

Medical Applications

Since the biomaterials are useful as medical implants or devices, or for drug delivery in humans, in certain embodiments the system of molecules used in the precursor solution should meet certain criteria. According to these specific embodiments, the criteria include:

1. The rate of the Michael-type reaction should occur over a clinically relevant period of time at a clinically relevant temperature and pH. Generally, gelation over a period of less than approximately 15 minutes, at a pH generally more than 7 and less than 9 and at a temperature greater than 25 and less than 40° C. is desirable.

2. The reaction should be sufficiently self-selective, with self-selectivity considerations including the following. For the formation of gels in the presence of drugs containing amines or where reaction with cell and tissue components is undesirable, the conjugated unsaturation should react very slowly with amines at the pH of application of the final precursor solution. Preferably, a ratio of reactivity of the conjugated unsaturation for the nucleophile of intentional reactivity to the amine, in this case the nucleophile of unintentional or undesirable reactivity, in excess of ten and more preferably even higher is desired. Typically, the approach of Michael-type addition between conjugated unsaturations and thiols will not be useful for drugs that contain themselves conjugate unsaturations or thiols. Exceptions include cases when the reactivity of the group on the drug is considerably less than the reactivity on the corresponding group in the biomaterial precursor and cases when such reactions are not detrimental, for example, when grafting to the biomaterial network are not detrimental.

3. The reactants should be stable in water, when the precursor solutions are prepared in water. Stable is defined as reacting slowly, with slowly defined as sufficiently slow to allow the reaction between the two components to proceed and still result in the formation of the desired biomaterial.

4. The addition reaction in the final precursor solution should not be exothermic to the point of causing tissue damage, drug breakdown or other detrimental results to the biological material under consideration. The temperature of the gelling solution generally should not be raised above 60° C. during gelation, and preferably even cooler maximum reaction temperatures are desirable.

5. The components of the precursor solution should not be toxic at concentrations which diffuse out of the final precursor solution as it is applied, with the word toxic being defined as inducing a medically unacceptable tissue reaction in a medically relevant context.

The criteria defined above in this section limit the identity of the molecules which may be useful in the precursor solution, by limiting the identity of the chemical group used for the cross-linking.

4. Additional Crosslinking Chemistries for Step-Growth Networks.

Crosslinking chemistries disclosed in Sections 1 through 3 result in formation of polymeric networks via a step-growth mechanism and may be extended to include other types of chemical reactions that are known in the art. These may include, without limitation, the following reactions between monomers bearing general classes of reactive moieties R1 and R2:

Disulfide exchange between thiol moiety (R1) and disulfide, e.g. pyridyl disulfide moiety or 5-thio 2-nitrobenzoic acid-thiol derivative (R2)

Alkylation reaction between thiol moiety (R1) and alkyl halide moiety (R2), e.g. iodoacetamide or alpha-bromoketone to yield thioester Nucleophilic substitution between amine moiety (R1) and activated ester (R2), e.g. N-hydroxysuccinimide-activated ester to yield amide Nucleophilic substitution between amine moiety (R1) and sulfonyl chloride (R2) to yield sulfonamide Nucleophilic addition between amine moiety (R1) and isocyanate moiety or isothiocyanate moiety (R2) to yield substituted urea or substituted thiourea, respectively Condensation reaction between aminooxy moiety (R1) and aldehyde or ketone (R2) to form oxime Condensation reaction between aminooxy moiety (R1) and hydrazide moiety (R2) to form hydrazine Staudinger ligation between azide moiety (R1) and ester- or thioester-containing triarylphosphine moiety (R2) to form amide

[3+2] cycloaddition between azide moiety (R1) and alkyne moiety (R2) to form triazole

[3+2] cycloaddition between azide moiety (R1) and oxanorbornadiene moiety (R2), to yield triazole Inverse-demand Diels-Alder reaction between tetrazine moiety (R1) and activated olefin moiety (R2), e.g. trans-cyclooctene or norbornene, to yield ligation product Photoinduced 1,3-dipolar cycloaddition between alkene moiety (R1) and tetrazole moiety (R2) to yield pyrazoline Ruthenium-catalyzed cross-metathesis between alkene moiety (R1) and alkene moiety (R2) to yield ligation product Non-covalent association between biotin moiety (R1) and avidin or streptavidin moiety (R2)

Non-covalent association between antibody (R1) and antigen (R2)

Trans-splicing reaction between split intein moieties (R1 and R2)

Trans-splicing or ligation reaction between nucleic acid moieties (R1 and R2)

Non-covalent association between oligonucleotide (R1) and its complementary sequence (R2)

Non-covalent association between aptamer (R1) and its target (R2)

Non-covalent association between cognate nucleic acid motifs, e.g. tetraloop (R1) and tetraloop receptor (R2)

Non-covalent association between a nucleic-acid-binding protein (R1) and its cognate nucleic acid motif (R2), for example between spliceosomal protein U1A and its cognate RNA structure The monomers that can be employed with the above chemistries are the same as the monomers provided for other chemistries listed in the current application and can vary in size depending upon desired properties for the resulting polymeric material. More particularly, the molecular weight for the monomers can range from about 30 Da to about 50000 Da. In certain embodiments, prior to formation of the polymeric material, the first and second monomers are derivatized to include moiety R1 or moiety R2 by conjugation techniques well-known in the art, such that they can participate in a specific reaction disclosed above.

5. Materials Generated by Chain Polymerization.

Alternatively to the step growth polymerization mechanisms disclosed in Section 1 through 4, the polymer scaffolds may be created by polymerizations proceeding via chain growth mechanism.

Chain-growth polymerization is a polymerization technique where unsaturated monomer molecules add onto the active site on a growing polymer chain one at a time. In one embodiment, the chain growth polymerization is a radical-mediated polymerization of olefin functional groups, where olefin groups are provided, for example, by allyl ethers, vinyl ethers, acrylates, methacrylates, hydroxymethylacrylates, acrylamides or other moieties containing unsaturated carbon-carbon bonds. Radicals may be generated by redox, thermal, enzymatic or photochemical mechanisms, as disclosed in Sections 1 and 2.

For polymerization to occur, each olefin-containing component should have at least one olefin functional group, (i.e. the monomer should contain one or more double bonds). Polymerization of a mono-functional olefin results in the formation of a linear polymer, rather than a crosslinked polymer. Crosslinked gels can be readily formed by increasing the functionality, i.e., increasing the degree of substitution of the monomer to be greater than one. In one embodiment, linear or branched monomer with two or more olefin moieties is polymerized to form a crosslinked network. In another embodiment, networks with different crosslinking densities are created by copolymerization of various molar ratios of mono-substituted monomer (e.g. single olefin per monomer) and another monomer with a degree of substitution of two or more (two or more olefin moieties per monomer). In yet another embodiment, networks of different mesh size are created by polymerizing monomers with two or more olefin moieties per monomer and different molecular weight of the monomer between olefin moieties, for example by polymerizing linear PEG di(meth)acrylates of different molecular weights.

In certain embodiments, the monomers can be selected from poly(lactic acid) (PLA), polyglycolide (PGA), copolymers of PLA and PGA (PLGA), poly(vinyl alcohol) (PVA), poly(ethylene glycol) (PEG), poly(ethylene oxide), poly(ethylene oxide)-co-poly(propylene oxide) block copolymers (poloxamers, meroxapols), poloxamines, polyanhydrides, polyorthoesters, poly(hydroxy acids), polydioxanones, polycarbonates, polyaminocarbonates, poly(vinyl pyrrolidone), poly(ethyl oxazoline), carboxymethyl cellulose), hydroxyalkylated celluloses such as hydroxyethyl cellulose and methylhydroxypropyl cellulose, and natural polymers such as polypeptides, polysaccharides or carbohydrates such as polysucrose, hyaluronic acid, dextran and similar derivatives thereof, heparan sulfate, chondroitin sulfate, heparin, or alginate, and proteins such as gelatin, collagen, albumin, or ovalbumin, fibrinogen, fibrin, laminin, fibronectin, vitronectin, or fragments, copolymers, or blends thereof.

The monomers can vary in size depending upon desired properties for the resulting polymeric material. More particularly, the molecular weight for the monomers can range from about 30 Da to about 100000 Da. In certain embodiments, prior to formation of the polymeric material, the monomers are derivatized to include olefin moieties such that they can participate in chain-growth polymerization. For example, acrylated monomers such as poly(ethylene glycol) diacrylate are available commercially. The olefin moieties can be selected from any suitable compound having a carbon double bond. For example, the olefin moiety can be selected from any suitable ethylenically unsaturated group such as vinyl, vinyl ether, allyl, acrylate, methacrylate or maleimide.

Non-Traditional Biomaterial Approach

A commonly held belief in the field of tissue engineering is that biomaterials used for research and/or medical applications should be designed to have physical properties that are as close to native tissues as possible. That is, the design of biomaterials for applications involving the generation of bone and cartilage should attempt to recapitulate the stiff physical properties of these tissues and the design of biomaterials for applications involving the generation of soft tissues like skin should attempt to mimic the soft physical properties of these tissues. The rationale behind this approach, which finds considerable support in published literature, is that providing cells with a physical environment that is as close to their native environment as possible, will promote the desired cell behavior and tissue formation.

The preferred embodiment of this application, however, describes a PEG-based polymer system in which the final weight percent of the PEG monomers is 2% wt/vol and forms a biomaterial that is significantly softer than most bodily tissues. Initial efforts to use biomaterial formulations that mimicked the stiffness and elasticity of skin for full-thickness skin wound healing applications failed to result in adequate cellular infiltration from the surrounding tissues. As a result, these biomaterial formulations actually slowed tissue regeneration and wound healing. In contrast, biomaterial formulations that were significantly softer than normal skin performed better in this full-thickness wound model, leading to the formulation that is now the preferred embodiment of this application. It is foreseen that the same will be true for other tissue repair/regeneration applications and that the design of biomaterials that facilitate and promote cellular infiltration from the surrounding tissues will be more effective that biomaterials that aim to recapitulate the physical properties of the target tissue.

Of significant value to the current application, the use of biomaterials that are composed of monomers with relatively low molecular weights at low weight percents eliminates undesired aggregation/precipitation effects of blood extracts. As described previously, larger monomers and higher monomer concentrations can cause the aggregation/precipitation of proteins found in blood extracts. The ability to create uniform polymer networks at low concentrations of monomers is a particular advantage of step-growth polymerizations.

Methods of Use

A method of administering a blood extract to a damaged site on an individual is provided, wherein the method comprises delivering to the damaged site a composition comprising (i) a biomaterial or a precursor to a biomaterial and (ii) a blood extract. In one aspect, the method comprises administering (i) a biomaterial and (ii) a blood extract. In another aspect, the method comprises administering (i) a precursor to a biomaterial (e.g., one or more monomers that, upon polymerization, form a polymeric biomaterial) and (ii) a blood extract. In one aspect the blood extract is autologous. In another aspect, the blood extract is allogenic or xenogenic.

Although it is understood that the (i) biomaterial or a precursor to a biomaterial and (ii) blood extract, when contained within the same composition are administered to the individual concurrently, the invention also encompasses a method of administering a blood extract to a damaged site on an individual, wherein the method comprises delivering to the damaged site (i) a biomaterial or a precursor to a biomaterial and (ii) a blood extract, wherein the (i) biomaterial or a precursor to a biomaterial and (ii) blood extract may be administered to the damaged site concurrently, separately or sequentially. In one such embodiment, the biomaterial or a precursor to a biomaterial is administered to the damaged site prior to or after administration of the blood extract to the damaged site, provided that administration of the biomaterial or a precursor to a biomaterial occurs no more than about any of 60, 45, 30, 25, 20, 15, 10, 5 or 3 minutes between administration of the blood extract. In one aspect the blood extract is autologous. In another aspect, the blood extract is allogenic or xenogenic.

In one aspect is provided a method of delivering a blood extract to a subject in need thereof comprising providing a blood extract; providing a one or more monomers; mixing the blood extract with the one or more monomers; polymerizing the one or more monomers to form a polymer, wherein the blood extract is integrated within the polymer, and administering the polymer to the subject in need thereof. In certain embodiments, the biomaterial is polymerized at the time of or after the monomers have been placed at the site of the defect. Accordingly, also provided is a method of delivering a blood extract to a subject in need thereof comprising providing a blood extract; providing a one or more monomers; mixing the blood extract with the one or more monomers; and administering a composition comprising the one or more monomers and the blood extract to the subject in need thereof. The method may further comprise polymerizing the one or more monomers to form a polymer in situ (e.g., at a damaged area such as a wound). In one aspect the blood extract is autologous. In another aspect, the blood extract is allogenic or xenogenic.

This disclosure also provides a method of treating a skin wound, orthopedic condition, pain, nerve injury, tendinitis, osteoarthritis, cardiac muscle injury, bone injury, traumatic injury or dental injury comprising administering to a subject in need thereof any of the compositions described herein, such as a composition comprising a biomaterial or a precursor to a biomaterial, and wherein the composition optionally comprises a blood extract. In one aspect the blood extract is autologous. In another aspect, the blood extract is allogenic or xenogenic. The compositions may also be used in a method of treating a sports injury, healing an injured bone or healing post-surgical wounds.

The disclosure also provides a method of treating a skin wound, orthopedic condition, pain, nerve injury, tendinitis, osteoarthritis, cardiac muscle injury, bone injury, traumatic injury or dental injury including the steps of administering to a subject in need thereof one or more monomers mixed with a blood extract; and polymerizing the monomers to form a polymer; thereby treating the subject in need thereof. In one aspect the blood extract is autologous. In another aspect, the blood extract is allogenic or xenogenic. The compositions may also be used in a method of treating a sports injury, healing an injured bone or healing post-surgical wounds.

Also provided is a method of slowing the activation of a blood extract administered to a subject in need thereof comprising administering to a subject in need thereof any of the compositions described herein. In one aspect the blood extract is autologous. In another aspect, the blood extract is allogenic or xenogenic.

A method of delivering PRP to a subject in need thereof is also provided, wherein the method comprises providing PRP; providing a one or more monomers; mixing the PRP with the one or more monomers; polymerizing the one or more monomers to form a polymer, wherein the PRP is integrated within the polymer; and administering the polymer to the subject in need thereof. Another method of delivering PRP to a subject in need thereof comprises administering to a subject in need therein a composition comprising a biomaterial or a precursor to a biomaterial (e.g., one or more monomers) and PRP. When the method comprises administering a precursor to a polymeric material (e.g., one or more monomers), the method may further comprise polymerizing the one or more monomers to form a polymeric biomaterial.

Also provided is a method of providing a synthetic polymeric scaffold to a damaged area on an individual in need thereof, wherein the method comprises administering to the damaged area a polymeric biomaterial or a precursor to a polymeric material, wherein the precursor to a polymeric material (e.g., one or more monomers) may, upon application to the damaged area, be polymerized in situ to form a polymeric biomaterial. In another aspect is provided a method of conforming a synthetic polymeric scaffold to the size and shape of a damaged area, wherein the method comprises administering to the damaged area a precursor to a polymeric material, wherein the precursor to a polymeric material (e.g., one or more monomers) may, upon application to the damaged area, be polymerized in situ to form a polymeric biomaterial. In one aspect, the polymeric material, which is either administered to the damaged area or is polymerized in situ upon administration of a precursor to a polymeric material to the damaged area, conforms to one or more of the following features: (a) the polymeric biomaterial is a fully synthetic, consistent and reproducible scaffold that is not reliant on the properties of a clot for repair of the damaged area; (b) the polymeric biomaterial is capable of releasing growth factors at the damaged area throughout the healing process; (c) the polymeric biomaterial degrades as the damaged area heals (e.g., as new tissue or bone is formed); (d) the polymeric material produces well defined degradation products in vivo; (e) the polymeric biomaterial is capable of being rapidly formed in situ and (f) when produced in situ (at the site of the defect) the polymeric biomaterial forms a contiguous boundary with the edges of the defect. The method may further comprise administering (either concurrently, separately or sequentially) a blood extract to the individual, where the blood extract may be autologous, allogenic or xenogenic.

In one aspect of any of the provided methods, the damaged area is a wound. In another aspect of any of the provided methods, the damaged area is damaged bone. In one aspect of any of the provided methods, the individual is a human. In one variation of any of the provided methods, a polymeric biomaterial is delivered to the damaged area. In a further aspect of any of the provided methods, the polymeric biomaterial delivered to the damaged area comprises an organosulfur moiety (—C—S—C—). In another variation of any of the provided methods, a precursor to a polymeric biomaterial, such as one or more monomers (which may be the same or different) is delivered to the damaged area and the polymeric biomaterial is produced in situ from the precursor. Thus, in one aspect of a method that utilizes delivery of a precursor to a polymeric biomaterial (e.g., delivery of one or more monomers), the method further comprises polymerizing the precursor in situ at the damaged site. In another variation of any of the provided methods, a precursor to a polymeric biomaterial, such as one or more monomers (which may be the same or different) is delivered to the damaged area in combination with a blood extract, and the polymeric biomaterial is produced in situ from the precursor. When delivered in combination with a blood extract, the method may comprise delivering the precursor to a polymeric biomaterial concurrently with the blood extract, e.g., by mixing the precursor with the blood extract and delivering the mixture to the individual (e.g., to the damaged site, such as a wound). When delivered in combination with a blood extract, the method may also comprise delivering to an individual (e.g., to the damaged site of an individual, such as a wound) the precursor to a polymeric biomaterial prior to, at the same time as, or after delivery of a blood extract to the individual (e.g., to the damaged site of an individual, such as a wound), wherein the precursor and the blood extract are administered to the individual no more than about any of 60, 45, 30, 25, 20, 15, 10, 5, 3 or 2 minutes apart.

In one aspect of any of the provided methods, the precursor to a polymeric biomaterial (e.g., that is delivered to the damaged area) comprises a first monomer having a thiol moiety and a second monomer having an alkene or alkyne moiety. In one aspect of such a method, the first monomer comprising a thiol moiety is a monomer comprising a cysteine residue, such as a moiety comprising a peptide in which a cysteine residue is included, and the second monomer is a monomer comprising a norbornene moiety, such as a PEG monomer derivatized with norbornene. In any of these methods, in one aspect, the method has one or more of the following attributes: (a) the method is rapidly performed at the site of the intended use; (b) the method uses only standard and readily available equipment and personnel; and (c) the method does not require the use of conditions that can substantially alter the activity of growth factors or other proteins in a blood extract.

Methods of Making

Also provided herein are methods of making a biomaterial. A biomaterial product produced by the processes detailed herein (including in the accompanying examples or in any of the chemistries described herein above) is also included. Methods of making a composition comprising a biomaterial or a precursor thereof are also provided. A biomaterial product or biomaterial precursor product produced by a described method (e.g., by a described chemistry) is also provided. Thus, a composition or method herein may be described as containing or using a product made by a given process. All such products (and processes) are included herein the same as if each product were specifically and individually listed as a product made by the given process. Methods of making a composition are also provided, such as a method of combining a biomaterial or precursor thereof (e.g., a polymeric biomaterial precursor) with a carrier (e.g., an aqueous carrier), wherein the method may optionally include combining the biopolymer or precursor thereof with one or more additional agents such as an additional therapeutic agent and/or photoinitiator).

Kits

Kits comprising a composition provided herein (e.g., a composition comprising a biomaterial or a precursor to a biomaterial and optional additional agents, such as an additional therapeutic agent) are also provided. In one aspect, the kit comprises instructions for use in the treatment of an injury, such as a wound.

Any composition detailed herein above and throughout may be used in the kits, the same as if each and every composition were specifically and individually listed for use in a kit. For example, it is understood that a kit comprising a first monomer and a second monomer, wherein the first monomer comprises a thiol moiety (such as a monomer comprising a cysteine residue, for example, a peptide having at least one cysteine) and wherein the second monomer is a monomer comprising a norbornene moiety, such as a PEG monomer derivatized with norbornene is provided. The kit may optionally include instructions, such as for the use in treating an injury, such as a wound. The kit may include additional components relating to the treatment, such as a container suitable for collecting or storing a blood extract from an individual, and an applicator, such as a needle and/or syringe, for combining the biomaterial or precursor thereof with the blood extract and delivering the mixture thereof to the desired site on the individual (such as a wound).

Articles of Manufacture

Articles of manufacture comprising a container in which a composition provided herein (e.g., a polymeric biomaterial composition or a composition comprising a precursor to a polymeric biomaterial such as one or more mutually reactive monomers) is contained are provided. The article of manufacture may be a bottle, vial (including a sealed or sealable tube), ampoule, single-use disposable applicator, syringe, or the like. The container may be formed from a variety of materials, such as glass or plastic and in one aspect also contains a label on, or associated with, the container which indicates directions for use in the treatment of an indication provided herein, such as healing a wound.

In one aspect, the container is a medical device containing a unit dosage form of a composition provided herein. The device may contain an applicator for applying the composition to a damaged site on an individual (e.g., a wound). Alternatively, a container (e.g., a bottle, vial or ampoule) may be packaged together with, or provided with instructions for use in conjunction with, a needle and/or syringe which is used to dispense the composition from the container to the desired site (e.g., to the wound). In one aspect, an article of manufacture comprising a biomaterial (e.g., a polymeric step-growth biomaterial) or a precursor to a biomaterial (e.g., monomeric precursors that, upon polymerization, produce a step-growth polymeric biomaterial) are packaged together with a second container suitable for obtaining or storing a blood extract from an individual. Upon collection of a blood extract from an individual into the second container, the article of manufacture comprising the biomaterial or precursor thereof may be mixed with the blood extract and delivered to the individual for use in therapy, e.g., in the treatment of a wound.

Any composition described herein may be used in an article of manufacture, the same as if each and every composition were specifically and individually listed for use in an article of manufacture. For example, it is understood that an article of manufacture may comprise a first monomer and a second monomer, wherein the first monomer comprises a thiol moiety (such as a monomer comprising a cysteine residue, for example, a peptide having at least one cysteine) and wherein the second monomer is a monomer comprising a norbornene moiety, such as a PEG monomer derivatized with norbornene.

Various Embodiments

Compositions are provided, including a composition comprising platelet rich plasma (PRP) and a biomaterial, wherein the PRP is mixed with the biomaterial. In one aspect, the biomaterial is a polymer, which may comprise (e.g., may be formable by the polymerization of) one or more monomers. For biopolymers that comprise (e.g., may be formable by the polymerization of) two or more monomers (e.g., two or three different monomers), the monomers may be mutually reactive, such as when a first monomer comprises at least one reactive moiety (e.g., a thiol moiety) and a second monomer comprises a reactive conjugated unsaturated group or at least one alkyne or alkene moiety. In one variation, the first and/or second monomer is derivatized to include a nucleophilic, reactive conjugated unsaturated, alkene or alkyne moiety. In one aspect, the first and/or second monomer is selected from the group consisting of poly(lactic acid) (PLA), polyglycolide (PGA), copolymers of PLA and PGA (PLGA), poly(vinyl alcohol) (PVA), poly(ethylene glycol) (PEG), poly(ethylene oxide), poly(ethylene oxide)-co-poly(propylene oxide) block copolymers (poloxamers, meroxapols), poloxamines, polyanhydrides, polyorthoesters, poly(hydroxy acids), polydioxanones, polycarbonates, polyaminocarbonates, poly(vinyl pyrrolidone), poly(ethyl oxazoline), carboxymethyl cellulose, hydroxyalkylated celluloses such as hydroxyethyl cellulose and methylhydroxypropyl cellulose, and natural polymers such as nucleic acids, polypeptides, polysaccharides or carbohydrates such as polysucrose, hyaluronic acid, dextran and similar derivatives thereof, heparan sulfate, chondroitin sulfate, heparin, or alginate, and proteins including without limitation gelatin, collagen, albumin, or ovalbumin, or copolymers, or blends thereof. In particularly preferred embodiments, the monomers can be selected from poly(lactic acid) (PLA), poly(vinyl alcohol) (PVA), and poly(ethylene glycol) (PEG). In another variation, the biomaterial comprises a hydrogel, such as a hydrogel comprising more than 50% solvent by weight or comprising between 50 and 95% water by weight or comprising greater than 90% water by weight. In one aspect, the one or more monomers are degradable, e.g., wherein the degradable monomer is hydrolytically, chemically or enzymatically degradable. In another variation, the first monomer comprises a peptide, e.g., wherein the peptide is enzymatically degradable. For enzymatically degradable monomers, in one aspect, the enzyme is a protease. A composition provided herein may further comprise an agent that has a biological function or activity, such as an agent that is a peptide selected from the group consisting of adhesion peptides (such as RGD adhesion sequence), growth factors, hormones, anti-hormones, signaling compounds, enzymes, serum proteins, albumins, macroglobulins, globulins, agglutinins, lectins, extracellular matrix proteins, antibodies, and antigens. Types of non-peptide agents that can be incorporated into the polymeric material include analgesics, antipyretics, non-steroidal anti-inflammatory drugs, antiallergics, antibacterial drugs, antianemia drugs, cytotoxic drugs, antihypertensive drugs, dermatological drugs, psychotherapeutic drugs, vitamins, minerals, anorexiants, dietetics, antiadiposity drugs, carbohydrate metabolism drugs, protein metabolism drugs, thyroid drugs, antithyroid drugs, and coenzymes. In compositions or methods comprising blood extract (e.g., PRP), in one variation the blood extract (e.g., PRP) comprises at least 1000 platelets or at least $1 \times 10^9$ platelets and wherein the platelets in one variation are not substantially activated or wherein less than 50% of the platelets in the PRP are activated or wherein less than 10% of the platelets in the PRP are activated.

Methods of using and making the biomaterials or precursors thereof are also provided. In one variation, a method of delivering PRP to a subject in need thereof is provided, the method comprising (a) providing PRP; (b) providing a one or more monomers; (c) mixing the PRP with the one or more monomers; (d) polymerizing the one or more monomers to form a polymer, wherein the PRP is integrated within the polymer; and (e) administering the polymer to the subject in need thereof. In one aspect, the biomaterial is a polymer, wherein the polymer comprises (e.g., may be formed by the polymerization of) one or more monomers. In one aspect, the one or more monomers comprise a first monomer and a second monomer. The first monomer in one aspect comprises at least one nucleophilic moiety such as a thiol moiety. The second monomer in one aspect comprises a reactive conjugated unsaturated group or at least one alkyne or alkene moiety. In one variation, the first and/or second monomer is derivatized to include a nucleophilic, reactive conjugated unsaturated, alkene or alkyne moiety. In another variation, the first and/or second monomer is selected from the group consisting of poly(lactic acid) (PLA), polyglycolide (PGA), copolymers of PLA and PGA (PLGA), poly(vinyl alcohol) (PVA), poly(ethylene glycol) (PEG), poly(ethylene oxide), poly(ethylene oxide)-co-poly(propylene oxide) block copolymers (poloxamers, meroxapols), poloxamines, polyanhydrides, polyorthoesters, poly(hydroxy acids), polydioxanones, polycarbonates, polyaminocarbonates, poly(vinyl pyrrolidone), poly(ethyl oxazoline), carboxymethyl cellulose, hydroxyalkylated celluloses such as hydroxyethyl cellulose and methylhydroxypropyl cellulose, and natural polymers such as nucleic acids, polypeptides, polysaccharides or carbohydrates such as polysucrose, hyaluronic acid, dextran and similar derivatives thereof, heparan sulfate, chondroitin sulfate, heparin, or alginate, and proteins including without limitation gelatin, collagen, albumin, or ovalbumin, or copolymers, or blends thereof. In particularly preferred embodiments, the monomers can be selected from poly(lactic acid) (PLA), poly(vinyl alcohol) (PVA), and poly(ethylene glycol) (PEG). In one aspect, the polymer comprises a hydrogel, such as a hydrogel comprising more than 50% solvent by weight or between 50 and 95% water by weight or comprising greater than about 90% or about 95% water by weight (such as a hydrogel comprising about 96% or about 98% water by weight). In one aspect, the first or second monomers are degradable, wherein the degradable monomer is hydrolytically, chemically or enzymatically degradable. In one aspect, the first monomer comprises a peptide, which may be enzymatically degradable, e.g., by a protease. In one aspect, the method further comprises the addition of a photoinitiator which may be selected from the group consisting of Irgacure 2959, Irgacure 184, Irgacure 651, LiAP and NaAP. The method may further comprise exposing the first and second monomers to light, such as light elected from infrared, ultraviolet and visible light. In one aspect, the light has a wavelength between 350 and 450 nm. In another aspect, the light exposure lasts for less than one, two, five or 20 minutes.

Also provided is a method of treating skin wounds, orthopedic conditions, pain, nerve injury, tendinitis, osteoarthritis, cardiac muscle injury, bone injury, traumatic injury or dental injury comprising administering to a subject in need thereof a composition comprising platelet rich plasma (PRP) and a biomaterial, wherein the PRP is mixed with the biomaterial. Also provided is a method of treating skin wounds, orthopedic conditions, pain, nerve injury, tendinitis, osteoarthritis, cardiac muscle injury, bone injury, traumatic injury or dental injury comprising (a) administering to a subject in need thereof a one or more monomers mixed with PRP; and (b) polymerizing the polymer; thereby treating the subject in need thereof. The step (b) may further comprise the addition of a photoinitiator, such as a photoinitiator selected from the group consisting of Irgacure 2959, Irgacure 184, Irgacure 651, LiAP and NaAP. The step (b) may further comprise exposing the first and second monomers to light, which light may be selected from infrared, ultraviolet and visible light. In one aspect, the light has a wavelength between 300 and 400 nm. In one aspect, the light exposure lasts for less than one, two, five or 20 minutes.

Also provided is a method of slowing the activation of PRP administered to a subject in need thereof comprising administering to a subject in need thereof a composition comprising platelet rich plasma (PRP) and a biomaterial, wherein the PRP is mixed with the biomaterial.

A kit is also provided, wherein the kit comprises platelet rich plasma (PRP) and a biomaterial, wherein the PRP is mixed with the biomaterial. A kit may further comprise a photoinitiator.

EXAMPLES

Blood Fraction/Extracts in Combination with Biomaterials

Example 1. Application of ADP-Activated PRP Releaseate with Biomaterial to Full Thickness Skin Wounds Biomaterial Preparation.

A monomer solution was prepared in water containing 5% wt/vol 20 kD 4-arm poly(ethylene glycol)-norbornene (20K4A PEG-NB), 5% wt/vol 6 kD linear poly(ethylene glycol)-norbornene (6Klinear PEG-NB), 6.7 mM di-cysteine enzymatically degradable crosslinker peptide (KCGPQ-GIAGQCK (SEQ ID NO: 46)), and 6.7 mM di-cysteine enzymatically degradable crosslinker peptide (CALKV-LKGC (SEQ ID NO: 47)). In this system, cysteine-containing peptides and PEG-NB monomers are mixed in a 1:1 stoichiometric ratio with respect to "thiol" and "ene" functional groups. In the presence of the LiAP photoinitiator, and upon exposure 385 nm light, the thiol group adds to the norbornene, forming a norbornene-thioether linkage.

ADP-Activated PRP Releaseate Preparation and Storage.

Fresh whole blood was collected from pigs at the time of slaughter into two 50 ml tubes containing 8 ml of Anticoagulant Citrate Dextrose (ACD) each to prevent platelet activation and coagulation. Red Blood Cells (RBCs) were then removed by centrifuging the tubes at 3500 rpm in a Sequire clinical centrifuge for 10 minutes. Supernatants (approximately 25 ml) with some RBCs remaining were pooled into 2 conical tubes and centrifuged again at 3500 rpm for 10 minutes. Clear supernatants (plasma) were then transferred to new 50 ml conical, and Buffy Coat (BC) with some RBCs put into 15 ml conicals. Further RBC removal was achieved by spinning BC at 3500 rpm for 5 minutes and then carefully transferring the BC back into the clear supernatant separated in the previous step. The 50 ml of BC+plasma was spun at 3900 rpm for 8 minutes, and the clear supernatant was removed from top until 5 ml total volume (pellet+plasma) remained. Using the plasma remaining in the tube, the platelet pellet was resuspended by pipetting up and down. This 5 ml volume of BC in plasma was, effectively, PRP. The PRP was aliquotted into 1 ml volumes to which 20 ul of 2.5 mM ADP (Adenosine-5'-diphosphate) and 5 ul of 2M $CaCl_2$ were added to activate the platelets. Each sample was mixed by inversion, allowed to incubate at room temperature for 15 minutes, and then centrifuged for 10 minutes at 14,000 rpm in a tabletop microcentrifuge. The clear supernatant, ADP-activated PRP releaseate, was transferred to fresh tubes and stored at −80° C. until use.

Releaseate/Biomaterial Mixture.

After thawing, 1.5 ml of the ADP-activated PRP releaseate was transferred into a 15 ml conical tube containing the following pre-mixed components: 8.25 ml water, 0.75 ml 10×PBS, 3.0 ml of the 10% wt/vol monomer solution prepared as described above, and 1.5 ml of LiAP at 2% wt/vol. The sample was mixed by inversion, creating a releaseate/biomaterial mixture with the following final concentrations: 20% vol/vol ADP-activated PRP releaseate, 1% wt/vol 20K4A PEG-NB, 1% wt/vol, 1.34 mM di-cysteine enzymatically degradable crosslinker peptide (KCGPQ-GIAGQCK (SEQ ID NO: 46)), 1.34 mM di-cysteine enzymatically degradable crosslinker peptide (CALKVLKGC (SEQ ID NO: 47)), and 0.2% wt/vol LiAP.

Application.

The serum/biomaterial mixture was then applied as a liquid to a full-thickness skin wound that had been created on the back of a Yorkshire pig with a 1 cm biopsy punch. Polymerization of the hydrogels was accomplished by shining a handheld LED light emitting 385 nm light (0.4 $mW/cm^2$) over the solution for 30 seconds. The wound was then covered with Tegaderm and allowed to heal for one week.

Assessment.

After one week, biopsies were taken from each wound and processed for histological evaluation. Tissue sections were read by a certified pathologist using the following criteria: (1) A Percent of wound epithelialized (%): Measurement of the length of the wound surface that had been covered with epithelium; (2) Epithelial thickness (cell layers μm): The thickness of the epithelium in μm was measured on five equal distance points from each other in the biopsy and averaged; (3) White cell infiltrate: Measured by the presence and amount of subepithelial mixed leukocytic infiltrates (Mean Score: 1=absent, 2=mild, 3=moderate, 4=marked, 5=exuberant); (4) Granulation Tissue Formation: The approximate amount of new granulation tissue formation was graded (0=0, 0.5=1-10%, 1=11-30%, 2=31-50%, 3=51-70%, 4=71-90%, 5=91-100%); (5) New Blood Vessel Formation: Presence of new blood vessels (Mean Score: 1=absent, 2=mild, 3=moderate, 4=marked, 5=exuberant). The results of this study are summarized in the following table.

TABLE E1

Histological evaluation of full-thickness wounds treated with releaseate/biomaterial compared to untreated control wounds.

| Healing Measurement | PRP Releasate + Biomaterial | Untreated Control |
| --- | --- | --- |
| Epithelialization (%) | 89.7 | 40.9 |
| Elpithelial thickness (um) | 154.44 | 139.2 |
| White cell infiltration | 3.8 | 4.2 |

TABLE E1-continued

Histological evaluation of full-thickness wounds treated with releasate/biomaterial compared to untreated control wounds.

| Healing Measurement | PRP Releasate + Biomaterial | Untreated Control |
|---|---|---|
| Granulation Tissue | 5 | 3.2 |
| Angiogenesis | 4 | 3.3 |

As shown in Table E1, treatment of full-thickness skin wounds with a PRP releasate+biomaterial increased the rate of re-epithelialization, the epithelial thickness, the accumulation of granulation tissue, and the presence of new blood vessels. In addition, white cell infiltration was reduced, suggesting that inflammation was lowered with the blood extract/biomaterial treatment. In addition, no evidence of residual biomaterial remained either on the surface of the wound (observed at time of biopsy) or embedded within the wound (observed in tissue sections), indicating that the biomaterial had been degraded and cleared by the animal's body.

Example 2. Plasma Provides Substrate for Cellular Migration when Combined with Biomaterials An important aspect of tissue repair and regeneration is the infiltration of cells from the body into the injury or defect site. Therefore, biomaterials and/or extract-biomaterial combinations must support cellular migration, a process that requires cells to interact with the insoluble extracellular matrix (ECM). Traditionally, tissue engineers have used simple ECM mimics (e.g. RGD) to provide cellular adhesion motifs to their biomaterials, allowing cells to both hold on to the matrix as well as generate forces that result in migration. In order to evaluate the ability of plasma and serum to support migratory responses of cells into synthetic biomaterial lacking cell adhesion moieties, a collagen plug assay was utilized:

Preparation of Whole Blood Fractions.

Two distinct whole blood samples were collected using the BD Vacutainer system (Franklin Lakes, N.J., USA). Briefly, venipuncture was performed with a BD Vacutainer Safety-Lok Blood Collection Set with Pre-Attached Holder (REF 368652). Blood was then collected directly into specific vacutainers without removal of the needle: (1) for serum, a red-capped BD Vacutainer with clot activators (REF 367820) was used, and (2) for plasma, a yellow-capped BD Vacutainer with Anticoagulant Citrate Dextrose (ACD) (REF 364606) was used. After filling with blood, each Vacutainer was disconnected from the Blood Collection Set and inverted 4 times. Blood samples were then allowed to sit at room temperature for 30 minutes, during which time only the blood in tubes (1) clotted. Each tube was then centrifuged at 3500 rpm for 5 minutes. After centrifugation, the yellow supernatant was transferred to a new tube without disturbing the red blood cells layer on the bottom. These yellow supernatants (serum and plasma) were then used in combination with biomaterials.

Biomaterial Preparation.

A monomer solution was prepared in water containing 5% wt/vol 20 kD 4-arm poly(ethylene glycol)-norbornene (20K4A PEG-NB), 5% wt/vol 6 kD linear poly(ethylene glycol)-norbornene (6Klinear PEG-NB), and 13.4 mM di-cysteine enzymatically degradable crosslinker peptide (KCGPQGIAGQCK (SEQ ID NO: 46)). In this system, cysteine-containing peptides and PEG-NB monomers are mixed in a 1:1 stoichiometric ratio with respect to "thiol" and "ene" functional groups. In the presence of the LiAP photoinitiator, and upon exposure 385 nm light, the thiol group adds to the norbornene, forming a norbornene-thio-ether linkage.

Blood Fraction/Biomaterial Mixture.

450 ul of the serum or plasma was transferred into a new tube containing the following pre-mixed components: 600 ul water, 75 ul 10×PBS, 300 ul of the 10% wt/vol monomer solution prepared as described above, and 75 ul of LiAP at 2% wt/vol. The sample was mixed by inversion, creating a blood fraction/biomaterial mixture with the following final concentrations: 30% vol/vol serum or plasma, 1% wt/vol 20K4A PEG-NB, 1% wt/vol, 2.7 mM di-cysteine enzymatically degradable crosslinker peptide (KCGPQGIAGQCK (SEQ ID NO: 46)), and 0.1% wt/vol LiAP.

Cellular Outgrowth Assay.

Human dermal fibroblasts (HDFs) were seeded in a Type I Collagen plug and cultured in vitro for 3 days to allow the cell-seeded plugs to contract. Each plug was then removed from media, dabbed to remove excess liquid, and then submerged into 0.4 ml of the blood fraction/biomaterial mixture that had been had been added to the well of a new 24-well tissue culture plate. Each sample was then polymerized by shining a handheld LED light emitting 385 nm light (0.4 mW/cm$^2$) over the well for 30 seconds. After polymerization of the biomaterial, 1 ml of media was added to the top of each sample, and the plate was placed in a tissue culture incubator (37° C., 5% $CO_2$) for 24 hours. Cellular outgrowth is then scored where 0=no outgrowth and 5=robust outgrowth surrounding out of the collagen plug. This assay is a useful tool for evaluating (1) the biological activity of blood extract and (2) the ability of a biomaterial to scaffold cellular migration.

TABLE E2

Outgrowth scores of biomaterial constructs containing either plasma or serum.

|  | Outgrowth score (24 hrs) | Outgrowth score (72 hrs) |
|---|---|---|
| plasma | 2 | 3 |
| serum | 0 | 0 |

Figure 8:
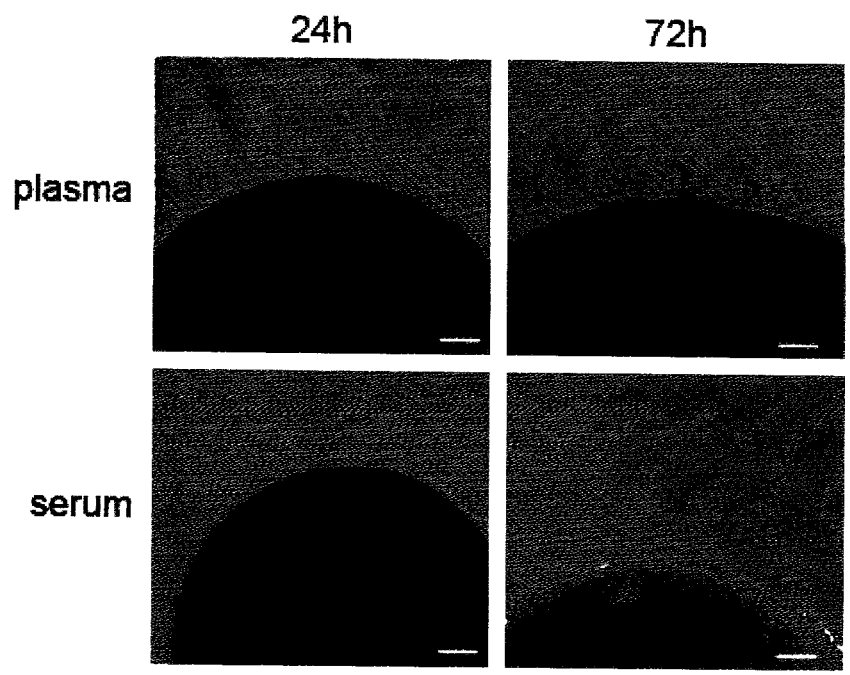
FIG. 8 illustrates the results of a cellular outgrowth assay in which a collagen plug seeded with human dermal fibroblasts was embedded into biomaterials containing either plasma or serum to support cellular migration. Cellular migration was micrographed at 24 and 72 hours.

As the data in Table E2 demonstrate, constructs containing plasma supported cellular outgrowth; whereas, constructs containing serum lacked an ability to support cellular infiltration. The results of this experiment is further shown in FIG. 8, where it is clear that the addition of plasma, not serum, to the hydrogel formulation supported fibroblast outgrowth, suggesting that critical cell adhesion factors (likely fibrin/fibrinogen) are present in plasma but depleted from serum. This is likely due to the fact that serum drawn after clotting events is depleted of plasma proteins that can act as substrates for cellular adhesion and migration. This example does not attempt to identify or demonstrate all of the potential bioactivity of plasma.

Example 3. Whole Blood Fractions Support Activated Cellular Outgrowth into Biomaterials An important aspect of tissue repair and regeneration is the infiltration of cells from the body into the injury or defect site. The initial responders act to degrade damaged tissue and fight infectious agents. The second wave of cells begins the rebuilding process, secreting factors that re-establish the extracellular matrix that re-creates tissues. Because these events are generally mediated by cells that arrive at the injury site and migrate into the wound, factors that stimulate and/or support these migratory and/or proliferative processes are of critical importance to tissue repair and regeneration. The following experiment was performed to evaluate the ability of whole blood fractions to enhance cellular migration by using a common outgrowth assay. It should be noted that these outgrowth assays were performed in serum-free media, preventing the stimulation of cells by chemoattractants present in standard culture media.

Preparation of Whole Blood Fractions.

Four distinct whole blood samples were collected using the BD Vacutainer system (Franklin Lakes, N.J., USA). Briefly, venipuncture was performed with a BD Vacutainer Safety-Lok Blood Collection Set with Pre-Attached Holder (REF 368652). Blood was then collected directly into specific vacutainers without removal of the needle: (1) red-capped BD Vacutainer with clot activators (REF 367820), (2) yellow-capped BD Vacutainer with Anticoagulant Citrate Dextrose (ACD) (REF 364606), (3) red-capped BD Vacutainer (no added clot activators, REF 366441) to which 1 ml of 40 mM EGTA had been added with a syringe and needle before blood draw, and (4) green-capped BD Vacutainer with Sodium Heparin (REF 367871). After filling with blood, each Vacutainer was disconnected from the Blood Collection Set and inverted 4 times. All blood samples were then allowed to sit at room temperature for 30 minutes, during which time only the blood in tubes (1) clotted. Samples of each tube type were then split into two groups: "normal spin" and "slow spin." "Normal spin" tubes were centrifuged at 3500 rpm for 5 minutes and "slow spin" tubes were centrifuged at 1000 rpm for 5 minutes. After centrifugation, the yellow supernatant was transferred to a new tube without disturbing the red blood cells layer on the bottom. These yellow supernatants were then used in combination with biomaterials.

Biomaterial Preparation.

A monomer solution was prepared as described in Example 2.

Blood Fraction/Biomaterial Mixture.

For each of the samples described above, 250 ul of the RBC-depleted whole blood fraction was transferred into a new tube containing the following pre-mixed components: 562 ul water, 056 ul 10×PBS, 225 ul of the 10% wt/vol monomer solution prepared as described above, and 75 ul of LiAP at 2% wt/vol. The sample was mixed by inversion, creating a blood fraction/biomaterial mixture with the following final concentrations: 21% vol/vol RBC-depleted whole blood, 1% wt/vol 20K4A PEG-NB, 1% wt/vol, 2.7 mM di-cysteine enzymatically degradable crosslinker peptide (KCGPQGIAGQCK (SEQ ID NO: 46)), and 0.13% wt/vol LiAP.

Cellular Outgrowth Assay.

Cellular Outgrowth Assays were performed as described in Example 2.

TABLE E3

Cellular outgrowth scores of blood fractions with biomaterials.

|  | centrifugation | Outgrowth score |
|---|---|---|
| serum | fast | 0 |
| ACD | fast | 2 |
| ACD | slow | 3.5 |
| EGTA | fast | 1 |
| EGTA | slow | 3.5 |
| heparin | fast | 0 |
| heparin | slow | 0 |

As shown in Table E3, the addition of whole blood fractions to a biomaterial increased cellular outgrowth of human dermal fibroblasts from collagen plugs. As observed in Example 2, the addition of serum to the biomaterial did not support cellular outgrowth, likely due to a lack of cellular adhesion proteins that are precipitated during clotting. No coagulation occurred in each of the remaining samples due to the presence of ACD, EGTA, or heparin. Therefore, it would be expected that these samples retained the proteins that provided sites for cell adhesion and migration (likely fibrin/fibrinogen), and thus supported cellular outgrowth. Unexpectedly, samples anticoagulated with heparin did not show measureable signs of cellular outgrowth, suggesting that heparin causes these proteins to migrate with the Red Blood Cell layer or that heparin interferes in some way with cell adhesion.

The outgrowth data obtained from "fast" and "slow" samples collected from the blood into tubes containing ACD and EGTA provide valuable insight into the biological activities of these fractions. These samples clearly demonstrate that (1) biological activity of blood fractions remains after mixing with the biomaterial and that (2) the biomaterial can provide a scaffold through which cells can migrate. Of significant importance, the "slow" samples for both ACD and EGTA performed better in this assay than the respective "fast" samples, suggesting that the "slow" samples had greater biological activity. One explanation for this observation is that the "fast" centrifugation causes the sedimentation of proteins that provide the site of cell adhesion and migration. It is also possible that "fast" centrifugation causes the sedimentation of growth factors that are involved in activating cellular migration.

The most likely explanation for the difference that is observed between the outgrowth into the biomaterials containing the "fast" and the "slow" fractions is the presence/depletion of platelets. Centrifugation at 3500 rpm causes whole blood samples to sediment into three distinct cell layers: plasma (no cells), buffy coat (platelets and white blood cells), and red blood cells (RBCs). As a result, platelets are depleted in the top fraction. While this does not cause a loss of soluble proteins that provide the cell attachment sites once incorporated into the biomaterial, it would cause a loss of platelets, which store growth factors that are known to activate cellular migration. Whole blood samples that are centrifuged at "slow" speeds do not separate into three distinct layers. Instead, two layers are formed: a cloudy yellow layer (plasma+platelets+white blood cells) and a dark red layer (RBCs). As such, the biomaterials loaded with these "slow" fractions contain unactivated platelets.

These results also represent two important aspects as outlined below.

First, it is not required to concentrate the platelets in order to obtain significant biological activity from blood. PRP technologies are all based on the belief that platelet concentration is an essential step in the process of harvesting the physiologically relevant levels biological activity of platelets and platelet releasates. Generally, it is thought that a concentration of PRP to 4-6 times that of whole blood is optimal for biological activity. These data clearly indicate that the complicated and time-consuming steps to concentrate platelets is not required for obtaining a fraction of blood with significant biological activity and that the simple combination of a plasma and/or serum with an appropriate biomaterial can be an effective way to harvest the biological activity of platelets.

Second, the activation of platelet in advance of mixing with a biomaterial and application to a patient is not required. If the biomaterial is able to deliver unactivated platelets (either in the form of a "slow" whole blood fractionation, whole blood, PRP, platelets purified from blood—washed or unwashed, etc.), the opportunity exist to further control, in a more biologically relevant manner, the release of factors that stimulate wound healing. That is, unactivated platelets, delivered to a site with an appropriate biomaterial would stay unactivated until natural tissue repair/regeneration processes take place, at which time they would release growth factors in a highly localized manner and in a physiologically appropriate manner (when cells migrate into the biomaterial and cause local changes to the environment that activate the platelets—deposition of collagen, etc.). In this way, the control the timing of platelet activation and degranulation would be dictated be the wound, an effect that would serve to store critical wound healing factors until an appropriate time. Activation of the platelets at the time of mixing with the biomaterial or upon application to a wound site (polymerization, perhaps) would also provide significant benefit. This would ensure that the critical biological activity of platelets would not be lost during step in advance of application. In addition, this would be a method to ensure that both the growth factor content of platelets as well as the scaffolding proteins of plasma (fibrin/fibrinogen, for example) are both delivered with the biomaterial.

Example 4. Carrier-Enhanced Delivery of PRP for Wound Healing

Acute full-thickness wound healing in pig model: A 2× monomer solution was prepared in PBS (12% wt/vol 20K 4-arm poly(ethylene glycol)-norbornene (PEG-NB), 2 mM adhesion peptide (CRGDS, SEQ ID NO: 48), 11 mM di-cysteine MMP-degradable crosslinker peptide (KCGPQ-GIAGQCK (SEQ ID NO: 46)), and 0.02% LAP photoinitiator). 44 ml of whole blood was drawn from an anesthetized 90 kg Yorkshire pig and used to prepare PRP as described in Example 1. The PRP fraction was then mixed with an equal volume of monomer solution. The resulting mixture was then applied to clean, full-thickness wounds that had been created in the back of the pig with a 1 cm biopsy punch. Polymerization of the hydrogels was accomplished by shining a handheld LED flashlight emitting 385 nm light over the PRP/PEG solution for 2 minutes. Layering of the material was performed to ensure polymerization of the hydrogel throughout the wound volume. The wounds were then covered with Tegaderm® and allowed to heal for one week, at which time the animal was sacrificed to harvest tissue from the wound sites. Histological analysis of the wound tissue revealed significant cellular infiltration into the PEG matrices containing blood fractions, demonstrating that signaling molecules from the PRP remained active and that active wound healing was enhanced in these constructs. Wounds treated with PRP alone (activated with thrombin and calcium) show reduced cellular activity at the site with limited evidence of cellular migration into the wound volume.

Preparation of Blood Fractions/Extracts

Example 5. Isolation of Blood Fractions (Red Blood Cells (RBCs), PRP and Plasma)

Blood fractions we isolated using a Secquire® Cell Separator (PPAI Medical, Fort Meyers, Fla.) as per the manufacturer's instructions. Briefly, a 60 ml syringe was filled with 6 ml of the anticoagulant citrate phosphate dextrose solution (CPD). 44 ml of blood was then drawn into the syringe and mixed with the CPD solution. Mixture was then added to the Secquire® unit via the "BLOOD" Port. The Secquire® unit was centrifuged at 3500 RPMs for 9 minutes. Using the "BLOOD" Port, The Red Blood Cell (RBC) was withdrawn with a separate 60 ml syringe. The Secquire unit was centrifuged again at 3500 RPMs for 3-5 minutes. Using the "PLASMA" Port, plasma was then withdrawn with a separate 60 ml syringe. The remaining contents in the Secquire® unit, PRP, were reconstituted by gently swirling the tube and then withdrawn through the "BLOOD" port.

Example 6. Isolation of PRP Extract

A bag of expired human platelets was purchased from a blood bank and maintained at 37° C. until used for extract preparation. Under sterile conditions, the platelets were transferred to 50 ml conical tubes and centrifuged at 3300 RPM for 30 minutes. After discarding the supernatant, the platelet pellet was resuspended with 15 ml deionized water. Each tube was vortexed for 15 seconds and then placed in a sonicator bath for 90 seconds. Each tube was then centrifuged for 1 hour at 4200 RPM to pellet insoluble cell debris. Without disrupting the pelleted material, the supernatant (containing soluble platelet growth factors and cytokines) was removed and stored at 4° C. until use.

Example 7. Isolation of Blood Fraction

Plasma

Whole blood was collected using a BD Vacutainer system (Franklin Lakes, N.J., USA). Briefly, venipuncture was performed with a BD Vacutainer Safety-Lok Blood Collection Set with Pre-Attached Holder (REF 368652). Blood was then collected directly into a yellow-capped BD Vacutainer with Anticoagulant Citrate Dextrose (ACD) (REF 364606) as per the manufacturer's instructions. After filling with blood, the Vacutainer was disconnected from the Blood Collection Set and inverted 4 times to mix the blood with the ACD solution. The tube was then centrifuged at 3500 RPMs for 5 minutes using a Sequire clinical centrifuge to pellet cells and insoluble factors. The yellowish, clear plasma was transferred from the top of the Vacutainer with a syringe and needle.

Example 8. Isolation of Blood Fraction

Serum

Whole blood was collected using a BD Vacutainer system (Franklin Lakes, N.J., USA). Briefly, venipuncture was performed with a BD Vacutainer Safety-Lok Blood Collection Set with Pre-Attached Holder (REF 368652). Blood was then collected directly into a red-capped BD Vacutainer with clot activators (REF 367820) as per the manufacturer's instructions. After filling with blood, the Vacutainer was disconnected from the Blood Collection Set and inverted 5 times. The tube was allowed to sit at room temperature for 30 minutes while clotting occurred. The sample was then centrifuged at 3500 RPMs for 5 minutes using a Sequire clinical centrifuge to pellet the clotted blood. The yellowish, clear serum was transferred from the top of the Vacutainer with a syringe and needle.

Example 9. Prophetic Isolation of Blood Fraction

Selectively Activated Platelet Releasate Serum (SAPRS)

Whole blood is collected using a BD Vacutainer system (Franklin Lakes, N.J., USA). Briefly, venipuncture was performed with a BD Vacutainer Safety-Lok Blood Collection Set with Pre-Attached Holder (REF 368652). Blood was then collected directly into a red-capped BD Vacutainer (no added clot activators, REF 366441) in which 10 ul of 2M $CaCl_2$ and 40 ul of 2.5 mM ADP is injected before the blood draw. After filling with blood, the Vacutainer is disconnected from the Blood Collection Set and inverted 5 times. The tube is allowed to sit at room temperature for 30 minutes while platelet activation occurred. The sample is then centrifuged at 3500 RPMs for 5 minutes to pellet the cells and clotted factors. The yellowish, clear SAPRS can then be transferred from the top of the Vacutainer with a syringe and needle.

Example 10. PDGF Release in Samples of Anticoagulated Whole Blood

Whole blood was collected from a healthy volunteer by a certified phlebotomist into a 8.5 mL ACD-containing Vacutainer. 375 ul of 0.167 mM PAR1-AP in ultrapure water or 200 ul of 0.1 unit/microliter of thrombin (Zymogenetics) were injected into the vacutainers via a sterile 1 mL syringe; samples were gently mixed by inverting 10 times and incubated at ambient temperature for specified time. The samples were then centrifugated at 2,380×g for 5 minutes at ambient temperatures and ~3 mL clear supernatants were collected from the top of each sample and transferred into sterile 15 mL conical tubes. Concentration of PDGF-BB in each sample was determined by ELISA (Quantikine kit, R&D Systems) according to the manufacturer's protocol.

Figure 9:
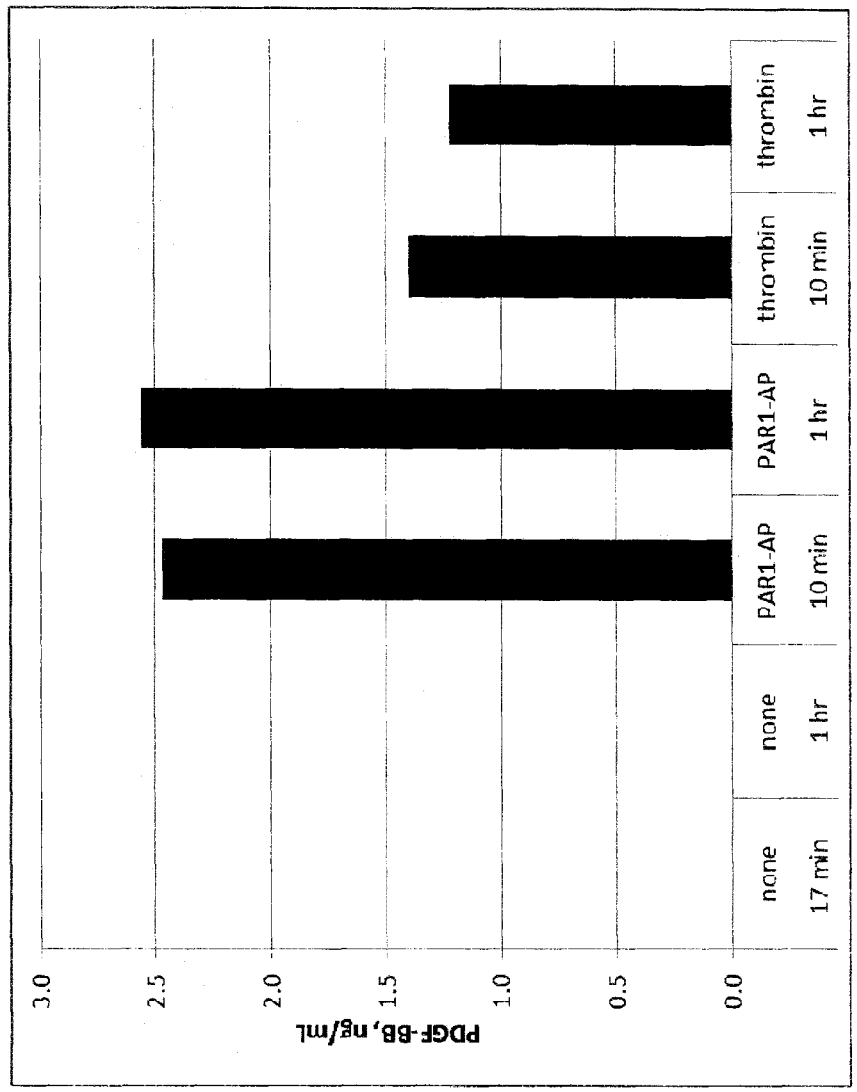
FIG. 9 shows that activation of whole blood increases PDGF-BB levels. PDGF-BB was measured by ELISA in whole blood anticoagulated with ACD and then treated with PAR1-activating peptide or Thrombin for 10 minutes or for 1 hour. An untreated sample was used as a control.

As shown in FIG. 9, measurement of PDGF-BB levels in each of these samples reveals that the treatment of uncoagulated whole blood with different activators results in different levels of growth factor release. Thrombin-treated samples showed some signs of coagulation after 60 minutes; whereas the untreated (ACD) and ADP-treated (ADP) samples did not. These data indicate that (1) growth factor release from platelets can be selectively induced, (2) the activation of coagulation pathways is not required for growth factor release, and (3) significant increases in growth factor concentrations can be induced in whole blood.

Example 11. Selectively Activated PRP and Washed Platelet Releasates

Fresh whole blood (WB) was collected into tubes containing appropriate levels of Anti-coagulant Citrate Dextrose (ACD) to prevent platelet activation and coagulation. WB samples were then split into 4 conical tubes, 50 ml WB+ACD per tube. Red Blood Cells (RBCs) were then removed by centrifuging the tubes at 3500 rpm for 10 minutes in a clinical centrifuge. Supernatants (approximately 25 ml) with some RBCs remaining were pooled into 2 conical tubes and centrifuged again at 3500 rpm for 10 minutes. Clear supernatants (plasma) were then transferred to new 50 ml conical, and Buffy Coat (BC) with some RBCs put into 15 ml conicals. Further RBC removal was achieved by spinning BC at 3500 rpm for 5 minutes and then carefully transferring the BC back into the clear supernatant separated in the previous step; 2 equal samples of approximately 50 ml remained: (1) One was processed for PRP and (2) One was processed for Washed Platelets (WP)

1. PRP preparation: 50 ml of BC+plasma was spun at 3900 rpm for 8 minutes; the clear supernatant was removed from top until 5 ml total volume (pellet+plasma) remained; the platelet pellet was resuspended in plasma by pipetting up and down. This 5 ml volume of BC resuspended in plasma was, effectively, PRP.

2. WP preparation: 50 ml of BC+plasma was spun at 3900 rpm for 8 minutes; the clear supernatant was completely removed from the sample, leaving the pellet intact; the platelet pellet was resuspended in 5 ml Wash Buffer (130 mM NaCl, 2.68 mM KCl, 11.9 mM $NaHCO_3$, 5 mM $NaH_2PO_4$, 5.56 mM glucose, 1 mM $MgCl_2$, 10 mM sodium citrate) by pipetting up and down. The sample was spun at 3900 rpm for 5 minutes, and the supernatant was removed. The platelet pellet was resuspended in 5 ml Wash Buffer, effectively creating WP.

PRP and WPs were aliquotted into 1 ml volumes, and 4 tubes of PRP and 4 tubes of WPs were used for preparation of activated releasates: (1) no selective activation, in which no platelet activator was added (2) PAR1 activation, in which 20 ul of 500 uM PAR1 Activating Peptide (PAR1 AP) (SFLLRN, SEQ ID: 40) was added, (3) PAR4 activation, in which 20 ul of 500 uM PAR4 Activating Peptide (PAR4 AP) (AYPGKF, SEQ ID: 44) was added, and (4) ADP activation, to which 20 ul of 2.5 mM ADP (Adenosine-5'-diphosphate) was added. To each sample, 5 ul of 2M $CaCl_2$ was added to counter ACD inhibition of platelet activation. Each sample was mixed by inversion and allowed to incubate at room temperature for 15 minutes. Selectively Activated PRP and WP Releasates were obtained by centrifuging each sample for 10 minutes at 14,000 rpm in a tabletop microcentrifuge and then removing the clear supernatant from the sample. PDGF-BB levels were then measured by ELISA using a Human PDGF-BB Quantikine ELISA Kit (R&D Systems).

Figure 10:
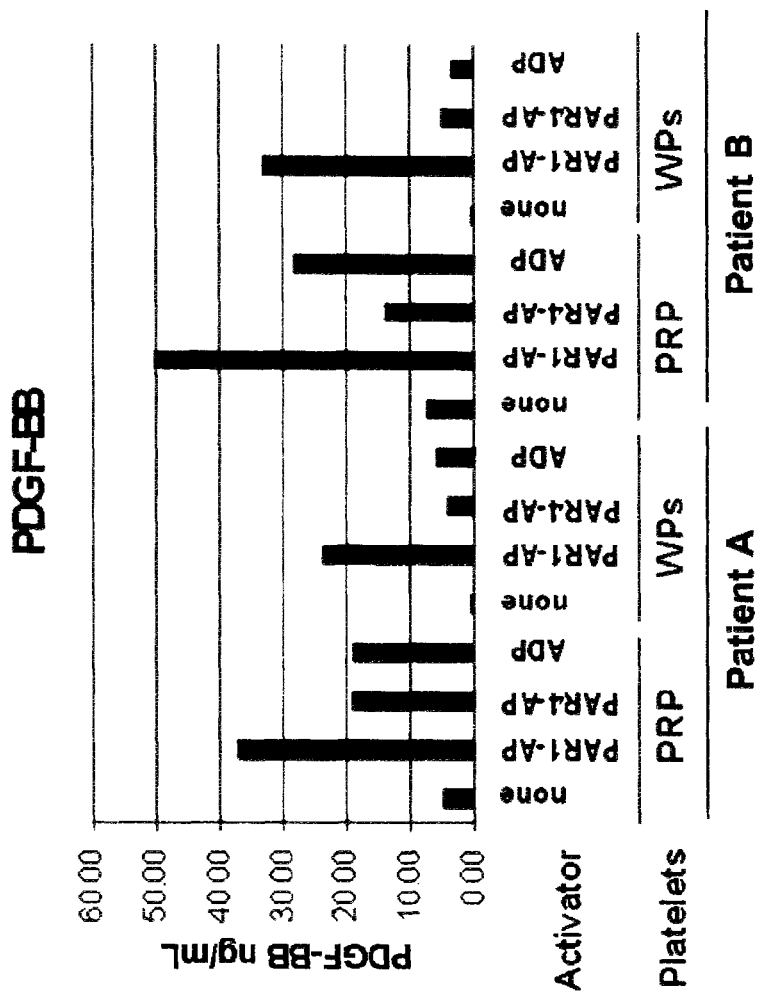
FIG. 10 illustrates that activation of platelets with different activators results in different levels of growth factor release. PDGF-BB levels were measured by ELISA in samples of washed platelets (WP) and PRP that were activated with a PAR1-activating peptide, a PAR4-activating peptide, ADP, or no activation. Data is shown for two individuals, patient A and patient B.

As shown in FIG. 10, measurement of PDGF-BB levels in each of these samples reveals that the treatment of platelets with different activators results in different levels of growth factor release. While some variability does exist between patients (Patients A and B), PAR1-AP consistently induced the greatest release of PDGF-BB in both PRP and WP preparations. PRP samples also had consistently higher levels of PDGF-BB when compared to WP samples prepared from the same platelet source.

Biomaterials

Example 12. Preparation of Non-Degradable Hydrogels

Monomer solutions were prepared in PBS containing 10% wt/vol 4600MW poly(ethylene glycol)-diacrylate (PEGDA) and 0.05% photoinitiator Irgacure-2959 (12959). To create a hydrogel, 70 µl of the monomer solution was placed into a mold made by cutting an 8 mm diameter hole in a 2 mm thick gasket that had been placed on a clean glass slide. Polymerization of the hydrogel was accomplished by shining a 100 WHg short-arc lamp (Omnicure® 1000, EXFO, Mississaugua, Ont., Canada) with the manufacturer-supplied filter for 365 nm exposure on the sample for 10 minutes.

In this system, the presence of ester bonds within each PEGDA monomer makes the resulting polymer susceptible to hydrolytic degradation. However, the rate of degradation would be generally considered too slow for tissue engineering applications. Thus, for the sake of this disclosure, PEGDA hydrogels are considered non-degradable.

Example 13. Preparation of Hydrolytically Degradable Hydrogels

Monomer solutions were prepared in PBS containing 6% wt/vol methacrylated hyaluronic acid (MeHA) and methacrylated caprolactone HA (MeCLHA) at a 1:1 ratio and 0.05% photoinitiator Irgacure-2959 (I2959). MeHA and MeCLHA monomers were synthesized as previously described (Chung, Biomaterials. 2009 September; 30(26): 4287-4296). To create a hydrogel, 70 µl of the monomer solution was placed into a mold made by cutting an 8 mm diameter hole in a 2 mm thick gasket that had been placed on a clean glass slide. Polymerization of the hydrogel was accomplished by shining a 100 WHg short-arc lamp (Omnicure® 1000, EXFO, Mississaugua, Ont., Canada) with the manufacturer-supplied filter for 365 nm exposure on the sample for 10 minutes.

In this system, the presence of caprolactone linkages makes the polymer system susceptible to hydrolytic degradation at a rate that is compatible with medical applications of this sort.

Example 14. Preparation of Enzymatically Degradable Hydrogels

Monomer solutions were prepared in PBS containing 6% wt/vol 20K 4-arm poly(ethylene glycol)-norbornene (PEG-NB), 6 mM di-cysteine enzymatically degradable crosslinker peptide (KCGPQGIAGQCK (SEQ ID NO: 46)), and 0.01% photoinitiator lithium phenyl-2,4,6-trimethylbenzoylphosphinate (LAP or LiAP). In this system, cysteine-containing peptides and 4-arm PEG-NB monomers are mixed in a 1:1 stoichiometric ratio with respect to "thiol" and "ene" functional groups. In the presence of the LAP photoinitiator, and upon exposure 385 nm light, the thiol group adds to the norbornene, forming a norbornene-thioether linkage. To create a hydrogel, 70 µl of the monomer solution was placed into a mold made by cutting 8 mm diameter holes in a 2 mm thick gasket that had been placed on a clean glass slide. Polymerization of the hydrogels was accomplished by shining a handheld LED flashlight emitting 385 nm light over the solution for 1 minute.

In this system, crosslinking peptides require the presences of at least two cysteines (R-groups contain "thiol" moieties), allowing them to covalently react with more than one multi-armed "ene"-functionalized PEG. A 4-arm PEG-NB was reacted with a dicysteine peptide crosslinker that was designed to be susceptible to enzymatic degradation by naturally occurring extracellular matrix remodeling enzymes. Specifically, a collagen-based sequence, KCGPQG*IAGQCK (SEQ ID NO: 46), was used for its known susceptibility to cleavage by matrix metalloproteinases (MMPs), where the "*" denotes the site of enzymatic cleavage. With this crosslinker, the hydrogel can be degraded by the body.

Example 15. Preparation of Hydrogels with Moieties for Cell Adhesion

To provide a substrate for cellular attachment to the hydrogels described in Example 14, short bioactive adhesion peptides can be easily incorporated into the scaffold by the inclusion of a thiol-containing cysteine residue. A fibronectin-mimic, RGDS, was functionalized by adding a cysteine amino acid to the amino-terminal end of the peptide: CRGDS (SEQ ID NO: 48). When included in the prepolymerized monomer solution, this peptide reacts with the PEG-NB backbone via the same thiol-ene chemistry that links the cysteines of the MMP-degradable peptide to the norbornene of the PEG-NB arms, resulting in a pendant cell attachment site. The presence of the CRGDS peptide provides a mechanism for integrin-mediated attachment to the scaffold that supports both cell spreading and movement.

Specifically, a monomer solution was prepared in PBS containing 6% wt/vol 20K 4-arm poly(ethylene glycol)-norbornene (PEG-NB), 1 mM adhesion peptide (CRGDS, SEQ ID NO: 48), 5.5 mM di-cysteine MMP-degradable crosslinker peptide (KCGPQGIAGQCK (SEQ ID NO: 46)), and 0.01% photoinitiator lithium phenyl-2,4,6-trimethylbenzoylphosphinate (LiAP). To create a hydrogel, 70 µl of the monomer solution was placed into a mold made by cutting 8 mm diameter holes in a 2 mm thick gasket that had been placed on a clean glass slide. Polymerization of the hydrogels was accomplished by shining a handheld LED flashlight emitting 385 nm light over the solution for 1 minute.

Step Growth Biomaterials for Delivery of Blood Fractions/Extracts

Example 16. Aggregation of Blood Extracts with High Weight % Monomer Solutions High molecular weight monomers of all types are known to cause precipitation of proteins and nucleic acids, likely due to their volume exclusion properties that effectively concentrate the proteins and nucleic acids. The effects of protein aggregation/precipitation would generally be perceived as deleterious in that the biological activity of the proteins in the blood extracts would be altered or reduced. Mixture of blood extracts with PEGs does not always result in measureable aggregation/precipitation, however, and several approaches can be used to prevent this effect. One approach is to reduce the overall weight percent of the PEG in solution.

A solution of 20% vol/vol of 20K4A-NB was prepared by resuspending powdered 20K4A-NB in water. Serial dilutions were the prepared, creating 20K4A-NB monomer solutions of 20%, 10%, 5%, and 2.5% wt/vol final concentrations. 100 ul of each monomer solution was then transferred into separate optically clear tubes. 25 ul of blood plasma, prepared as described in Example 7, was added to each tube, resulting in a final concentration of 20% vol/vol of the blood plasma. Each tube was mixed by inversion and allowed to sit at room temperature for 10 minutes. Visual inspection of the resultant plasma/PEG solution was then recorded. These results are presented in Table E4, below.

TABLE E4

Visual inspection of PEG/plasma mixtures.

| solution | volume | visual |
|---|---|---|
| 20% wt/vol PEG | 100 ul | (clear) |
| plasma | 25 ul | (clear) |
| PEG + plasma | 125 ul | (cloudy) |
| 10% wt/vol PEG | 100 ul | (clear) |
| plasma | 25 ul | (clear) |
| PEG + plasma | 125 ul | (cloudy) |
| 5% wt/vol PEG | 100 ul | (clear) |

TABLE E4-continued

Visual inspection of PEG/plasma mixtures.

| solution | volume | visual |
|---|---|---|
| plasma | 25 ul | (clear) |
| PEG + plasma | 125 ul | (cloudy) |
| 2.5% wt/vol PEG | 100 ul | (clear) |
| plasma | 25 ul | (clear) |
| PEG + plasma | 125 ul | (clear) |

As shown in Table E4, plasma to 20K4A PEG-NB monomer solution having weight percents greater than 5% wt/vol showed visible aggregation of the plasma. Only the PEG solution at 2.5% wt/vol did not show signs of protein precipitation when plasma was added.

Example 17. Loss of Growth Factors Due to High Molecular Weight Monomers

High molecular weight monomers of all types are known to cause precipitation of proteins and nucleic acids, likely due to their volume exclusion properties that effectively concentrate the proteins and nucleic acids. The effects of protein aggregation/precipitation would generally be perceived as deleterious in that the biological activity of the proteins in the blood extracts would be altered or reduced. Shorter PEG monomers were evaluated for use in a composition comprising a blood extract. One approach to reduce protein aggregation/precipitation from blood extracts when mixed with biomaterials is to use lower molecular weight monomers.

Preparation of Platelet Lysates.

Samples 1 (Unwashed Platelets) and Samples 2 & 3 (Washed Platelets) were prepared from a bag of ACD-anticoagulated platelets ($13.1*10^5$ platelets per microliter) that had been purchased from Bonfils center and processed under a BSL-2 hood. Two aliquots of 30 mL ($3.9*10^{10}$ platelets per tube) were centrifuged at 2,480×g for 8 min at to pellet platelets. One aliquot was used to prepare washed platelets by further resuspending pelleted platelets in 5 mL of buffer containing (130 mM NaCl, 2.7 mM KCl, 11.9 mM $NaHCO_3$, 5 mM Na-phosphate, 5.6 mM glucose, 1 mM $MgCl_2$, 10 mM Na-citrate, pH 6.5 at 23° C.) followed by centrifugation at 2,480×g for 5 minutes to pellet platelets; supernatant was discarded and the process was repeated one more time to yield pelleted washed platelets. Pelleted platelets were resuspended in 3.5 mL of PBS buffer pH 7.4 and lysed by three repeated freeze-thaw cycles (by immersing into a bath with dry ice and returning to ambient temperature), followed by sonication for 5 minutes in a sonicator bath. Cellular debris was removed by centrifugation at 14,000×g and clear lysates were used in subsequent experiments.

Human PDGF-BB ELISA.

To assess depletion of growth factors by addition of high-molecular weight PEG, 50 microliters of each of the lysates (from washed or unwashed platelets) were treated with 50 microliters of 12% wt solution of 8-arm PEG 40 kDa (final concentration of PEG 6% wt) for 5 minutes at ambient temperature. The samples were clarified by centrifugation at 14,000×g for 5 minutes and concentration of PDGF-BB in each sample before and after treatment with PEG was determined by ELISA after appropriate dilution (Quantikine ELISA kit, R & D systems). To assess depletion of growth factors by addition of lower molecular weight PEGs, 50 microliters of each of the lysates (from washed or unwashed platelets) were treated with 50 microliters of 16% wt/vol solution of linear PEGs of 200 Da, 400 Da, 600 Da, 1000 Da molecular weights (final concentration of PEG 6% wt) for 5 minutes at ambient temperature. The samples were clarified by centrifugation at 14,000×g for 5 minutes and concentration of PDGF-BB in each sample before and after treatment with PEG was determined by ELISA after appropriate dilution (Quantikine ELISA kit, R&D Systems)

Figure 11:
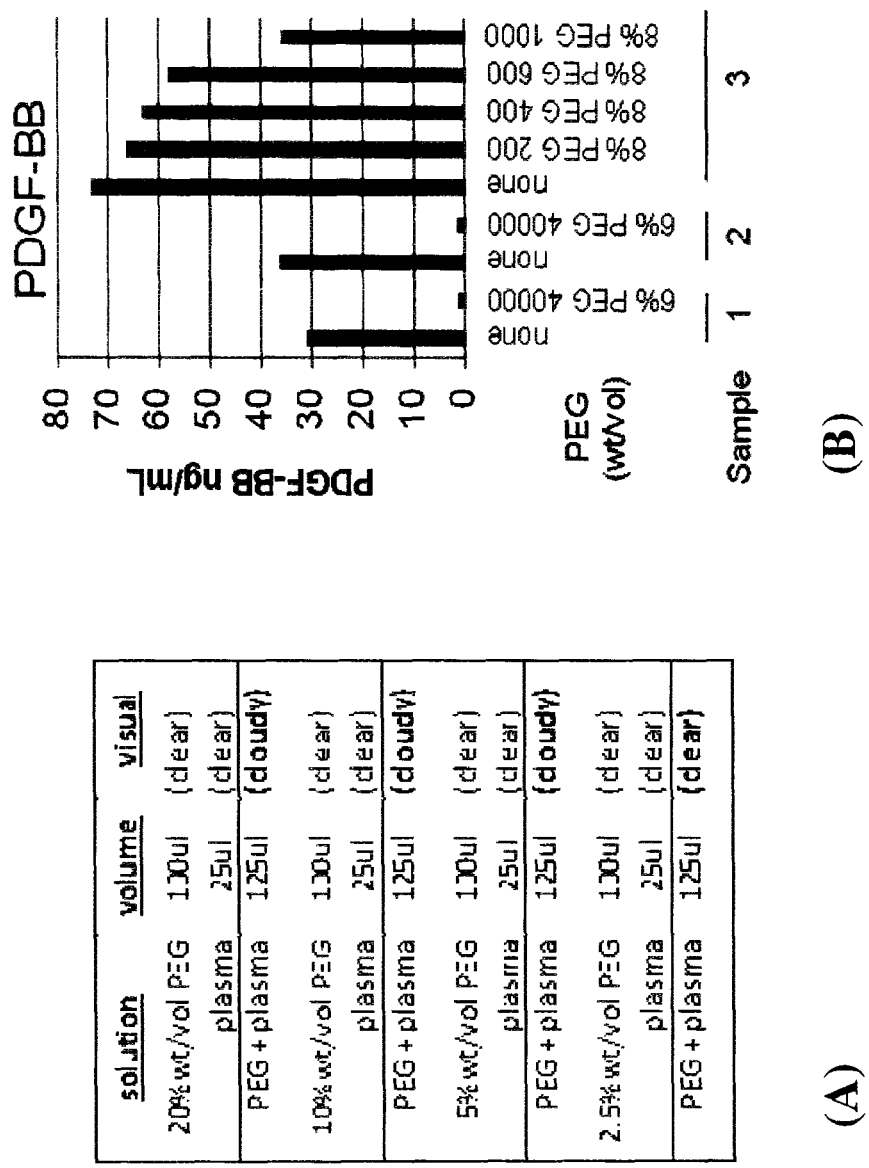
FIG. 11 illustrates PDGF-BB levels that were measured by ELISA after mixing blood extracts with PEG solutions using PEGs of various molecular weights.

As shown in FIG. 11, mixing blood extracts, platelet lysate in this case, with solutions containing large molecular weight PEGs (40,000 MW) reduces the levels of PDGF-BB in solution to almost undetectable levels (Samples 1 & 2). The effects of monomer size on PDGF-BB levels is more clearly illustrated with Sample 3, in which a blood extract was mixed with 8% wt/vol PEG solutions made with PEGs of molecular weights between 200 MW and 1000 MW. While the baseline PDGF-BB level in this sample was higher than that of Samples 1 & 2, the trend of increasing monomer size and loss of PDGF-BB in solution is evident. These data indicate that shorter PEG monomers prevent the precipitation of proteins in the blood extract that would occur with higher molecular weight PEG monomers.

Example 18. Comparison of Step-Growth, Chain Growth and Mixed Mode Polymerization Kinetics Photo-initiated polymerizations can typically proceed via a chain-growth, step-growth or mixed-mode polymerization mechanism. These mechanisms include different chemical steps and as a consequence follow different kinetics, may generate intermediates that are more or less toxic to tissues and biological molecules, and result in the polymeric networks with profoundly different mechanical and biological properties.

The following formulations of monomers were prepared in milli Q grade water and supplemented with 0.05 wt % (1.7 mM) of photoinitiator lithium phenyl-2,4,6-trimethylbenzoylphosphinate (LiAP):

"step": 4 wt % branched PEG tetranorbornene (average MW 20 kDa; 8 mM total norbornene concentration; 5 kDa of linear PEG per norbornene moiety) plus 4 mM dicysteine peptide crosslinker KCGPQGIAGQCK (SEQ ID NO: 46; 8 mM total thiol concentration, molar ratio of norbornene to thiol 1:1);

"chain": 4% linear PEG diacrylate (average MW 10 kDa; 8 mM total acrylate concentration; 5 kDa linear PEG per acrylate moiety);

"mixed 4:1": 4% linear PEG diacrylate (average MW 10 kDA; 8 mM total acrylate concentration; 5 kDa linear PEG per acrylate moiety) plus 1 mM dicysteine peptide crosslinker KCGPQGIAGQCK (SEQ ID NO: 46; 2 mM total thiol concentration; molar ratio of acrylate to thiol 4:1);

"mixed 1:1": 4% linear PEG diacrylate (average MW 10 kDA; 8 mM total acrylate concentration; 5 kDa linear PEG per acrylate moiety) plus 4 mM dicysteine peptide crosslinker KCGPQGIAGQCK (SEQ ID NO: 46; 8 mM total thiol concentration; molar ratio of acrylate to thiol 1:1).

In situ photopolymerization polymerization was followed in a fast oscillation time sweep tests on gelling solutions in a parallel-plate shear rheometer (TA Instruments Discovery HR-3; 8.0 mm diameter and 0.25 mm height). Time sweep tests were conducted at 6 rad/s with 1% strain, which was determined to be in the linear viscoelastic regime for both chain and step polymerized hydrogels. Polymerization was initiated 5 s after the start of time sweep experiment by a 365 nm light at 3 mW/cm² that was directed through a flat quartz plate through the sample. Polymerization was followed until the shear storage modulus (G') reached a plateau.

Figure 12:
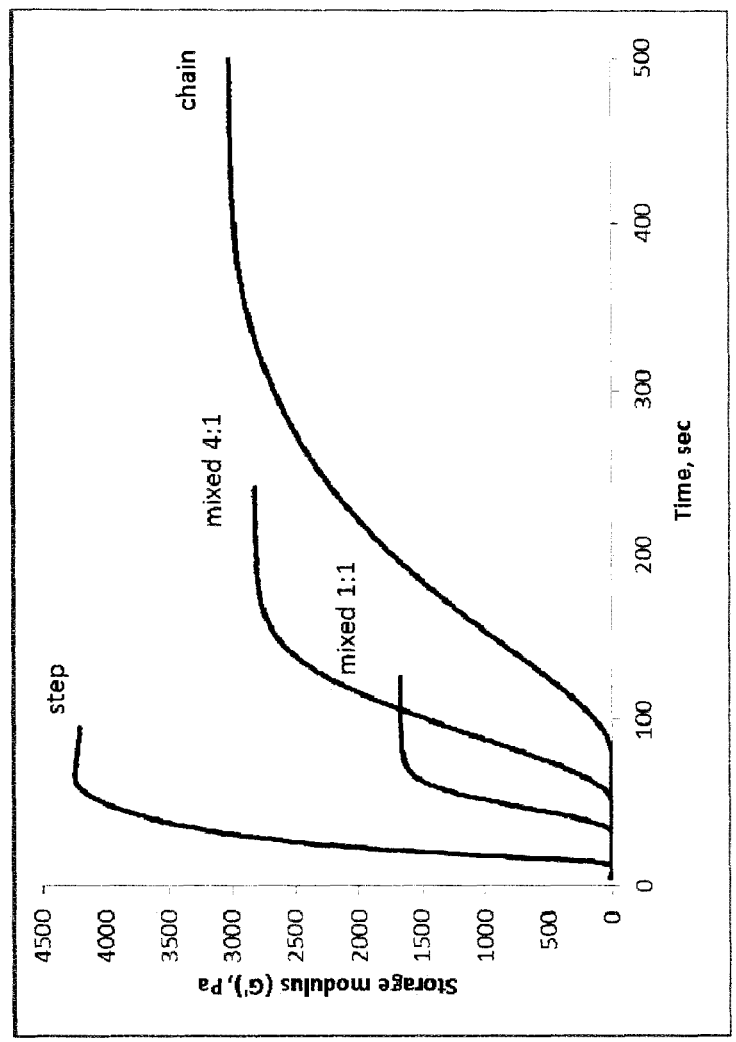
FIG. 12 shows a comparison of step-growth, chain growth and mixed mode polymerization kinetics. Four distinct formulations of monomers were prepared as step-growth, mixed-mode 1:1, mixed mode 4:1 or chain-growth networks and in situ photopolymerization kinetics were measured by shear rheometry.

Thiol-ene polymerizations are photochemically initiated, free-radical processes that take place between thiols and olefins via a sequential propagation/chain-transfer process. Thiol-ene polymerizations have a number of significant and unique advantages that make them particularly beneficial. These benefits include fast polymerization kinetics, very low radical concentration, low concentrations of photoinitiator and low dose of light required for polymerization to occur resulting in lesser damage to biological molecules, cells and tissues from these potentially toxic factors, the lack of oxygen inhibition and the ease with which monomers of significantly varying chemistry can be copolymerized. This is shown in FIG. 12, where kinetics of the formation and the elastic properties of the step-growth and chain-growth networks of similar monomer composition are compared side by side by shear rheometry in situ. Photo-induced polymerization of telechelic macromolecular monomers (4% PEG-diacrylate or 4% PEG-tetranorbornene in water) into a crosslinked network results in hydrogels with distinct mechano-elastic properties. The shear storage modulus (G') of the resulting networks reflects overall stiffness of the product hydrogels and may be related to the structural properties of these networks by polymer elasticity theories that are well known in the art. As clearly illustrated in FIG. 12, where the step-growth polymer ("step") is completely formed within one minute of irradiation at 385 nm at 3 mW/cm$^2$ (light intensity that is much lower than typically used in dental applications) while, under the same conditions, the chain-growth process exhibits a significant lag of about one and a half minute and reaches its maximal stiffness only after about 8 minutes of irradiation, with difference in irradiation time and necessary dose of UV light of almost an order of magnitude. Also note that the plateau value of the storage modulus for step-growth network (~4.2 kPa) is about 40% higher than for the chain growth network of similar composition (~3.0 kPa), indicating that step-growth network requires lower concentration of the material to generate a hydrogel of specific stiffness than the chain-growth network, a consideration important from a pharmacological standpoint.

Example 19. Degradation Products of Step-Growth and Mixed Mode-Polymerized Networks Photo-initiated polymerizations can typically proceed via a chain-growth, step-growth or mixed-mode polymerization mechanism. These mechanisms include different chemical steps and as a consequence follow different kinetics, may generate intermediates that are more or less toxic to tissues and biological molecules, and result in the polymeric networks with profoundly different mechanical and biological properties.

Figure 13:
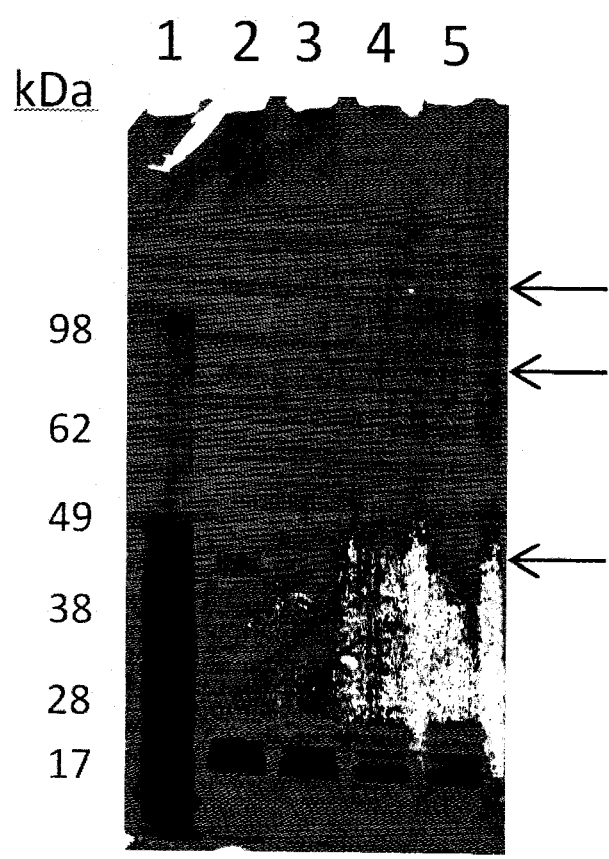
FIG. 13 illustrates the degradation product analysis of step-growth and mixed-mode networks examined by digesting hydrogels in 0.05% Trypsin. The degradation products were resolved by electrophoresis and examined by silver staining. Lanes: 1, SeeBlue Plus2 protein size standard (Invitrogen), molecular weights of protein standards are indicated on the left; 2: digested formulation "step"; 3: digested formulation "mixed 1:1"; 4: digested formulation "mixed 4:1"; 5: no hydrogel control (Trypsin in HBSS medium only).

The following formulations of monomers were prepared in milli Q grade water and supplemented with 0.05 wt % (1.7 mM) of photoinitiator lithium phenyl-2,4,6-trimethylbenzoylphosphinate (LiAP):
"step": 2 wt % branched PEG tetranorbornene (average MW 20 kDa; 4 mM total norbornene concentration; 5 kDa of linear PEG per norbornene moiety) plus 2 mM dicysteine peptide crosslinker CALKVLKGC (SEQ ID NO: 47; 2 mM total thiol concentration, molar ratio of norbornene to thiol 1:1);
"mixed 1:1": 2% linear PEG diacrylate (average MW 10 kDA; 4 mM total acrylate concentration; 5 kDa linear PEG per acrylate moiety) plus 2 mM dicysteine peptide cross-linker CALKVLKGC (SEQ ID NO: 47; 4 mM total thiol concentration; molar ratio of acrylate to thiol 1:1).
"mixed 4:1": 2% linear PEG diacrylate (average MW 10 kDA; 4 mM total acrylate concentration; 5 kDa linear PEG per acrylate moiety) plus 0.5 mM dicysteine peptide cross-linker CALKVLKGC (SEQ ID NO: 47; 1 mM total thiol concentration; molar ratio of acrylate to thiol 4:1);

Hydrogels were photopolymerized in 100 microliter cylindrical molds upon irradiation with 385 nm light delivered at 2 mW/cm$^2$ for the time sufficient to achieve complete polymer formation as judged by in situ rheometry experiments similar to described in Example A. Each 100 microliter hydrogel was then cut in 4 pieces of equal size (~25 microliter) with a sterile razor blade. The 25 microliter hydrogel pieces were immersed into 200 microliter solution containing 0.05% Trypsin in HBSS medium (Cellgro) in 1.5 mL Eppendorf tubes and incubated at 37° C. for 4 hrs 30 mM; a no-hydrogel control containing just 0.05% Trypsin in HBSS medium was included. Complete dissolution of all hydrogel pieces was observed within the first 2 hours of enzymatic treatment. Aliquots of the digested material were diluted 20-fold into a LDS gel loading buffer (Invitrogen) and analyzed by electrophoresis in a 4-12% gradient Novex NuPage protein gel (Invitrogen). Gel was processed by silver staining with SilverQuest staining kit from Invitrogen. An image of the gel is shown in FIG. 13, where the lanes were loaded as follows: Lanes: 1, SeeBlue Plus2 protein size standard (Invitrogen), molecular weights of protein standards are indicated on the left; 2: digested formulation "step"; 3: digested formulation "mixed 1:1"; 4: digested formulation "mixed 4:1"; 5: no hydrogel control (Trypsin in HBSS medium only). Note the well-resolved bands at about 40 kDa, 80 kDa and 120 kDa in the lane 2 ("step") indicated by arrows on the right. These are the products of enzymatic degradation of the step-growth network, corresponding to peptide fragments covalently attached to 4-arm PEG 20 kDa lowest arrow), and incompletely digested dimeric and trimeric products (higher up). Note that branched polymers (e.g. charged derivatives of 4-arm PEG) typically migrate slower than the linear ones upon electrophoresis in polyacrylamide gels, which explains why ~20 kDa branched degradation product migrates between the 38 kDa and 49 kDa linear protein standards. Note that no degradation products can be detected in the lanes 3 and 4 (mixed mode hydrogels) despite complete digestion of these hydrogels, indicating that non-degradable, kinetic chains-containing fragments formed upon the chain-growth polymerization phase of these hydrogels are too large to enter the protein gel upon electrophoresis, suggesting that the lower size limit for these fragments exceeds 200 kDa (highest molecular weight that can be resolved in this protein gel).

Example 20. Fibroblast Outgrowth into Scaffolds Formed by Step and Chain-Growth Polymerizations Photo-initiated polymerizations can typically proceed via a chain-growth, step-growth or mixed-mode polymerization mechanism. These mechanisms include different chemical steps and as a consequence follow different kinetics, may generate intermediates that are more or less toxic to tissues and biological molecules, and result in the polymeric networks with profoundly different mechanical and biological properties.

The following formulations of monomers were prepared in PBS buffer pH 7.4 and supplemented with 0.05 wt % (1.7 mM) of photoinitiator lithium phenyl-2,4,6-trimethylbenzoylphosphinate (LiAP) and 30% human plasma:

"step": 2 wt % branched PEG tetranorbornene (average MW 20 kDa; 4 mM total norbornene concentration; 5 kDa of linear PEG per norbornene moiety) plus 2 mM dicysteine peptide crosslinker KCGPQGIAGQCK (SEQ ID NO: 46; 4 mM total thiol concentration, molar ratio of norbornene to thiol 1:1);
"chain": 2% linear PEG diacrylate (average MW 10 kDA; 4 mM total acrylate concentration; 5 kDa linear PEG per acrylate moiety);
"mixed 4:1": 2% linear PEG diacrylate (average MW 10 kDA; 4 mM total acrylate concentration; 5 kDa linear PEG per acrylate moiety) plus 0.5 mM dicysteine peptide crosslinker KCGPQGIAGQCK (SEQ ID NO: 46; 1 mM total thiol concentration; molar ratio of acrylate to thiol 4:1);
"mixed 1:1": 2% linear PEG diacrylate (average MW 10 kDA; 4 mM total acrylate concentration; 5 kDa linear PEG per acrylate moiety) plus 2 mM dicysteine peptide crosslinker KCGPQGIAGQCK (SEQ ID NO:46; 4 mM total thiol concentration; molar ratio of acrylate to thiol 1:1).

Human dermal fibroblasts were encapsulated in collagen plugs as disclosed elsewhere in present application. Cell-containing plugs were immersed in 400 microliters of the monomer formulations and photopolymerized inside the wells of a standard 24-well tissue culture plate. Immediately after photopolymerization, 1 mL of DMEM medium supplemented with 10% foetal bovine serum was added to each well and cells were incubated under standard growth conditions (37° C., 5% $CO_2$) in a tissue culture incubator. After 24 hours of incubation, fibroblast outgrowth from collagen plugs into the material was evaluated microscopically, and scored on a scale from 0 to 5, where 0 stands for no detectable outgrowth and 5 represents outgrowth from a collagen plug into a fresh collagen hydrogel. The data are summarized in the following table.

TABLE E5

Outgrowth scores of fibroblasts in distinct biomaterials.

|  | Outgrowth score |
| --- | --- |
| step | 3 |
| mixed (1:1) | 0 |
| mixed (4:1) | 0 |
| chain | 0 |

As shown in Table E5, only hydrogels with these components produced from thiol-ene step-growth polymerization provided a scaffold through which cells could migrate.

Figure 14:
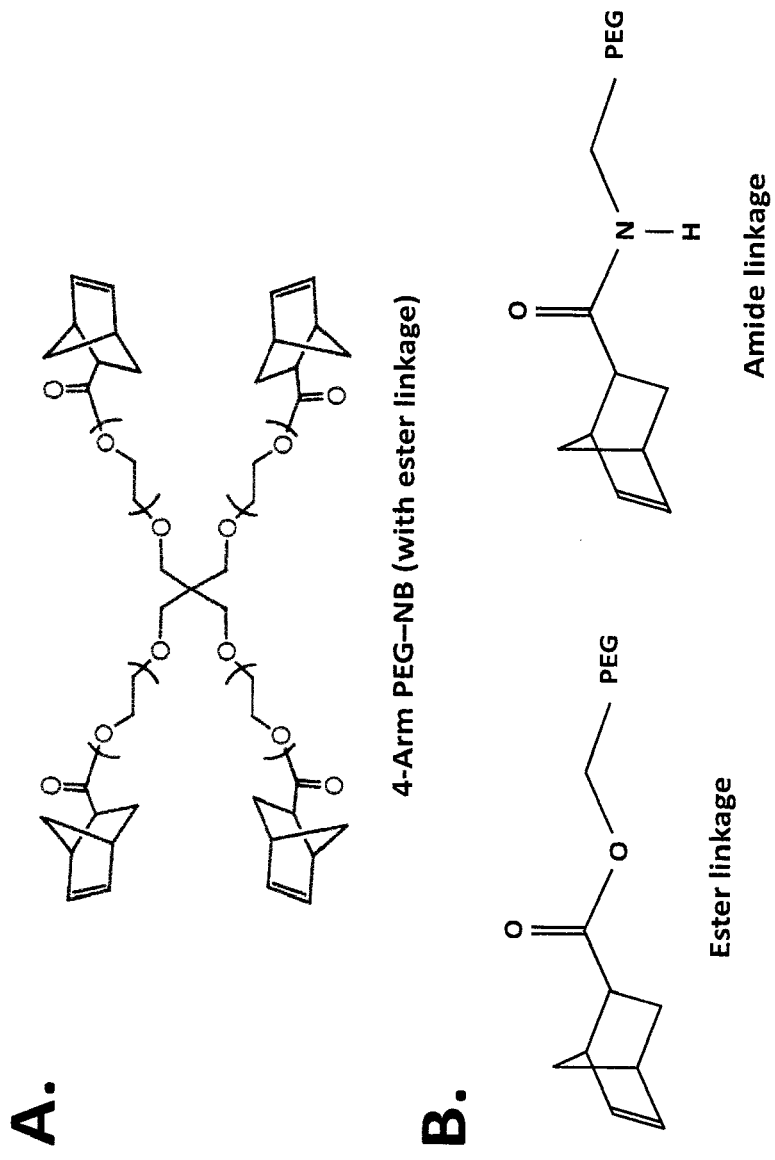
FIG. 14 illustrates norbornene-functionalized PEGS.
Figure 15:
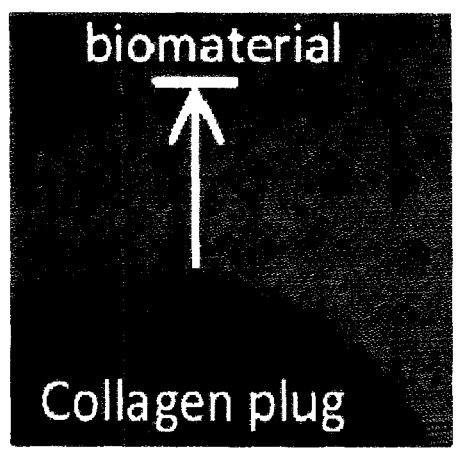
FIG. 15 illustrates the results of a cellular outgrowth assay. Human dermal fibroblasts (HDF) were polymerized in a type I collagen gel and allowed to contract over 72 hours. The resulting collagen-cell plug is embedded into a biomaterial to evaluate the biological activity of materials to which blood extracts have been added. Cellular migration can be seen as cells move away from the plug into the biomaterial. The distance cells move away from the plug can be measured over time.
Figure 16:
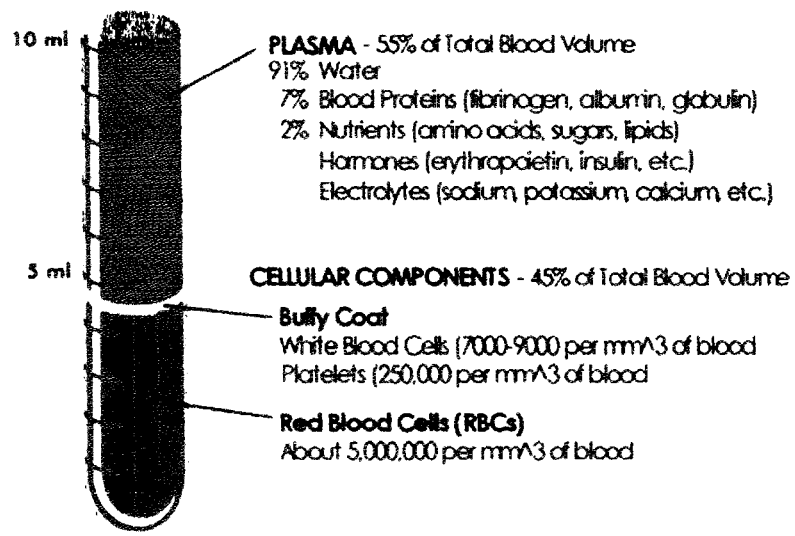
FIG. 16 provides an illustration of centrifugation-based fractionation of whole blood to separate plasma, buffy coat, and red blood cells.

Example 21. Synthesis of Ester-Linked 4-Arm PEG-Norbornene 10 g of 4 arm poly(ethyleneglycol) (PEG; average MW 10 kDa; 4 mmol amino groups) in a round bottom flask equipped with a Teflon-coated magnetic stir bar was dried overnight under vacuum at 40° C. To the dried PEG 50 mg (0.4 mmol) of dimethylaminopyridine (DMAP) was added, the flask was sealed with rubber septum and purged with a flow of argon; during all subsequent procedures small excess pressure of argon was maintained in the flask in order to ensure anhydrous atmosphere. Into the sealed flask, 40 mL of anhydrous dichloromethane (DCM) was injected through the septum followed by injection of 3.2 mL anhydrous pyridine and the PEG was dissolved upon vigorous stirring. In a separate sealed, argon-purged flask 100 mg (0.8 mmol) DMAP, 7.2 mL (40 mmol) of N—N'-diisopropylcarbodiimide (DIC) and 11.3 g (80 mmol) of 5-norbornene-2-carboxylic acid (NBA) were dissolved in 30 mL of anhydrous DCM upon stirring and the resulting mixture was allowed to stir under a flow of argon for 15 minutes at ambient temperature in order to convert NBA into an anhydride. The PEG and DMAP solution in DCM was then anhydrously transferred into the round bottom flask containing the NBA anhydride and resulting reaction mixture was stirred overnight at ambient temperature under a flow of argon. The product was precipitated by addition of tenfold excess of diethyl ether, recovered by filtration and re-precipitated from DCM with tenfold excess of diethyl ether one more time. The degree of conversion of PEG into the ester-linked product was assessed by one-dimensional proton NMR in deuterated chloroform ($CDCl_3$) at 400 MHz and was found to be at least 93%. A diagram of the chemical structure of the resultant 4-arm PEG-NB is shown in FIG. 14.

Example 22. Synthesis of Amide-Linked 4-Arm PEG-Norbornene 5 g of 4 arm PEG tetra-amine (average MW 20 kDa; 1 mmol amino groups) in a round bottom flask equipped with a Teflon-coated magnetic stir bar was dried overnight under vacuum at 40° C. The flask was sealed with rubber septum and purged with a flow of argon; during all subsequent procedures small excess pressure of argon was maintained in the flask in order to ensure anhydrous atmosphere. Into the sealed flask with PEG tetra-amine, a sparing amount of anhydrous dimethylformamide (DMF) was injected through the septum and the PEG-amine was dissolved upon vigorous stirring. In a separate sealed, argon-purged flask 0.76 g (2 mmol) of O-(7-azabenzotriazol-1-yl)-N,N,N',N'-tetramethyluronium hexafluorophosphate (HATU) and 0.24 g (2 mmol) of 5-norbornene-2-carboxylic acid (NBA) were dissolved in a sparing amount of DMF upon stirring. To the solution of HATU and NBA in DMF, 0.5 g (4 mmol) of N,N-Diisopropylethylamine (DIEA) was added via injection through the septum and the resulting mixture was allowed to stir under a flow of argon for 5 minutes at ambient temperature in order to activate NBA. This solution of activated NBA was then anhydrously transferred into the round bottom flask containing the DMF solution of PEG tetra-amine and resulting reaction mixture was stirred overnight at ambient temperature under a flow of argon. The solvent was then removed by evaporation at reduced pressure, crude product dissolved in deionized water, transferred into SpectraPor 7 dialysis tubing (MWCO 1000 Da) and dialyzed for 3 days against deionized water, with water being changed three times per day. Dialyzed solution was lyophilized to furnish dry product. The degree of conversion of PEG tetra-amine into the final product was assessed by one-dimensional proton NMR in deuterated chloroform ($CDCl_3$) at 400 MHz and was found to be at least 95%. A diagram of the chemical structure of a 4-arm PEG-NB (with ester linkage) is shown in FIG. 14A. FIG. 14B illustrates the amide linkage described in this example.

Example 23. Prophetic Combination of Plasma and Serum Provides Substrate for Cellular Migration and Activating Growth Factors when Combined with Biomaterials An important aspect of tissue repair and regeneration is the infiltration of cells from the body into the injury or defect site. Therefore, biomaterials and/or extract-biomaterial combinations must support cellular migration, a process that requires cells to interact with the insoluble extracellular matrix (ECM). In addition, chemoattractant factors aid to stimulate cellular migration and recruit cellular infiltration. Traditionally, tissue engineers have used simple ECM mimics (eg. RGD) to provide cellular adhesion motifs to their biomaterials, allowing cells to both hold on to the matrix as well as generate forces that result in migration. In vitro cell culture experiments often rely on the addition of serum (eg. FBS) to culture media in order to stimulate cellular activity (proliferation, migration, etc.). Combinations of plasma and serum with biomaterials would provide both the scaffolding properties of proteins found in plasma as well as the growth factor-mediated induction of cellular activity. In order to evaluate the ability of plasma and serum to support migratory responses of cells into synthetic biomaterial lacking cell adhesion moieties, a collagen plug assay was utilized:

Preparation of Whole Blood Fractions.

Plasma and serum are prepared as described in Examples 7 and 8, respectively.

Biomaterial Preparation.

A monomer solution is prepared as described in Example 2.

Blood Fraction/Biomaterial Mixture.

Plasma and serum fractions are mixed with the monomer solution as described in Example 2. In addition, one sample is created in which both plasma and serum are added. Supplementation of the serum fraction with anticoagulant (ACD, EGTA, etc.) before mixing with the plasma sample is performed to prevent clotting factors found in serum from activating coagulation of plasma proteins.

Cellular Outgrowth Assay.

As cellular outgrowth assay is performed with these samples as described in Example 3 (using serum-free media).

Example 24. Prophetic Polymerization of Thiol-Ene Hydrogels with Light-Independent Free Radical Mechanism Monomer solutions is prepared in PBS containing 6% wt/vol 20K 4-arm poly(ethylene glycol)-norbornene (PEG-NB), 6 mM di-cysteine enzymatically degradable cross-linker peptide (KCGPQGIAGQCK (SEQ ID NO: 46)), 11 mM glucose, and 4 mM $FeCl_2$. In this system, cysteine-containing peptides and 4-arm PEG-NB monomers are mixed in a 1:1 stoichiometric ratio with respect to "thiol" and "ene" functional groups. In the presence of free radicals, the thiol group adds to the norbornene, forming a norbornene-thioether linkage. To create a hydrogel, Glucose Oxidase (GuOx) is added to the monomer solution at a final concentration of 50 uM and then mixed by vortexing. 70 µl of the monomer solution is then placed immediately into a mold made by cutting 8 mm diameter holes in a 2 mm thick gasket placed on a clean glass slide. Polymerization of the hydrogels occurs as GuOx oxidizes the glucose in the monomer solution and creates free radicals. These radicals abstract hydrogens from the cysteine thiols on the cross-linker peptides, creating thiyl radicals that then participate in the thiol-ene polymerization reaction.

Example 25. Prophetic Polymerization of Thiol-Ene Hydrogels with Both Light-Dependent and Light-Independent Free Radical Mechanisms Monomer solutions is prepared in PBS containing 6% wt/vol 20K 4-arm poly(ethylene glycol)-norbornene (PEG-NB), 6 mM di-cysteine enzymatically degradable cross-linker peptide (KCGPQGIAGQCK (SEQ ID NO: 46)), 11 mM glucose, 4 mM $FeCl_2$, and 0.01% photoinitiator lithium phenyl-2,4,6-trimethylbenzoylphosphinate (LAP or LiAP). In this system, cysteine-containing peptides and 4-arm PEG-NB monomers are mixed in a 1:1 stoichiometric ratio with respect to "thiol" and "ene" functional groups. In the presence of free radicals, the thiol group adds to the norbornene, forming a norbornene-thioether linkage. To create a hydrogel, Glucose Oxidase (GuOx) is added to the monomer solution at a final concentration of 50 uM and then mixed by vortexing. 70 µl of the monomer solution is then placed immediately into a mold made by cutting 8 mm diameter holes in a 2 mm thick gasket placed on a clean glass slide. Gelation of hydrogels is accomplished by shining a handheld LED flashlight emitting 385 nm light over the solution for 30 seconds. Continued polymerization of the hydrogels occurs as GuOx oxidizes the glucose in the monomer solution and creates additional free radicals. These radicals abstract hydrogens from the cysteine thiols on the cross-linker peptides, creating thiyl radicals that then participate in the thiol-ene polymerization reaction. In this example, a light-mediated initiation reaction is used to rapidly cure the biomaterial, and a light-independent mechanism is used to ensure that the polymerization reactions go to completion, or near-completion. This would be advantageous when applying a biomaterial to a location in which the photinitiating light is partially obstructed or diminished such as deep, tunneling wounds or wounds where the presence of red blood cells attenuates light wavelengths necessary for the initiation of polymerizing chemistries.

Other sequences noted herein include SEQ ID NOS: 39-48.

| SEQ ID | Sequence | trivial name |
|---|---|---|
| SEQ ID: 39 | ALKVLKG | |
| SEQ ID: 40 | SFLLRN | PAR1-AP |
| SEQ ID: 41 | TFLLR | PAR1-AP |
| SEQ ID: 42 | GYPGKF | PAR4-AP |
| SEQ ID: 43 | AYPGK | PAR4-AP |
| SEQ ID: 44 | AYPGKF | PAR4-AP |
| SEQ ID: 45 | KCGPQGIWGQCK | MMPW |
| SEQ ID: 46 | KCGPQGIAGQCK | MMPA |
| SEQ ID: 47 | CALKVLKGC | C2xPC |
| SEQ ID: 48 | CRGDS | CRGDS |

EQUIVALENTS

Those skilled in the art will recognize, or be able to ascertain using no more than routine experimentation, many equivalents to the specific embodiments of the invention described herein. Such equivalents are intended to be encompassed by the following claims.

INCORPORATION BY REFERENCE

The Sequence Listing submitted in an ASCII text file, in accordance with 37 C.F.R. § 1.821(c) and (e), is incorporated by herein by reference. The text file name is "700032000500_Sequence_Listing.txt", the date of creation of the text file is Feb. 4, 2013, and the size of the ASCII text file in bytes is 9,084.

All patents, publications or other references listed herein are incorporated herein by reference in their entireties.

The invention claimed is:

1. A composition for treating a skin wound, orthopedic condition, pain, nerve injury, tendinitis, osteoarthritis, cardiac muscle injury, bone injury, traumatic injury or dental injury comprising (i) a polymeric biomaterial and (ii) a blood extract encapsulated within the polymeric biomaterial;
   wherein the polymeric biomaterial is fully synthetic, is degradable, and yields defined degradation products;
   wherein the polymeric biomaterial is formed by photopolymerization of a first monomer comprising at least two thiol moieties and a second monomer comprising at least two alkene moieties or at least one alkyne moiety; and
   wherein the encapsulated blood extract comprises at least 1000 platelets.

2. The composition of claim 1, wherein the second monomer comprises at least two alkene moieties.

3. The composition of claim 1, wherein the second monomer comprises at least one alkyne moiety.

4. The composition of claim 1, wherein at least one of the first monomer and the second monomer is selected from the group consisting of poly(lactic acid) (PLA), polyglycolide (PGA), a copolymer of PLA and PGA (PLGA), poly(vinyl alcohol) (PVA), poly(ethylene glycol) (PEG), poly(ethylene oxide), poly(ethylene oxide)-co-poly(propylene oxide) block copolymer, poloxamines, polyanhydrides, polyorthoesters, poly(hydroxy acids), polydioxanones, polycarbonates, polyaminocarbonates, poly(vinyl pyrrolidone), poly(ethyl oxazoline), carboxymethyl cellulose, hydroxyalkylated cellulose nucleic acids, polypeptides, polysaccharides or carbohydrates, heparan sulfate, chondroitin sulfate, heparin, or alginate, and proteins, or copolymers, or blends thereof;
   wherein the first monomer has or is derivatized to incorporate at least two thiol moieties; and
   wherein the second monomer has or is derivatized to incorporate at least two alkene moieties or at least one alkyne moiety.

5. The composition of claim 1, wherein at least one of the first monomer and the second monomer is selected from poly(lactic acid) (PLA), poly(vinyl alcohol) (PVA), and poly(ethylene glycol) (PEG);
   wherein the first monomer has or is derivatized to incorporate at least two thiol moieties; and
   wherein the second monomer has or is derivatized to incorporate at least two alkene moieties or at least one alkyne moiety.

6. The composition of claim 1, wherein the biomaterial is a hydrogel comprising greater than about 50% water by weight.

7. The composition of claim 1, wherein at least one of the first monomer and the second monomer comprises a peptide.

8. The composition of claim 1, further comprising an additional agent.

9. The composition of claim 8, wherein the additional agent is a peptide selected from the group consisting of adhesion peptides, growth factors, hormones, antihormones, signaling compounds, enzymes, serum proteins, albumins, macroglobulins, globulins, agglutinins, lectins, extracellular matrix proteins, antibodies, and antigens or a non-peptide agent selected from the group consisting of analgesics, anti-pyretics, non-steroidal anti-inflammatory drugs, anti-allergics, antibacterial drugs, antifungal, antimicrobial, anti-anemia drugs, cytotoxic drugs, antihypertensive drugs, dermatological drugs, psychotherapeutic drugs, vitamins, minerals, anorexiants, dietetics, anti-adiposity drugs, carbohydrate metabolism drugs, protein metabolism drugs, thyroid drugs, anti-thyroid drugs, and coenzymes.

10. The composition of claim 1, wherein the second monomer is a norbornene derived PEG monomer and the first monomer is a peptide monomer, wherein the peptide monomer comprises at least two thiol moieties.

11. The composition of claim 1, wherein the biomaterial is a step-growth polymer formed by the polymerization of a norbornene derived PEG monomer and a peptide monomer, wherein the peptide monomer comprises at least two thiol moieties.

12. The composition of claim 1, wherein the at least 1000 platelets are not substantially activated.

13. The composition of claim 1, wherein the photopolymerization is initiated by a photoinitiator.

14. The composition of claim 13, wherein the photoinitiator is selected from the group consisting of lithium phenyl-2,4,6-trimethylbenzoylphosphinate (LiAP) and sodium phenyl-2,4,6-trimethylbenzoylphosphinate (NaAP).

15. A method of treating a skin wound, orthopedic condition, pain, nerve injury, tendinitis, osteoarthritis, cardiac muscle injury, bone injury, traumatic injury or dental injury in an individual an effective amount of comprising administering to the individual the composition of claim 1.

16. A kit comprising the composition of claim 1 and instructions for use.

17. An article of manufacture comprising an effective amount of the composition of claim 1.

18. The composition of claim 2, wherein the at least two alkene moieties are each a norbornene moiety.

19. The composition of claim 1, wherein the encapsualted blood extract comprises at least $1 \times 10^9$ platelets.

20. The composition of claim 1, wherein the polymeric biomaterial is enzymatically degradable.

21. The composition of claim 1, wherein the at least 1000 platelets are not activated.

* * * * *

SEQUENCE LISTING

<160> NUMBER OF SEQ ID NOS: 48

<210> SEQ ID NO 1
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3, 4, 5, 6, 7, 8
<223> OTHER INFORMATION: Xaa = Any Amino Acid

<400> SEQUENCE: 1

Tyr Cys Xaa Xaa Xaa Xaa Xaa Xaa Cys Tyr
1               5                   10

<210> SEQ ID NO 2
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2, 3, 4, 5, 6, 7
<223> OTHER INFORMATION: Xaa = Any Amino Acid

<400> SEQUENCE: 2

Cys Xaa Xaa Xaa Xaa Xaa Xaa Cys
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 2, 3, 4, 5, 6
<223> OTHER INFORMATION: Xaa = Any Amino Acid

<400> SEQUENCE: 3

Xaa Xaa Xaa Xaa Xaa Xaa
1               5

<210> SEQ ID NO 4
<211> LENGTH: 13
<212> TYPE: PRT
<213> ORGANISM: Artificial Sequence
<220> FEATURE:
<221> NAME/KEY: VARIANT
<222> LOCATION: 2, 3, 4, 5, 6, 8, 9, 10, 11, 12
<223> OTHER INFORMATION: Xaa = Any Amino Acid

<400> SEQUENCE: 4

Cys Xaa Xaa Xaa Xaa Xaa Cys Xaa Xaa Xaa Xaa Xaa Cys
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2, 3, 4, 5, 6
<223> OTHER INFORMATION: Xaa = Any Amino Acid

```
<400> SEQUENCE: 5

Cys Xaa Xaa Xaa Xaa Xaa Cys
1               5

<210> SEQ ID NO 6
<211> LENGTH: 13
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2, 3, 4, 5, 6, 8, 9, 10, 11, 12
<223> OTHER INFORMATION: Xaa = Any Amino Acid

<400> SEQUENCE: 6

Tyr Xaa Xaa Xaa Xaa Xaa Tyr Xaa Xaa Xaa Xaa Xaa Tyr
1               5                   10

<210> SEQ ID NO 7
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 2, 3, 4, 5
<223> OTHER INFORMATION: Xaa = Any Amino Acid

<400> SEQUENCE: 7

Xaa Xaa Xaa Xaa Xaa
1               5

<210> SEQ ID NO 8
<211> LENGTH: 6
<212> TYPE: PRT
<213> ORGANISM: Artificial Sequence
<220> FEATURE:
<223> OTHER INFORMATION: Synthetic Construct

<400> SEQUENCE: 8

Gly Pro Arg Val Val Glu
1               5

<210> SEQ ID NO 9
<211> LENGTH: 6
<212> TYPE: PRT
<213> ORGANISM: Artificial Sequence
<220> FEATURE:
<223> OTHER INFORMATION: Synthetic Construct

<400> SEQUENCE: 9

Asn Asn Arg Asp Asn Thr
1               5

<210> SEQ ID NO 10
<211> LENGTH: 6
<212> TYPE: PRT
<213> ORGANISM: Artificial Sequence
<220> FEATURE:
<223> OTHER INFORMATION: Synthetic Construct

<400> SEQUENCE: 10

Tyr Asn Arg Val Ser Glu
1               5
```

```
<210> SEQ ID NO 11
<211> LENGTH: 6
<212> TYPE: PRT
<213> ORGANISM: Artificial Sequence
<220> FEATURE:
<223> OTHER INFORMATION: Synthetic Construct

<400> SEQUENCE: 11

Gln Met Arg Met Glu Leu
1               5

<210> SEQ ID NO 12
<211> LENGTH: 6
<212> TYPE: PRT
<213> ORGANISM: Artificial Sequence
<220> FEATURE:
<223> OTHER INFORMATION: Synthetic Construct

<400> SEQUENCE: 12

Gly Phe Arg His Arg His
1               5

<210> SEQ ID NO 13
<211> LENGTH: 6
<212> TYPE: PRT
<213> ORGANISM: Artificial Sequence
<220> FEATURE:
<223> OTHER INFORMATION: Synthetic Construct

<400> SEQUENCE: 13

Gly Tyr Arg Ala Arg Pro
1               5

<210> SEQ ID NO 14
<211> LENGTH: 6
<212> TYPE: PRT
<213> ORGANISM: Artificial Sequence
<220> FEATURE:
<223> OTHER INFORMATION: Synthetic Construct

<400> SEQUENCE: 14

Tyr Gln Lys Asn Asn Lys
1               5

<210> SEQ ID NO 15
<211> LENGTH: 6
<212> TYPE: PRT
<213> ORGANISM: Artificial Sequence
<220> FEATURE:
<223> OTHER INFORMATION: Synthetic Construct

<400> SEQUENCE: 15

Leu Ile Lys Met Lys Pro
1               5

<210> SEQ ID NO 16
<211> LENGTH: 6
<212> TYPE: PRT
<213> ORGANISM: Artificial Sequence
<220> FEATURE:
<223> OTHER INFORMATION: Synthetic Construct

<400> SEQUENCE: 16

Asn Phe Lys Ser Gln Leu
1               5
```

```
<210> SEQ ID NO 17
<211> LENGTH: 6
<212> TYPE: PRT
<213> ORGANISM: Artificial Sequence
<220> FEATURE:
<223> OTHER INFORMATION: Synthetic Construct

<400> SEQUENCE: 17

Glu Trp Lys Ala Leu Thr
1               5

<210> SEQ ID NO 18
<211> LENGTH: 6
<212> TYPE: PRT
<213> ORGANISM: Artificial Sequence
<220> FEATURE:
<223> OTHER INFORMATION: Synthetic Construct

<400> SEQUENCE: 18

Ser Tyr Lys Met Ala Asp
1               5

<210> SEQ ID NO 19
<211> LENGTH: 6
<212> TYPE: PRT
<213> ORGANISM: Artificial Sequence
<220> FEATURE:
<223> OTHER INFORMATION: Synthetic Construct

<400> SEQUENCE: 19

Thr Gln Lys Lys Val Glu
1               5

<210> SEQ ID NO 20
<211> LENGTH: 6
<212> TYPE: PRT
<213> ORGANISM: Artificial Sequence
<220> FEATURE:
<223> OTHER INFORMATION: Synthetic Construct

<400> SEQUENCE: 20

Arg Gln Lys Gln Val Lys
1               5

<210> SEQ ID NO 21
<211> LENGTH: 6
<212> TYPE: PRT
<213> ORGANISM: Artificial Sequence
<220> FEATURE:
<223> OTHER INFORMATION: Synthetic Construct

<400> SEQUENCE: 21

Gln Val Lys Asp Asn Glu
1               5

<210> SEQ ID NO 22
<211> LENGTH: 6
<212> TYPE: PRT
<213> ORGANISM: Artificial Sequence
<220> FEATURE:
<223> OTHER INFORMATION: Synthetic Construct

<400> SEQUENCE: 22

Leu Ile Lys Ala Ile Gln
1               5

<210> SEQ ID NO 23
```

```
<211> LENGTH: 6
<212> TYPE: PRT
<213> ORGANISM: Artificial Sequence
<220> FEATURE:
<223> OTHER INFORMATION: Synthetic Construct

<400> SEQUENCE: 23

Thr Leu Lys Ser Arg Lys
1               5

<210> SEQ ID NO 24
<211> LENGTH: 6
<212> TYPE: PRT
<213> ORGANISM: Artificial Sequence
<220> FEATURE:
<223> OTHER INFORMATION: Synthetic Construct

<400> SEQUENCE: 24

Ser Arg Lys Met Leu Glu
1               5

<210> SEQ ID NO 25
<211> LENGTH: 6
<212> TYPE: PRT
<213> ORGANISM: Artificial Sequence
<220> FEATURE:
<223> OTHER INFORMATION: Synthetic Construct

<400> SEQUENCE: 25

Pro Gln Gly Ile Ala Gly
1               5

<210> SEQ ID NO 26
<211> LENGTH: 6
<212> TYPE: PRT
<213> ORGANISM: Artificial Sequence
<220> FEATURE:
<223> OTHER INFORMATION: Synthetic Construct

<400> SEQUENCE: 26

Pro Gln Gly Leu Leu Gly
1               5

<210> SEQ ID NO 27
<211> LENGTH: 6
<212> TYPE: PRT
<213> ORGANISM: Artificial Sequence
<220> FEATURE:
<223> OTHER INFORMATION: Synthetic Construct

<400> SEQUENCE: 27

Pro Gln Gly Ile Leu Gly
1               5

<210> SEQ ID NO 28
<211> LENGTH: 6
<212> TYPE: PRT
<213> ORGANISM: Artificial Sequence
<220> FEATURE:
<223> OTHER INFORMATION: Synthetic Construct

<400> SEQUENCE: 28

Pro Gln Gly Leu Ala Gly
1               5

<210> SEQ ID NO 29
<211> LENGTH: 6
```

```
<212> TYPE: PRT
<213> ORGANISM: Artificial Sequence
<220> FEATURE:
<223> OTHER INFORMATION: Synthetic Construct

<400> SEQUENCE: 29

Pro Leu Gly Ile Ala Gly
1               5

<210> SEQ ID NO 30
<211> LENGTH: 6
<212> TYPE: PRT
<213> ORGANISM: Artificial Sequence
<220> FEATURE:
<223> OTHER INFORMATION: Synthetic Construct

<400> SEQUENCE: 30

Pro Leu Gly Leu Trp Ala
1               5

<210> SEQ ID NO 31
<211> LENGTH: 6
<212> TYPE: PRT
<213> ORGANISM: Artificial Sequence
<220> FEATURE:
<223> OTHER INFORMATION: Synthetic Construct

<400> SEQUENCE: 31

Pro Leu Gly Leu Ala Gly
1               5

<210> SEQ ID NO 32
<211> LENGTH: 8
<212> TYPE: PRT
<213> ORGANISM: Artificial Sequence
<220> FEATURE:
<223> OTHER INFORMATION: Synthetic Construct

<400> SEQUENCE: 32

Gly Pro Gln Gly Ile Ala Gly Gln
1               5

<210> SEQ ID NO 33
<211> LENGTH: 8
<212> TYPE: PRT
<213> ORGANISM: Artificial Sequence
<220> FEATURE:
<223> OTHER INFORMATION: Synthetic Construct

<400> SEQUENCE: 33

Gly Pro Val Gly Ile Ala Gly Gln
1               5

<210> SEQ ID NO 34
<211> LENGTH: 8
<212> TYPE: PRT
<213> ORGANISM: Artificial Sequence
<220> FEATURE:
<223> OTHER INFORMATION: Synthetic Construct

<400> SEQUENCE: 34

Gly Pro Gln Gly Val Ala Gly Gln
1               5

<210> SEQ ID NO 35
<211> LENGTH: 8
<212> TYPE: PRT
```

```
<213> ORGANISM: Artificial Sequence
<220> FEATURE:
<223> OTHER INFORMATION: Synthetic Construct

<400> SEQUENCE: 35

Gly Pro Gln Gly Arg Ala Gly Gln
1               5

<210> SEQ ID NO 36
<211> LENGTH: 8
<212> TYPE: PRT
<213> ORGANISM: Artificial Sequence
<220> FEATURE:
<223> OTHER INFORMATION: Synthetic Construct

<400> SEQUENCE: 36

Gly Pro Gln Gly Ile Ala Ser Gln
1               5

<210> SEQ ID NO 37
<211> LENGTH: 8
<212> TYPE: PRT
<213> ORGANISM: Artificial Sequence
<220> FEATURE:
<223> OTHER INFORMATION: Synthetic Construct

<400> SEQUENCE: 37

Gly Pro Gln Gly Ile Phe Gly Gln
1               5

<210> SEQ ID NO 38
<211> LENGTH: 8
<212> TYPE: PRT
<213> ORGANISM: Artificial Sequence
<220> FEATURE:
<223> OTHER INFORMATION: Synthetic Construct

<400> SEQUENCE: 38

Gly Pro Gln Gly Ile Trp Gly Gln
1               5

<210> SEQ ID NO 39
<211> LENGTH: 7
<212> TYPE: PRT
<213> ORGANISM: Artificial Sequence
<220> FEATURE:
<223> OTHER INFORMATION: Synthetic Construct

<400> SEQUENCE: 39

Ala Leu Lys Val Leu Lys Gly
1               5

<210> SEQ ID NO 40
<211> LENGTH: 6
<212> TYPE: PRT
<213> ORGANISM: Artificial Sequence
<220> FEATURE:
<223> OTHER INFORMATION: Synthetic Construct

<400> SEQUENCE: 40

Ser Phe Leu Leu Arg Asn
1               5

<210> SEQ ID NO 41
<211> LENGTH: 5
<212> TYPE: PRT
<213> ORGANISM: Artificial Sequence
```

```
<220> FEATURE:
<223> OTHER INFORMATION: Synthetic Construct

<400> SEQUENCE: 41

Thr Phe Leu Leu Arg
1               5

<210> SEQ ID NO 42
<211> LENGTH: 6
<212> TYPE: PRT
<213> ORGANISM: Artificial Sequence
<220> FEATURE:
<223> OTHER INFORMATION: Synthetic Construct

<400> SEQUENCE: 42

Gly Tyr Pro Gly Lys Phe
1               5

<210> SEQ ID NO 43
<211> LENGTH: 5
<212> TYPE: PRT
<213> ORGANISM: Artificial Sequence
<220> FEATURE:
<223> OTHER INFORMATION: Synthetic Construct

<400> SEQUENCE: 43

Ala Tyr Pro Gly Lys
1               5

<210> SEQ ID NO 44
<211> LENGTH: 6
<212> TYPE: PRT
<213> ORGANISM: Artificial Sequence
<220> FEATURE:
<223> OTHER INFORMATION: Synthetic Construct

<400> SEQUENCE: 44

Ala Tyr Pro Gly Lys Phe
1               5

<210> SEQ ID NO 45
<211> LENGTH: 12
<212> TYPE: PRT
<213> ORGANISM: Artificial Sequence
<220> FEATURE:
<223> OTHER INFORMATION: Synthetic Construct

<400> SEQUENCE: 45

Lys Cys Gly Pro Gln Gly Ile Trp Gly Gln Cys Lys
1               5                   10

<210> SEQ ID NO 46
<211> LENGTH: 12
<212> TYPE: PRT
<213> ORGANISM: Artificial Sequence
<220> FEATURE:
<223> OTHER INFORMATION: Synthetic Construct

<400> SEQUENCE: 46

Lys Cys Gly Pro Gln Gly Ile Ala Gly Gln Cys Lys
1               5                   10

<210> SEQ ID NO 47
<211> LENGTH: 9
<212> TYPE: PRT
<213> ORGANISM: Artificial Sequence
<220> FEATURE:
```

```
<223> OTHER INFORMATION: Synthetic Construct

<400> SEQUENCE: 47

Cys Ala Leu Lys Val Leu Lys Gly Cys
1               5

<210> SEQ ID NO 48
<211> LENGTH: 5
<212> TYPE: PRT
<213> ORGANISM: Artificial Sequence
<220> FEATURE:
<223> OTHER INFORMATION: Synthetic Construct

<400> SEQUENCE: 48

Cys Arg Gly Asp Ser
1               5
```